US012590078B2

(12) United States Patent
Marcin et al.

(10) Patent No.: US 12,590,078 B2
(45) Date of Patent: Mar. 31, 2026

(54) INHIBITING USP19

(71) Applicant: Valo Health, Inc., Lexington, MA (US)

(72) Inventors: Lawrence Marcin, Boston, MA (US); Bingsong Han, Boston, MA (US); Stephanos Ioannidis, Boston, MA (US); Katherine Kayser-Bricker, Boston, MA (US); Cuixian Liu, Boston, MA (US); Adam Talbot, Boston, MA (US)

(73) Assignee: Valo Health, Inc., Lexington, MA (US)

( * ) Notice: Subject to any disclaimer, the term of this patent is extended or adjusted under 35 U.S.C. 154(b) by 1053 days.

(21) Appl. No.: 17/609,105

(22) PCT Filed: May 6, 2020

(86) PCT No.: PCT/US2020/031608

§ 371 (c)(1),
(2) Date: Nov. 5, 2021

(87) PCT Pub. No.: WO2020/227365

PCT Pub. Date: Nov. 12, 2020

(65) Prior Publication Data

US 2022/0213059 A1 Jul. 7, 2022

Related U.S. Application Data

(60) Provisional application No. 62/843,801, filed on May 6, 2019, provisional application No. 62/857,598, filed on Jun. 5, 2019.

(51) Int. Cl.
*C07D 401/06* (2006.01)
*C07D 401/14* (2006.01)
(Continued)

(52) U.S. Cl.
CPC ......... *C07D 401/06* (2013.01); *C07D 401/14* (2013.01); *C07D 413/14* (2013.01); *C07D 417/14* (2013.01); *C07D 487/04* (2013.01)

(58) Field of Classification Search
None
See application file for complete search history.

(56) References Cited

U.S. PATENT DOCUMENTS

2016/0185786 A1* 6/2016 Ioannidis ................ A61P 19/08 435/375

FOREIGN PATENT DOCUMENTS

JP 2002047272 A * 2/2002
JP 2018500377 A 1/2018
(Continued)

OTHER PUBLICATIONS

Barriero et. al. "The Methylation Effect in Medicinal Chemistry" Chemical Reviews 2011, 111, 5215-5246. DOI: 10.1021/cr200060g (Year: 2011).*

(Continued)

*Primary Examiner* — Jennifer A Berrios
*Assistant Examiner* — Sophia Reilly
(74) *Attorney, Agent, or Firm* — Barnes & Thornburg LLP; Aisha R. Hasan; Ryan L. Marshall

(57) ABSTRACT

The present disclosure is directed to compounds of formulas (I)-(VI), which are useful as modulators of USP19. The compounds are further useful in the inhibition of USP19 and the treatment of diseases or disorders associated with the inhibition of USP19. For instance, the disclosure is concerned with compounds and compositions for inhibition of USP19 and methods of treating diseases associated with the inhibition of USP19 (e.g., Parkinson's disease, Ewing sarcoma, and other metabolic diseases including muscle wasting and diabetes).

(I)

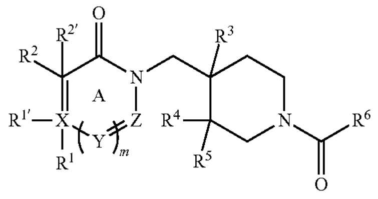

(II)

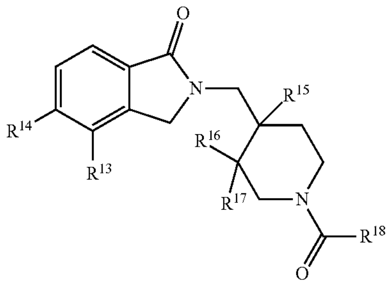

(II-A)

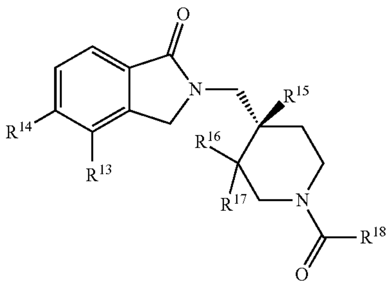

(Continued)

-continued (III)

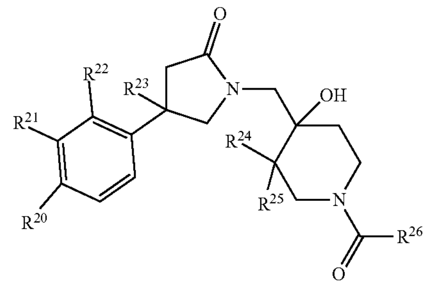

(III-A)

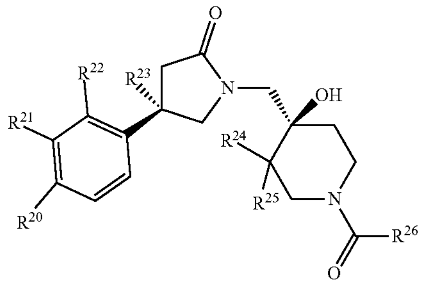

(III-B)

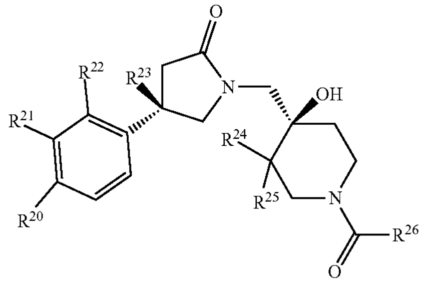

(IV)

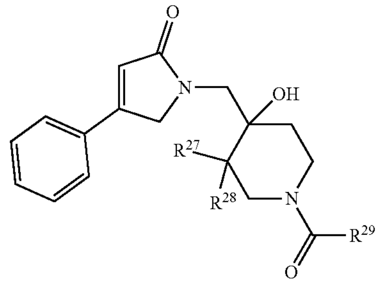

(IV-A)

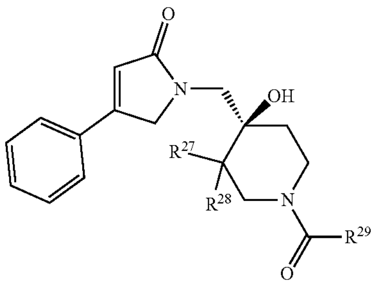

-continued (V)

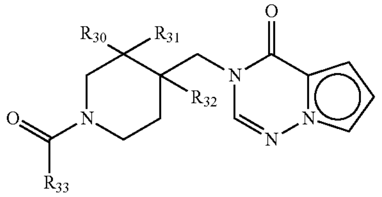

(V-A)

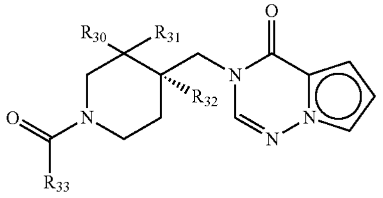

(V-B)

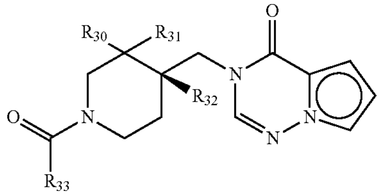

(VI)

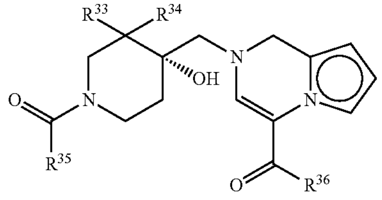

12 Claims, No Drawings

(51) Int. Cl.

| | |
|---|---|
| *C07D 413/14* | (2006.01) |
| *C07D 417/14* | (2006.01) |
| *C07D 487/04* | (2006.01) |

(56) References Cited

FOREIGN PATENT DOCUMENTS

| | | | | | |
|---|---|---|---|---|---|
| JP | 2021525220 | A | | 9/2021 | |
| JP | 2022510700 | A | | 1/2022 | |
| WO | 2001064670 | A1 | | 9/2001 | |
| WO | WO-2011006794 | A1 | * | 1/2011 | ................ A61P 9/00 |
| WO | 2016109480 | A1 | | 7/2016 | |
| WO | WO-2017212010 | A1 | * | 12/2017 | ........... A61K 31/519 |
| WO | 2018020242 | A1 | | 2/2018 | |
| WO | 2018073602 | A1 | | 4/2018 | |
| WO | 2019067503 | A1 | | 4/2019 | |
| WO | WO-2019150119 | A1 | * | 8/2019 | ........... A61K 31/438 |
| WO | 2020115500 | A1 | | 6/2020 | |

OTHER PUBLICATIONS

Australian Examination Report for Australian Application 2020267757, Dec. 20, 2024, 3 pages.

First Office Action for Chinese Application CN2020800424591, Aug. 30, 2023, 8 pages.

(56) References Cited

OTHER PUBLICATIONS

Second Office Action for Chinese Application CN2020800424591, Mar. 4, 2024, 6 pages.
European Search Opinion for EP Application 208015024, May 19, 2023, 2 pages.
International Search Report for PCT Application PCT/US2020/031608, Sep. 16, 2020, 3 pages.
Japanese Search Report for JP Application 2021-563425, Apr. 25, 2024, 21 pages.
Japanese Written Opinion for JP Application 2021-563425, Aug. 14, 2024, 3 pages.
Japanese Notice of Reasons for Refusal for JP Application 2021-563425, May 1, 2024, 6 pages.
O'Dowd et al, "Identification and Structure-Guided Development of Pyrimidinone Based UJSP7 Inhibitors", ACS Medicinal Chemistry Letters, 2018, pp. 238-243.
Pubmed Compound Record for CID 57844343, Aug. 2012, p. 1-8.
Pubmed Compound Record for CID 68291125, Nov. 2012, p. 1-8.
Pubmed Compound Record for CID 71801580, Jun. 30, 2016, pp. 1-9.

* cited by examiner

INHIBITING USP19

CROSS REFERENCE TO RELATED APPLICATIONS

This application is a National Stage application of International Application No. PCT/US2020/031608, filed May 6, 2020, which claims the benefit of U.S. Provisional Application No. 62/843,801, filed May 6, 2019, and U.S. Provisional Application No. 62/857,598, filed Jun. 5, 2019, each of which is incorporated by reference herein in its entirety.

TECHNICAL FIELD

The present disclosure relates to compounds useful for the inhibition of USP19. Inhibitors of USP19 are useful compounds for the treatment of Parkinson's disease, Ewing sarcoma, and other metabolic diseases including muscle wasting and diabetes.

BACKGROUND

The ubiquitin proteasome system (UPS) is a master regulator of protein homeostasis in eukaryotic cells. The control of protein turnover by the UPS is partially governed by ubiquitin activating, conjugating, and ligating enzymes, which post-translationally modify target proteins with covalent linked ubiquitin, an 8-kDa protein. The nature and length of the covalent linkage with ubiquitin often dictates the fate and/or degradation of the target protein by the proteasome. Importantly, ubiquitination is a reversible process that can be catalyzed by deubiquitinating enzymes (DUBs). In humans, there are approximately 100 unique DUBs grouped into 5 subfamilies. The ubiquitin specific peptidase (USP) family is the largest DUB subfamily with more than 50 members, including USP19. USP19 is a 150-kDa protein expressed in a variety of tissues. In addition to its USP catalytic core, USP19 exhibits several interesting structural domains including myeloid translocation protein 8, Nervy and Deaf (MYND), and CHORD/SGT1 (CS/p23) domains that may mediate protein-protein interactions or protein chaperoning.

USP19 is involved in many cellular processes including autophagy and immune response, endoplasmic reticulum-associated degradation, misfolding-associated protein secretion, cell proliferation and hypoxia. Notably, USP19 plays an important role in muscle as it regulates myogenic differentiation and female muscle mass through estrogen receptor-dependent mechanisms. USP19 expression is induced in muscle tissue under catabolic stimuli and the inactivation of the gene in mice is protective against muscle wasting. Furthermore, loss of USP19 activity in mice results in decreased fat mass, in part through a reduction of the adipogenic capacity of adipocyte precursor cells. The decrease in fat mass in USP19 −/− mice is accompanied by an increase in lean mass and improved glucose tolerance and insulin sensitivity/signaling in the liver and skeletal muscle of mice fed a high-fat diet. Similarly, USP19 may be important for human adipose tissue function since USP19 mRNA expression is positively correlated with adipogenic gene expression in human adipose tissue samples. USP19 may also have an unrelated function in unconventional secretion of misfolded cytosolic proteins such as tau and alpha-synuclein. In this role, USP19 binds HSC70 and acts upstream of HSC70 and DNAJC5, an essential mediator of misfolded-associated protein secretion (MAPs). Upon secretion, misfolded proteins can be taken up through endocytosis and eventually degraded in the lysosome. These findings suggest a transcellular protein quality control regulatory pathway in which a deubiquitinase-chaperone axis forms a "triaging hub", transferring aberrant polypeptides from stressed cells to healthy ones for disposal. However, in the case of neurodegenerative diseases, such as Parkinson's disease or Alzheimer's disease, this process may contribute to cell-to-cell transmission of misfolded proteins and disease progression. USP19 has recently been identified as a regulator of EWS-FL1 stability using a siRNA based screening approach. Depletion of USP19 resulted in diminished EWS-FLI1 protein levels and, vice versa, upregulation of active USP19 stabilized the fusion protein. Importantly, stabilization appears to be specific for the fusion protein as it could not be observed neither for EWSR1 nor for FLI1 wild type proteins even though USP19 binds to the N-terminal EWS region to regulate deubiquitination of both EWS-FLI1 and EWSR1. Furthermore, stable shUSP19 depletion resulted in decreased cell growth and diminished colony-forming capacity in vitro, and significantly delayed tumor growth in vivo.

SUMMARY

In one aspect, compounds of formula (I) are disclosed:

(I)

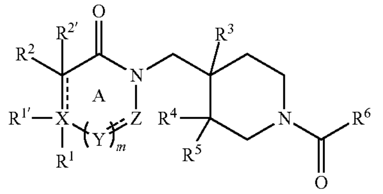

and pharmaceutically acceptable salts, hydrates, solvates, isomers, enantiomers, diastereomers, and tautomers thereof, where the substituents are described herein.

In another aspect, a method of treating, preventing inhibiting, or eliminating a disease or disorder associated with the activity of USP19 in a patient is disclosed which includes administering to the patient in need thereof, a therapeutically effective amount of the foregoing compounds, or pharmaceutical compositions thereof.

DETAILED DESCRIPTION

The present disclosure relates to compounds, and pharmaceutical compositions thereof, that are capable of modulating the activity of ubiquitin specific peptidase 19 (USP19). The disclosure features methods of treating, preventing, or ameliorating a disease or disorder in which USP19 plays a role by administering to a patient in need thereof a therapeutically effective amount of a compound of any one of formulas (I)-(VI), or an enantiomer, diastereomer, or pharmaceutically acceptable salt thereof. The disclosure also features methods of treating, preventing, or ameliorating a disease or disorder in which USP19 plays a role by administering to a patient in need thereof a therapeutically effective amount of a pharmaceutical composition of a compound of any one of formulas (I)-(VI), or an enantiomer, diastereomer, or pharmaceutically acceptable salt thereof. The methods of the present disclosure can be used in the treatment of a variety of USP19-dependent diseases and disorders by inhibiting the activity of USP19.

Inhibition of USP19 provides a novel approach to the treatment of diseases including, but not limited to, Parkinson's disease, Ewing sarcoma, and other metabolic diseases including muscle wasting and diabetes.

Definitions

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety can be (but is not required to be) bonded to other substituents. Unless otherwise specifically defined, optional substituents may be bonded to the chemical moiety with any chemically feasible regiochemistry and/or stereochemistry (where applicable). For instance, an alkyl group that is optionally substituted can be a fully saturated alkyl chain (e.g., a pure hydrocarbon). Alternatively, the same optionally substituted alkyl group can have substituents in place of one or more hydrogen atoms. For instance, it can be bonded, at any point along the chain. Thus, the term "optionally substituted" means that a given chemical moiety has the potential to contain other functional groups, but does not necessarily have any further functional groups. "Optionally substituted" as used herein also refers to substituted or unsubstituted whose meaning is described below.

As used herein, the term "substituted" means that the specified group or moiety bears one or more of the recited substituents, wherein the substituents may connect to the specified group or moiety at one position. Unless otherwise specifically defined, substituents may be bonded to the chemical moiety with any chemically feasible regiochemistry and/or stereochemistry (where applicable).

As used herein, the term "unsubstituted" means that the specified group bears no substituents.

As used herein, the term "aryl" refers to a monocyclic, aromatic hydrocarbon group that has one aromatic ring having a total of 5 to 10 carbon atoms, such as, for example, phenyl.

As used herein, the term "heteroaryl" refers to a monocyclic or bicyclic aromatic group of 5 to 10 ring atoms, containing one or more ring heteroatoms selected from the group consisting of N, O, and S, the remaining ring atoms being C. Examples of monocyclic heteroaryl groups include, but are not limited to, furyl, thienyl, pyrrolyl, pyridinyl, pyrazolyl, pyrimidinyl, imidazolyl, isoxazolyl, oxazolyl, oxadiazolyl, pyrazinyl, thiophen-2-yl, isothiazolyl, thiazolyl, thiadiazolyl, 1,2,4-thiadiazolyl, 1,3,4-thiadiazolyl, triazolyl, triazinyl. Examples of bicyclic heteroaryl groups include, but are not limited to, indolyl, quinolyl, benzopyranyl, indazolyl, benzimidazolyl, thieno[3,2-b]thiophene, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuranyl, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, and imidazo[2,1-b][1,3,4]thiadiazolyl. Unless otherwise specifically defined, "heteroaryl" groups are unsubstituted.

As used herein, the term "5-membered heteroaryl" refers to a heteroaryl, as defined herein, having a total of 5 ring atoms. Examples of "5-membered heteroaryl" groups include, but are not limited to pyrazolyl, oxazolyl, and thiazolyl. Unless otherwise specifically defined, "5-membered heteroaryl" groups are unsubstituted.

As used herein, the term "$C_{1-4}$ alkyl" refers to a straight or branched, saturated hydrocarbon chain group containing 1 to 4 carbon atoms. Examples of $C_{1-4}$ alkyl groups include, but are not limited to, methyl, ethyl, propyl (e.g. n-propyl), isopropyl, butyl (e.g. n-butyl), sec-butyl, isobutyl, and tert-butyl. "$C_1$ alkyl" refers to an alkyl chain containing 1 carbon atom, e.g. methyl. "$C_2$ alkyl" refers to an alkyl chain containing 2 carbon atoms, e.g. ethyl. "$C_3$ alkyl" refers to an alkyl chain containing 3 carbon atoms, e.g. propyl (i.e. n-propyl) or isopropyl. "$C_4$ alkyl" refers to an alkyl chain containing 4 carbon atoms, e.g. butyl (i.e. n-butyl), isobutyl, sec-butyl, or tert-butyl. Unless otherwise specifically defined, "$C_{1-4}$ alkyl" groups are unsubstituted.

As used herein, the term "$C_{1-4}$ alkoxy" refers to a straight or branched saturated hydrocarbon chain containing 1 to 4 carbon atoms and a terminal oxygen atom, i.e. —O—$C_{1-4}$ alkyl. Examples of $C_{1-4}$ alkoxy groups include, but are not limited to, methoxy, ethoxy, propoxy, isopropoxy, butoxy, and tert-butoxy. Unless otherwise specifically defined, "$C_{1-4}$ alkoxy" groups are unsubstituted, other than as the term is defined herein.

As used herein, the term "haloalkyl" refers to a $C_{1-4}$ alkyl group, as defined herein, which is substituted with one or more halogen. Examples of haloalkyl groups include, but are not limited to, trifluoromethyl, difluoromethyl, pentafluoroethyl, trichloromethyl, etc. Unless otherwise specifically defined, "haloalkyl" groups are unsubstituted, other than as the term is defined herein.

As used herein, the term "cycloalkyl" refers to a monocyclic saturated ring containing 3-8 carbon atoms. Examples of cycloalkyl groups include, but are not limited to, cyclopropyl, cyclobutyl, cyclopentyl, cyclohexyl, cycloheptyl, and cyclooctyl. "$C_3$ cycloalkyl" refers to a cycloalkyl containing 3 carbon atoms, e.g. cyclopropyl. "$C_4$ cycloalkyl" refers to a cycloalkyl containing 4 carbon atoms, e.g. cyclobutyl. "$C_5$ cycloalkyl" refers to a cycloalkyl containing 5 carbon atoms, e.g. cyclopentyl. "$C_6$ cycloalkyl" refers to a cycloalkyl containing 6 carbon atoms, e.g. cyclohexyl. Unless otherwise specifically defined, "cycloalkyl" groups are unsubstituted.

As used herein, the term "spirocycloalkyl" refers to a bicyclic ring system having 6-12 carbon atoms, wherein the rings are connected to one another through a single atom. The rings can be different in size and nature, or identical in size and nature. Examples include, but are not limited to, spirohexane, spiroheptane, spirooctane, spirononane, spirodecane, spiroundecane, and spirododecane. Unless otherwise specifically defined, "spirocycloalkyl" groups are unsubstituted.

As used herein, the term "5 to 6 membered heterocyclyl" refers to a monocyclic ring containing a total of 5 to 6 carbon and heteroatoms taken from oxygen, nitrogen, or sulfur, where such rings are either saturated or partially unsaturated. Examples of heterocyclyl rings include, but are not limited to, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, morpholinyl, thiomorpholinyl, thiomorpholinyl S-oxide, thiomorpholinyl S-dioxide, piperazinyl, and oxazolidinonyl. Unless otherwise specifically defined, "5 to 6 membered heterocyclyl" groups are unsubstituted.

As used herein, the term "spiroheterocyclyl" refers to a bicyclic ring system having a total of 6-12 atoms, wherein carbon and heteroatoms taken from oxygen, nitrogen, or sulfur, wherein such rings are either saturated or partially unsaturated and the rings are connected to one another through a single atom. The rings can be different in size and nature, or identical in size and nature. An example of a spiroheterocyclyl is 7-azaspiro[4.5]decane. Unless otherwise specifically defined, "spiroheterocyclyl" groups are unsubstituted.

As used herein, the term "alkylcycloalkyl" refers to a functional group composed of an optionally substituted $C_{1-4}$ alkyl chain that terminates in a $C_{3-6}$ cycloalkyl ring. Non-limiting, specific examples of alkylcycloalkyl groups include

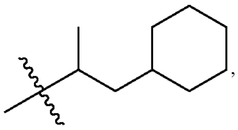,
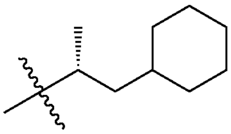
and
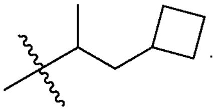.

As used above herein, the term "alkylaryl" refers to a functional group comprised of an optionally substituted $C_1$-4 alkyl chain that terminates in an aryl ring. A non-limiting, specific example of an alkylaryl group is

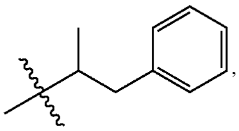 [SMILES: *C(C)Cc1ccccc1], which may be referred to as "alkylphenyl".

As used herein, the term "alkylheteroaryl" refers to a functional group composed of an optionally substituted $C_{1-4}$ alkyl chain that terminates in a heteroaryl ring. Non-limiting, specific examples of an alkylheteroaryl group are

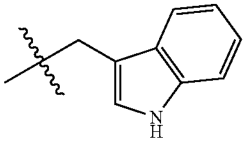
and
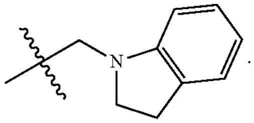.

As used herein, the term "halogen" or "halo" refers to fluorine (i.e. "F" or "fluoro"), chlorine (i.e. "Cl" or "choro"), bromine (i.e. "Br" or "bromo"), or iodine (i.e. "I" or "iodo").

As used herein, the term "isomer" refers to compounds that have the same composition and molecular weight but differ in physical and/or chemical properties. The structural difference may be in constitution (e.g., geometric isomers) or in the ability to rotate a plane of polarized light (stereoisomers). With regard to stereoisomers, the compounds of formulas (I)-(VI) may have one or more asymmetric carbon atoms and may occur as racemates, racemic mixtures, or as individual enantiomers or diastereomers.

The term "pharmaceutical composition" as used herein, refers to a composition in which individual components or ingredients are themselves pharmaceutically acceptable, e.g., where oral administration is foreseen, acceptable for oral use; where topical administration is foreseen, topically acceptable; and where intravenous administration is foreseen, intravenously acceptable.

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

"Pharmaceutically acceptable salts" are well known in the art. For example, S. M. Berge et al., describe pharmaceutically acceptable salts in detail in J. Pharmaceutical Sciences, 1977, 66, 1-19, incorporated herein by reference. Representative pharmaceutically acceptable salts include, e.g., water-soluble and water-insoluble salts, such as acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. The compounds of formulas (I)-(VI) may form salts, which are also within the scope of this disclosure. Reference to a compound of any one of formulas (I)-(VI) herein is understood to include reference to salts thereof, unless otherwise indicated.

Novel USP19 inhibitors are provided. Unless otherwise indicated "USP19 Inhibitor Compound" as used herein refers to a compound having a detectable $IC_{50}$ value of 15 micromolar or lower, when tested according to the USP19 inhibition biochemical assay of Example 4 described hereafter.

A "patient" or "subject" is a mammal, e.g., a human, mouse, rat, guinea pig, dog, cat, horse, cow, pig, or non-human primate, such as a monkey, chimpanzee, baboon, or rhesus.

As used herein, the term "therapeutically effective amount" refers to that amount of the therapeutic agent sufficient to result in amelioration of one or more symptoms of a disorder, or prevent advancement of a disorder, or cause regression of the disorder.

The term "carrier", as used in this disclosure, encompasses carriers, excipients, and diluents and means a material, composition or vehicle, such as a liquid or solid filler, diluent, excipient, solvent, or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound, a pharmaceutically acceptable salt of a disclosed compound or a composition that includes a disclosed compound to a subject, which can form an equivalent amount of active compound within the subject's body.

Compounds of the Disclosure

The present disclosure relates to compounds, or pharmaceutically acceptable salts and isomers thereof, capable of modulating USP19, which are useful for the treatment of diseases and disorders associated with modulation of USP19. The disclosure further relates to compounds, or pharmaceutically acceptable salts and isomers thereof, which are useful for inhibiting USP19.

Unless otherwise indicated herein, all isomeric forms of specified chemical compounds are provided by the present disclosure, including mixtures thereof. All tautomeric forms are also intended to be included.

The compounds of formulas (I)-(VI), unless otherwise indicated, may contain one or more stereocenters, and, therefore, exist in different stereoisomeric forms. It is intended that unless otherwise indicated all stereoisomeric forms of the compounds of formulas (I)-(VI), as well as mixtures thereof, including racemic mixtures, form part of the present disclosure. In addition, the present disclosure embraces all geometric and positional isomers. For example, if a compound of any one of formulas (I)-(VI) incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry. Individual stereoisomers of the compounds of the disclosure may be, for example, substantially free of other isomers, or may be admixed, for example, as racemates or with all other, or other selected, stereoisomers. In some embodiments of the disclosure, the compounds of formula (I)-(VI) are enantiomers. In some embodiments, the compounds are the (S)-enantiomer. In other embodiments, the compounds are the (R)-enantiomer. In some embodiments, the compounds of formulas (I)-(VI) may be (+) or (−) enantiomers.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of formulas (I)-(VI) may be atropisomers (e.g., substituted biaryls) and are considered as part of this disclosure. Enantiomers can also be separated by use of a chiral HPLC column.

Compounds of the disclosure, and pharmaceutically acceptable salts and stereoisomers, thereof may exist in their tautomeric form (for example, as an amide or imino ether). Moreover, all keto-enol and imine-enamine forms of the compounds are included in the disclosure. All such tautomeric forms are contemplated herein as part of the present disclosure.

When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, iron (III), iron (II), lithium, magnesium, manganese, potassium, sodium, zinc, and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When compounds of the present invention contain relatively basic functionalities, acid addition salts can be obtained by contacting the neutral form of such compounds with a sufficient amount of the desired acid, either neat or in a suitable inert solvent. Acids suitable for the preparation of pharmaceutically acceptable acid addition salts include acetic, ascorbic, benzenesulfonic, benzoic, camphorsulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic, and the like.

The use of the terms "salt" and the like, is intended to equally apply to the salt of enantiomers, stereoisomers, rotamers, tautomers, positional isomers, and racemates of the inventive compounds.

The compounds of formulas (I)-(VI) may form acid addition salts or base addition salts, which may be pharmaceutically acceptable salts.

Compounds of formula (I) are disclosed:

(I)

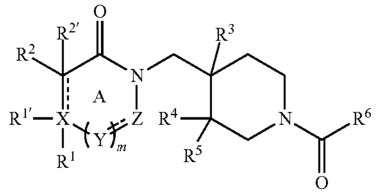

and pharmaceutically acceptable salts, hydrates, solvates, isomers, enantiomers, diastereomers, and tautomers thereof, wherein:

X is N or C;

wherein if X is N, one of $R^1$ and $R^{1'}$ is absent;

Y is N or $CR^7$;

Z is $CH_2$;

$R^1$ and $R^{1'}$ are each independently selected from H, $C_{1-4}$ alkyl, and aryl optionally substituted with one $R^8$;

$R^2$ and $R^{2'}$ are each independently selected from H and $C_{1-4}$ alkyl;

wherein one of $R^1$ or $R^{1'}$ may be joined to one of $R^2$ or $R^{2'}$ to form an aryl or heteroaryl ring that includes the atoms to which they are attached and is substituted with one $R^9$;

one of $R^1$ or $R^{1'}$ and one of $R^2$ or $R^{2'}$ may be absent, such that ring A contains an unsaturated bond between X and the carbon to which $R^2$ and $R^{2'}$ are connected;

$R^3$ is selected from: H, —$OR^{10}$, and halogen;

$R^4$ is H or $C_{1-4}$ alkyl;

$R^5$ is H or $C_{1-4}$ alkyl;

wherein $R^4$ and $R^5$ may be joined to one another to form a cycloalkyl that includes the carbon to which they are attached;

$R^6$ is selected from: alkylcycloalkyl, alkylaryl, and alkylheteroaryl, each of which may optionally be substituted with one $C_{1-4}$ alkyl;

$R^7$ is —$C(O)R^{11}$;

$R^8$ is selected from: halogen, $C_{1-4}$ alkyl, and $C_{1-4}$ alkoxy;

$R^9$ is selected from: H, halogen, $C_{1-4}$ alkyl, $C_{1-4}$ alkoxy, —$C(O)N(R^{12})_2$, and heteroaryl;

$R^{10}$ is H or $C_{1-4}$ alkyl;

$R^{11}$ is —$N(R^{12})_2$ or a 5 to 6-membered heterocycle containing two heteroatoms selected from N and O;

$R^{12}$ is a $C_{1-4}$ alkyl group; and m is 0 or 1, wherein if m is 1:

ring A contains an unsaturated bond between Y and Z;

X is N; and if both X and Y are N, $R^9$ is H.

In some embodiments, compounds of formula (IA) are disclosed:

(IA)

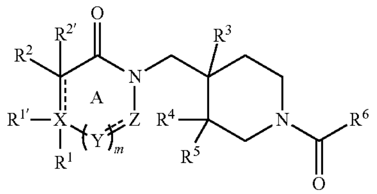

and pharmaceutically acceptable salts, hydrates, solvates, isomers, enantiomers, diastereomers, and tautomers thereof, wherein:

X is N or C, wherein:

if X is N, one of $R^1$ and $R^{1'}$ is absent;

Y is N or $CR^7$;

Z is $CH_2$;

m is 0 or 1, wherein if m is 1, ring A contains an unsaturated bond between Y and Z;

$R^1$ and $R^{1'}$ are each independently selected from H, $C_{1-4}$ alkyl, and aryl optionally substituted with one $R^8$;

$R^2$ and $R^{2'}$ are each independently selected from H and $C_{1-4}$ alkyl, wherein:

one of $R^1$ or $R^{1'}$ may be joined to one of $R^2$ or $R^{2'}$ to form an aryl or heteroaryl ring that includes the atoms to which they are attached and is optionally substituted with one $R^9$; and one of $R^1$ or $R^{1'}$ and one of $R^2$ or $R^{2'}$ may be absent, such that ring A contains an unsaturated bond between X and the carbon to which $R^2$ and $R^{2'}$ are connected;

$R^3$ is selected from: H, —OR', and halogen;

$R^4$ and $R^5$ are H or $C_{1-4}$ alkyl, wherein $R^4$ and $R^5$ may be joined to one another to form a cycloalkyl that includes the carbon to which they are attached;

$R^6$ is selected from: alkylcycloalkyl, alkylaryl, and alkylheteroaryl, each of which may optionally be substituted with one $C_{1-4}$ alkyl;

$R^7$ is —$C(O)R^{11}$;

$R^8$ is selected from: halogen, $C_{1-4}$ alkyl, and $C_{1-4}$ alkoxy;

$R^9$ is selected from: halogen, $C_{1-4}$ alkyl, $C_{1-4}$ alkoxy, —$C(O)N(R^{12})_2$, and heteroaryl;

$R^{10}$ is H or $C_{1-4}$ alkyl;

$R^{11}$ is —$N(R^{12})_2$ or a 5 to 6-membered heterocycle containing two heteroatoms selected from N and O; and $R^{12}$ is a $C_{1-4}$ alkyl group.

In some embodiments, X is N or C. In some embodiments, X is N. In some embodiments, X is C.

In some embodiments, Y is N or $CR^7$. In some embodiments, Y is N. In some embodiments, Y is $CR^7$.

In some embodiments, $R^1$ and $R^{1'}$ are each independently selected from H, $C_{1-4}$ alkyl, and aryl optionally substituted with one $R^8$. In some embodiments, $R^1$ and $R^{1'}$ are each independently selected from H, $C_{1-3}$ alkyl, and phenyl optionally substituted with one $R^8$. In some embodiments, $R^1$ and $R^{1'}$ are each independently selected from H, methyl, ethyl, propyl, and phenyl optionally substituted with one $R^8$. In some embodiments, $R^1$ and $R^{1'}$ are each independently selected from methyl, ethyl, propyl, and phenyl optionally substituted with one $R^8$. In some embodiments, $R^1$ and $R^{1'}$ are each independently selected from H, ethyl, propyl, and phenyl optionally substituted with one $R^8$. In some embodiments, $R^1$ and $R^{1'}$ are each independently selected from H, methyl, propyl, and phenyl optionally substituted with one $R^8$. In some embodiments, $R^1$ and $R^{1'}$ are each independently selected from H, methyl, ethyl, and phenyl optionally substituted with one $R^8$. In some embodiments, $R^1$ and $R^{1'}$ are each independently selected from H, methyl, ethyl, and propyl. In some embodiments, $R^1$ and $R^{1'}$ are each H. In some embodiments, $R^1$ and $R^{1'}$ are each independently H or methyl. In some embodiments, $R^1$ and $R^{1'}$ are each independently H or ethyl. In some embodiments, $R^1$ and $R^{1'}$ are each independently H or propyl. In some embodiments, $R^1$ and $R^{1'}$ are each independently H or phenyl optionally substituted with one $R^8$.

In some embodiments, $R^2$ and $R^{2'}$ are each independently selected from H and $C_{1-4}$ alkyl. In some embodiments, $R^2$ and $R^{2'}$ are each independently selected from H and $C_{1-3}$ alkyl. In some embodiments, $R^2$ and $R^{2'}$ are each independently selected from H, methyl, ethyl, and propyl. In some embodiments, $R^2$ and $R^{2'}$ are each independently selected from methyl, ethyl, and propyl. In some embodiments, $R^2$ and $R^{2'}$ are each independently selected from H, ethyl, and propyl. In some embodiments, $R^2$ and $R^{2'}$ are each independently selected from H, methyl, and propyl. In some embodiments, $R^2$ and $R^{2'}$ are each independently selected from H, methyl, and ethyl. In some embodiments, $R^2$ and $R^{2'}$ are each H. In some embodiments, $R^2$ and $R^{2'}$ are each independently H or methyl. In some embodiments, $R^2$ and $R^{2'}$ are each independently H or ethyl. In some embodiments, $R^2$ and $R^{2'}$ are each H or propyl.

In some embodiments, one of $R^1$ or $R^{1'}$ is joined to one of $R^2$ or $R^{2'}$ to form an aryl or heteroaryl ring that includes the atoms to which they are attached and is substituted with one $R^9$. In some embodiments, one of $R^1$ or $R^{1'}$ is joined to one of $R^2$ or $R^{2'}$ to form a phenyl ring that includes the atoms to which they are attached and is substituted with one $R^9$.

In some embodiments, one of $R^1$ or $R^{1'}$ and one of $R^2$ or $R^{2'}$ are absent, such that ring A contains an unsaturated bond between X and the carbon to which $R^2$ and $R^{2'}$ are connected.

In some embodiments, $R^3$ is selected from: H, —OR', and halogen. In some embodiments, $R^3$ is selected from: H, —$OR^{10}$, and F. In some embodiments, $R^3$ is —$OR^{10}$ or F. In some embodiments, $R^3$ is H or F. In some embodiments, $R^3$ is H or —OR'. In some embodiments, $R^3$ is H. In some embodiments, $R^3$ is —$OR^{10}$. In some embodiments, $R^3$ is F.

In some embodiments, $R^4$ is H or $C_{1-4}$ alkyl. In some embodiments, $R^4$ is selected from H, methyl, ethyl, propyl, and butyl. In some embodiments, $R^4$ is selected from methyl, ethyl, propyl, and butyl. In some embodiments, $R^4$ is selected from H, methyl, propyl, and butyl. In some embodiments, $R^4$ is selected from H, methyl, ethyl, propyl, and butyl. In some embodiments, $R^4$ is selected from H, methyl, ethyl, and butyl. In some embodiments, $R^4$ is selected from H, methyl, ethyl, and propyl. In some embodiments, $R^4$ is H. In some embodiments, $R^4$ is methyl.

In some embodiments, $R^5$ is H or $C_{1-4}$ alkyl. In some embodiments, $R^5$ is selected from H, methyl, ethyl, propyl, and butyl. In some embodiments, $R^5$ is selected from methyl, ethyl, propyl, and butyl. In some embodiments, $R^5$ is selected from H, methyl, propyl, and butyl. In some embodiments, $R^5$ is selected from H, methyl, ethyl, propyl, and butyl. In some embodiments, $R^5$ is selected from H, methyl, ethyl, and butyl. In some embodiments, $R^5$ is selected from H, methyl, ethyl, and propyl. In some embodiments, $R^5$ is H. In some embodiments, $R^5$ is methyl.

In some embodiments, $R^4$ and $R^5$ are joined to one another to form a cycloalkyl that includes the carbon to which they are attached. In some embodiments, $R^4$ and $R^5$ are joined to one another to form a $C_5$ cycloalkyl that includes the carbon to which they are attached. In some embodiments, both $R^4$ and $R^5$ are H.

In some embodiments, $R^6$ is selected from: alkylcycloalkyl, alkylaryl, and alkylheteroaryl, each of which may optionally be substituted with one $C_{1-4}$ alkyl. In some embodiments, $R^6$ is selected from

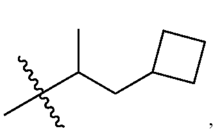
,
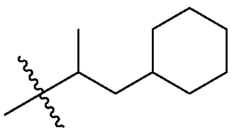
,

-continued

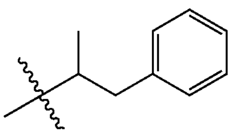
,
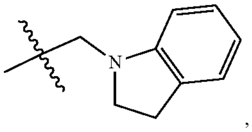
, and
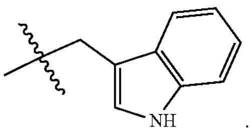
.

In some embodiments, $R^6$ is selected from

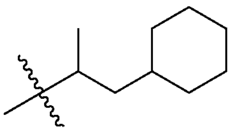
,
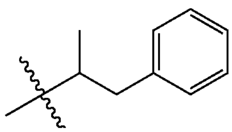
,
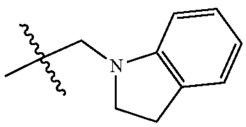
, and
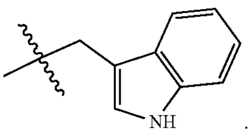
.

In some embodiments, $R^6$ is selected from

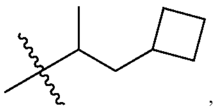
,
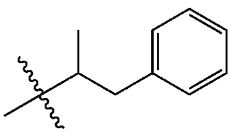
,
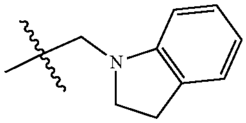
, and
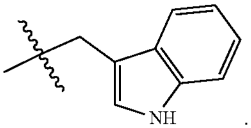
.

In some embodiments, $R^6$ is selected from

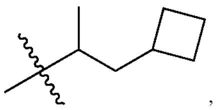
,
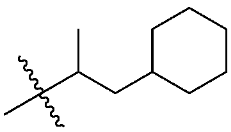
,
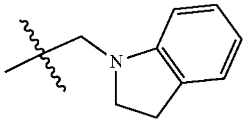
, and
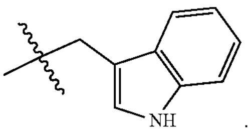
.

In some embodiments, $R^6$ is selected from

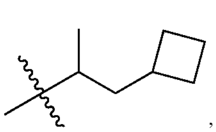
,
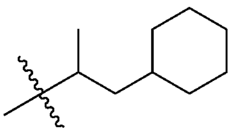
,

-continued

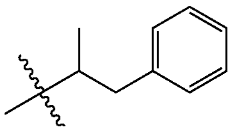, and 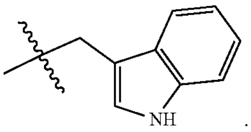.

In some embodiments, $R^6$ is selected from

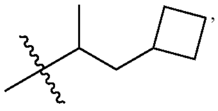, 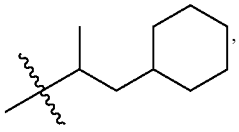,

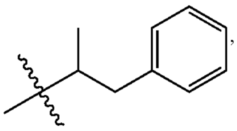, and 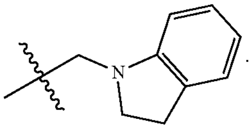.

In some embodiments, $R^6$ is

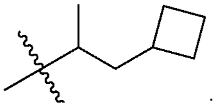 [SMILES: *C(C)CC1CCC1].

In some embodiments, $R^6$ is

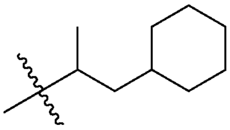.

In some embodiments, $R^6$ is

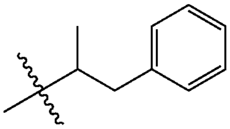.

In some embodiments, $R^6$ is

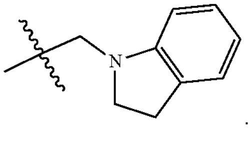 [SMILES: *CN1CCc2ccccc21].

In some embodiments, $R^6$ is

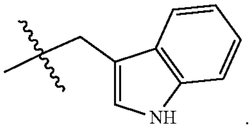 [SMILES: *Cc1c[nH]c2ccccc12].

In some embodiments,

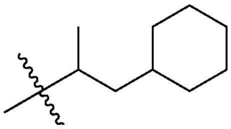

has the stereochemistry of

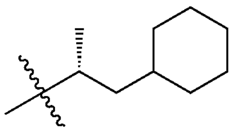.

In some embodiments, $R^8$ is selected from: halogen, $C_{1-4}$ alkyl, and $C_{1-4}$ alkoxy. In some embodiments, $R^8$ is selected from Cl, methyl, and methoxy. In some embodiments, $R^8$ is methyl or methoxy. In some embodiments, $R^8$ is Cl or methoxy. In some embodiments, $R^8$ is Cl or methyl. In some embodiments, $R^8$ is Cl. In some embodiments, $R^8$ is methyl. In some embodiments, $R^8$ is methoxy.

In some embodiments, $R^9$ is selected from: H, halogen, $C_{1-4}$ alkyl, $C_{1-4}$ alkoxy, —C(O)N($R^{12}$)$_2$, and heteroaryl. In some embodiments, $R^9$ is selected from: H, Cl, methyl, methoxy, —C(O)N($R^{12}$)$_2$, thiazolyl, oxazolyl, and pyrazolyl. In some embodiments, $R^9$ is selected from: Cl, methyl, methoxy, —C(O)N($R^{12}$)$_2$, thiazolyl, oxazolyl, and pyrazolyl. In some embodiments, $R^9$ is selected from: H, methyl, methoxy, —C(O)N($R^{12}$)$_2$, thiazolyl, oxazolyl, and pyrazolyl. In some embodiments, $R^9$ is selected from: H, Cl, methoxy, —C(O)N($R^{12}$)$_2$, thiazolyl, oxazolyl, and pyrazolyl. In some embodiments, $R^9$ is selected from: H, Cl, methyl, —C(O)N($R^{12}$)$_2$, thiazolyl, oxazolyl, and pyrazolyl. In some embodiments, $R^9$ is selected from: H, Cl, methyl, methoxy, thiazolyl, oxazolyl, and pyrazolyl. In some embodiments, $R^9$ is selected from: H, Cl, methyl, methoxy, —C(O)N($R^{12}$)$_2$, oxazolyl, and pyrazolyl. In some embodiments, $R^9$ is selected from: H, Cl, methyl, methoxy, —C(O)N($R^{12}$)$_2$, thiazolyl, and pyrazolyl. In some embodiments, $R^9$ is selected from: H, Cl, methyl, methoxy, —C(O)N($R^{12}$)$_2$, thiazolyl, and oxazolyl. In some embodiments, $R^9$ is H. In some embodiments, $R^9$ is Cl. In some embodiments, $R^9$ is methyl. In some embodiments, $R^9$ is methoxy. In some embodiments, $R^9$ is —C(O)N($R^{12}$)$_2$. In some embodiments, $R^9$ is thiazolyl. In some embodiments, $R^9$ is oxazolyl. In some embodiments, $R^9$ is pyrazolyl.

In some embodiments, $R^{10}$ is H or $C_{1-4}$ alkyl. In some embodiments, $R^{10}$ is H or methyl. In some embodiments, $R^{10}$ is H. In some embodiments, $R^{10}$ is methyl.

In some embodiments, $R^{11}$ is —N($R^{12}$)$_2$ or a 5 to 6-membered heterocycle containing two heteroatoms selected from N and O. In some embodiments, $R^{11}$ is —N($R^{12}$)$_2$ or a 6-membered heterocycle containing two heteroatoms selected from N and O. In some embodiments, $R^{11}$ is —$N(R^{12})_2$ or morpholinyl. In some embodiments, $R^{11}$ is —$N(R^{12})_2$. In some embodiments, $R^{11}$ is morpholinyl.

In some embodiments, $R^{12}$ is a $C_{1-4}$ alkyl group. In some embodiments, $R^{12}$ is methyl.

In some embodiments, m is 0 or 1. In some embodiments, m is 0. In some embodiments, m is 1.

In some embodiments, the disclosure relates to compounds of formula (I) or formula (IA) that are further defined by formula (II):

(II)

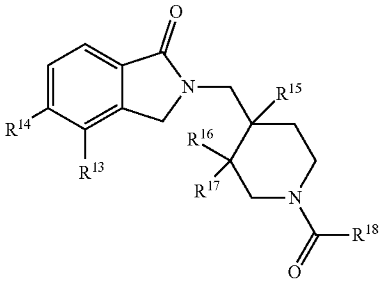

and pharmaceutically acceptable salts, hydrates, solvates, isomers, enantiomers, diastereomers, and tautomers thereof, wherein:

$R^{13}$ is selected from H, halo, $C_{1-4}$ alkyl, $C_{1-4}$ alkoxy, —$C(O)N(R^{19})_2$, or a five-membered heteroaryl ring;

$R^{14}$ is selected from H, $C_{1-4}$ alkyl, and $C(O)N(R^{19})_2$; wherein one of $R^{13}$ and $R^{14}$ must be H;

$R^{15}$ is H or OH;

$R^{16}$ and $R^{17}$ are each a $C_{1-4}$ alkyl group, wherein $R^{16}$ and $R^{17}$ may be joined to one another to form a cycloalkyl that includes the carbon to which they are attached;

$R^{18}$ is selected from alkylcycloalkyl, alkylphenyl, and alkylheteroaryl, each of which may optionally be substituted with one $C_{1-4}$ alkyl; and $R^{19}$ is a $C_{1-4}$ alkyl group.

In some embodiments, compounds of formula (II) have the stereochemistry of formula (II-A):

(II-A)

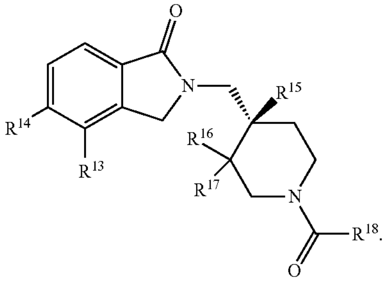

In some embodiments, $R^{13}$ is selected from H, halo, $C_{1-4}$ alkyl, $C_{1-4}$ alkoxy, —$C(O)N(R^{19})_2$, or a five-membered heteroaryl ring. In some embodiments, the disclosure relates to compounds of formula (II) wherein $R^{13}$ is selected from —Cl, methyl, methoxy, —$C(O)N(CH_3)_2$, thiazolyl, pyrazolyl, and oxazolyl. In some embodiments, $R^{13}$ is selected from methyl, methoxy, —$C(O)N(CH_3)_2$, thiazolyl, pyrazolyl, and oxazolyl. In some embodiments, $R^{13}$ is selected from —Cl, methoxy, —$C(O)N(CH_3)_2$, thiazolyl, pyrazolyl, and oxazolyl. In some embodiments, $R^{13}$ is selected from —Cl, methyl, —$C(O)N(CH_3)_2$, thiazolyl, pyrazolyl, and oxazolyl. In some embodiments, $R^{13}$ is selected from —Cl, methyl, methoxy, thiazolyl, pyrazolyl, and oxazolyl. In some embodiments, $R^{13}$ is selected from —Cl, methyl, methoxy, —$C(O)N(CH_3)_2$, pyrazolyl, and oxazolyl. In some embodiments, $R^{13}$ is selected from —Cl, methyl, methoxy, —$C(O)N(CH_3)_2$, thiazolyl, and oxazolyl In some embodiments, $R^{13}$ is selected from —Cl, methyl, methoxy, —$C(O)N(CH_3)_2$, thiazolyl, and pyrazolyl. In some embodiments, $R^{13}$ is —Cl. In some embodiments, $R^{13}$ is methyl. In some embodiments, $R^{13}$ is methoxy. In some embodiments, $R^{13}$ is —$C(O)N(CH_3)_2$. In some embodiments, $R^{13}$ is thiazolyl. In some embodiments, $R^{13}$ is pyrazolyl. In some embodiments, $R^{13}$ is oxazolyl.

In some embodiments, $R^{14}$ is selected from H, $C_{1-4}$ alkyl, and $C(O)N(R^{19})_2$. In some embodiments, the disclosure relates to compounds of formula (II) wherein $R^{14}$ is selected from methyl, and —$C(O)N(CH_3)_2$. In some embodiments, $R^{14}$ is H. In some embodiments, $R^{14}$ is methyl. In some embodiments, $R^{14}$ is —$C(O)N(CH_3)_2$.

$R^{16}$ and $R^{17}$ are each a $C_{1-4}$ alkyl group. In some embodiments, $R^{16}$ and $R^{17}$ are each independently selected from methyl, ethyl, propyl, and butyl. In some embodiments, $R^{16}$ and $R^{17}$ are each independently selected from ethyl, propyl, and butyl. In some embodiments, $R^{16}$ and $R^{17}$ are each independently selected from methyl, propyl, and butyl. In some embodiments, $R^{16}$ and $R^{17}$ are each independently selected from methyl, ethyl, and propyl. In some embodiments, $R^{16}$ and $R^{17}$ are each methyl. In some embodiments, $R^{16}$ and $R^{17}$ are joined to one another to form a cyclopentyl that includes the carbon to which they are attached.

In some embodiments, $R^{18}$ is selected from

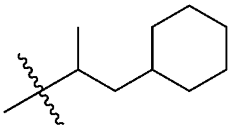 [SMILES: *C(C)CC1CCCCC1]
,
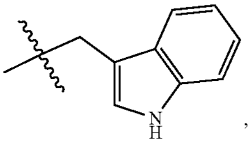
,
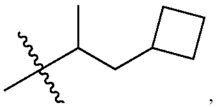
, and
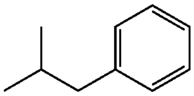
.

In some embodiments, $R^{18}$ is selected from

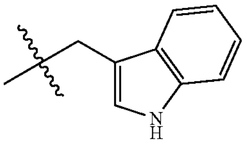
,
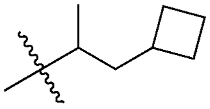
, and
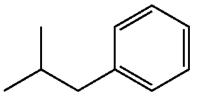
.

In some embodiments, $R^{18}$ is selected from

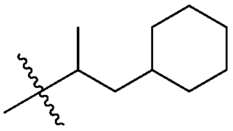
,
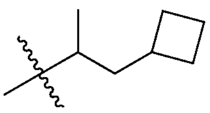
, and

-continued
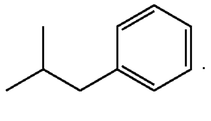
In some embodiments, $R^{18}$ is selected from
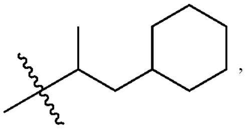
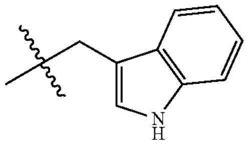
, and
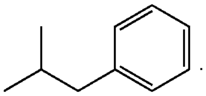
In some embodiments, $R^{18}$ is selected from
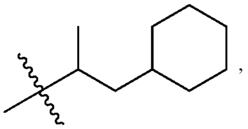
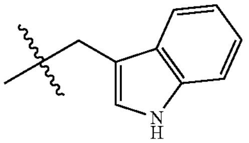
, and
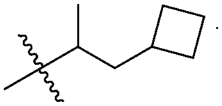
In some embodiments, $R^{18}$ is
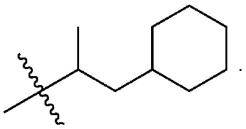 [SMILES: *C(C)CC1CCCCC1]
In some embodiments, $R^{18}$ is
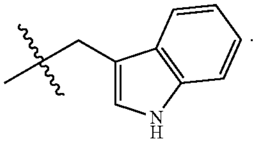 [SMILES: *Cc1c[nH]c2ccccc12]
In some embodiments, $R^{18}$ is
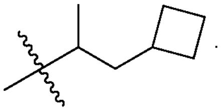 [SMILES: *C(C)CC1CCC1]
In some embodiments, $R^{18}$ is
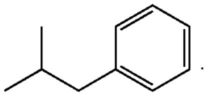
In some embodiments,
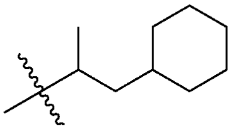 [SMILES: *C(C)CC1CCCCC1]
has the stereochemistry of
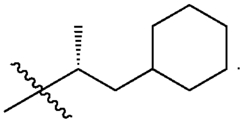 [SMILES: *[C@H](C)CC1CCCCC1]
In some embodiments, a compound of formula (II) is selected from the group consisting of:
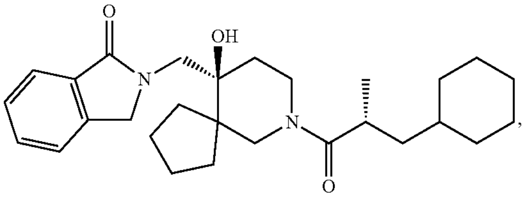
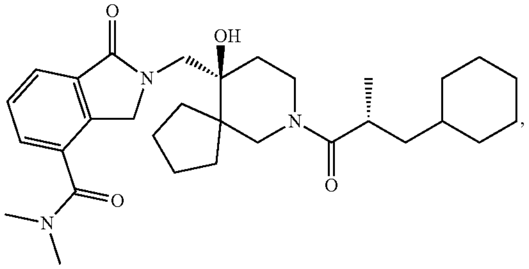
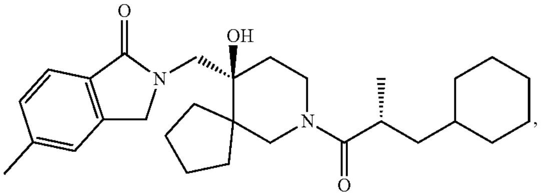
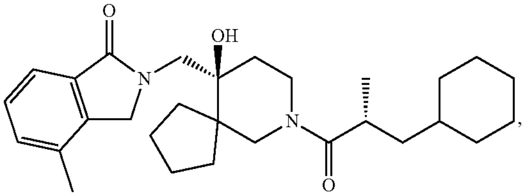

-continued

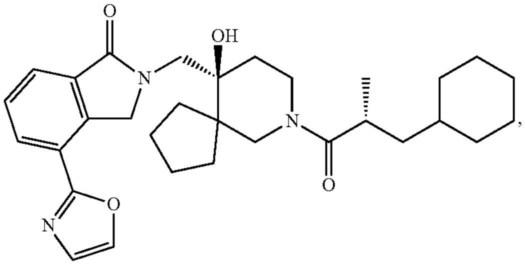
,

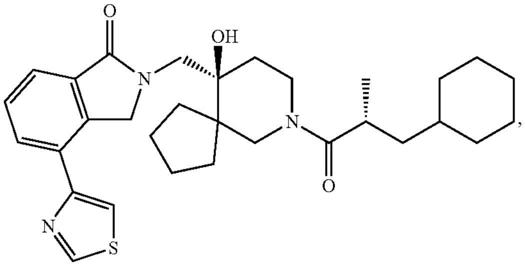
,

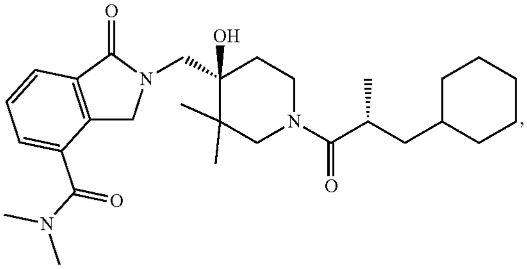
,

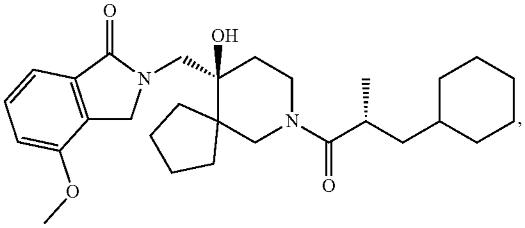
,

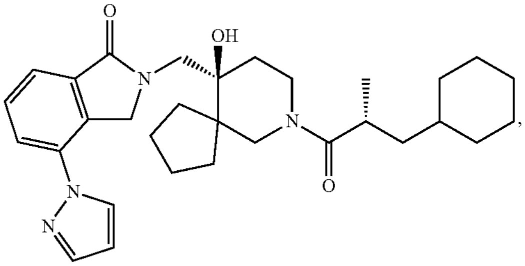
,

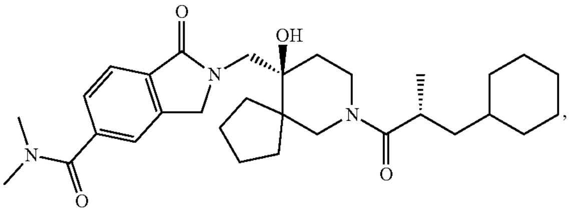
,

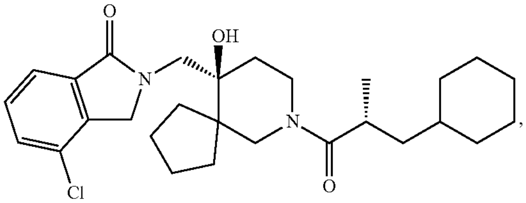
,

-continued

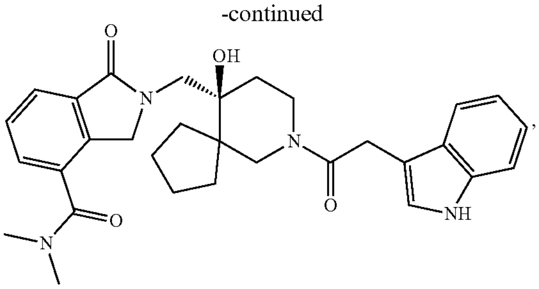
,

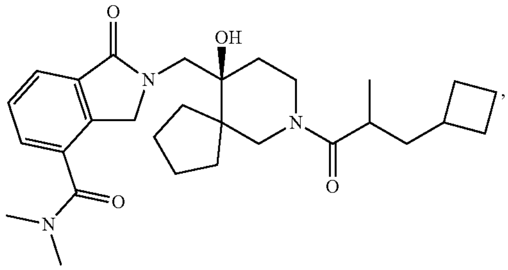
,

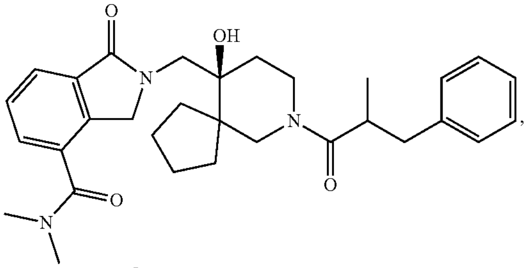
, and

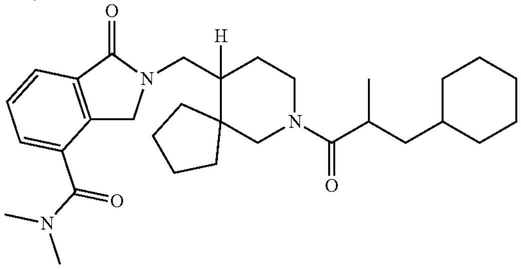
, and enantiomers, diastereomers, and pharmaceutically acceptable salts thereof.

In some embodiments, the disclosure relates to compounds of formula (I) or formula (IA) that are further defined by formula (III):

(III)

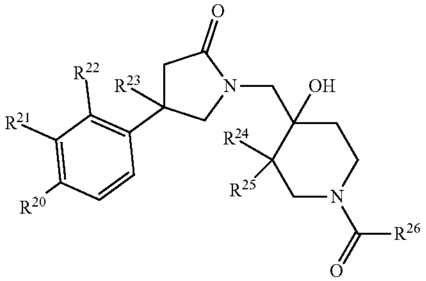

and pharmaceutically acceptable salts, hydrates, solvates, isomers, enantiomers, diastereomers, and tautomers thereof, wherein:

$R^{20}$ is selected from H, halo, and $C_{1-4}$ alkyl;

$R^{21}$ is H or $C_{1-4}$ alkoxy;

$R^{22}$ is H or $C_{1-4}$ alkyl;

wherein two of $R^{20}$, $R^{21}$, and $R^{23}$ must be H;

$R^{23}$ is hydrogen or a $C_{1-4}$ alkyl group;

$R^{24}$ and $R^{25}$ are each a $C_{1-4}$ alkyl group, wherein $R^{24}$ and $R^{25}$ may be joined to one another to form a cycloalkyl that includes the carbon to which they are attached; and $R^{26}$ is an alkylcycloalkyl group substituted with one $C_{1-4}$ alkyl group.

In some embodiments, compounds of formula (III) have the stereochemistry given by formula (III-A):

(III-A)

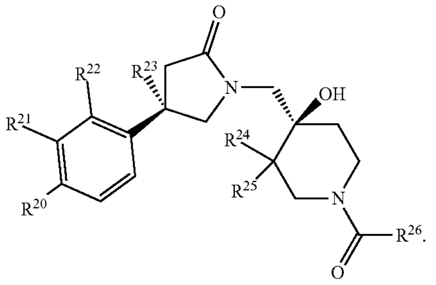

In some embodiments, compounds of formula (III) have the stereochemistry given by formula (III-B):

(III-B)

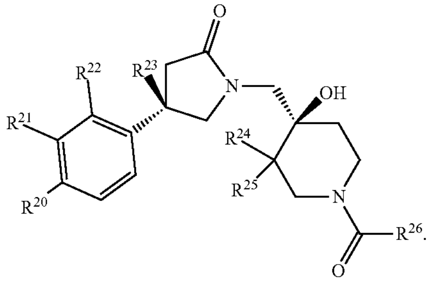

In some embodiments, $R^{20}$ is selected from H, halo, and $C_{1-4}$ alkyl. In some embodiments, $R^{20}$ is selected from H, Cl, and methyl. In some embodiments, the disclosure relates to compounds of formula (III) wherein $R^{20}$ is selected from —Cl and methyl. In some embodiments, $R^{20}$ is H or methyl. In some embodiments, $R^{20}$ is H or Cl. In some embodiments, $R^{20}$ is H. In some embodiments, $R^{20}$ is methyl. In some embodiments, $R^{20}$ is Cl.

In some embodiments, $R^{21}$ is H or $C_{1-4}$ alkoxy. In some embodiments, $R^{21}$ is H or methoxy. In some embodiments, $R^{21}$ is H. In some embodiments, the disclosure relates to compounds of formula (III) wherein $R^{21}$ is methoxy.

In some embodiments, $R^{22}$ is H or $C_{1-4}$ alkyl. In some embodiments, $R^{22}$ is H or methyl. In some embodiment, $R^{22}$ is H. In some embodiments, the disclosure relates to compounds of formula (III) wherein $R^{22}$ is methyl.

In some embodiments, $R^{23}$ is H or a $C_{1-4}$ alkyl group. In some embodiments, $R^{23}$ is H or methyl. In some embodiments, $R^{23}$ is H. In some embodiments, the disclosure relates to compounds of formula (III) wherein $R^{23}$ is methyl.

In some embodiments, $R^{24}$ and $R^{25}$ are each a $C_{1-4}$ alkyl group. In some embodiments, $R^{24}$ and $R^{25}$ are each independently methyl, ethyl, propyl, or butyl. In some embodiments, $R^{24}$ and $R^{25}$ are each independently ethyl, propyl, or butyl. In some embodiments, $R^{24}$ and $R^{25}$ are each independently methyl, propyl, or butyl. In some embodiments, $R^{24}$ and $R^{25}$ are each independently methyl, ethyl, or butyl. In some embodiments, $R^{24}$ and $R^{25}$ are each independently methyl, ethyl, or propyl. In some embodiments, $R^{24}$ and $R^{25}$ are each methyl. In some embodiments, the disclosure relates to compounds of formula (III) wherein $R^{24}$ and $R^{25}$ are joined to one another to form a cyclopentyl that includes the carbon to which they are attached.

In some embodiments, the disclosure relates to compounds of formula (III) wherein $R^{26}$ is

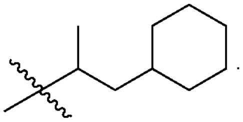 [SMILES: *C(C)CC1CCCCC1]

In some embodiments, the disclosure relates to compounds of formula (III) wherein $R^{26}$ is

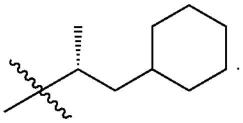 [SMILES: *[C@H](C)CC1CCCCC1]

In some embodiments, a compound of formula (III) is selected from the group consisting of:

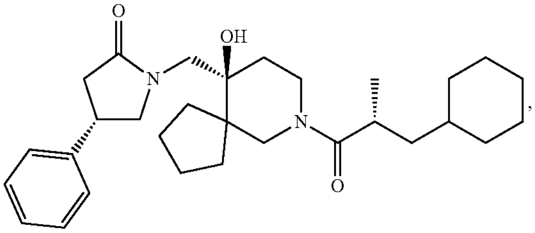

,

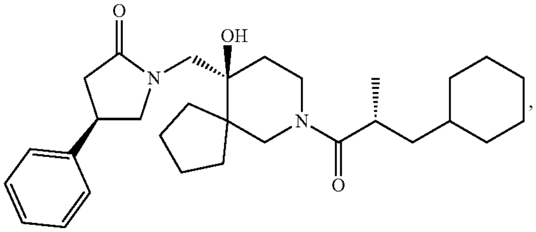

,

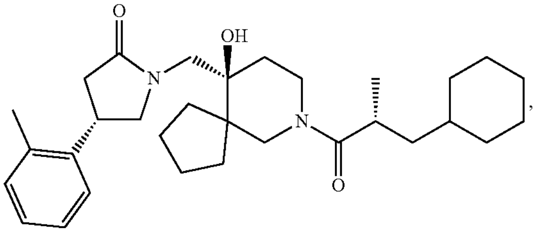

,

-continued

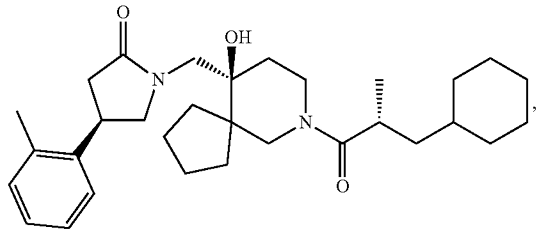
,

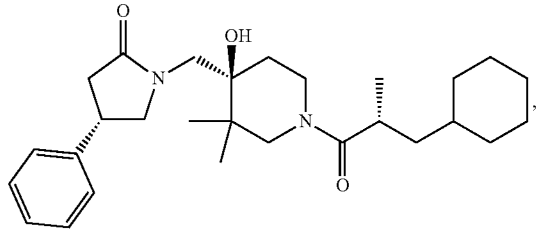
,

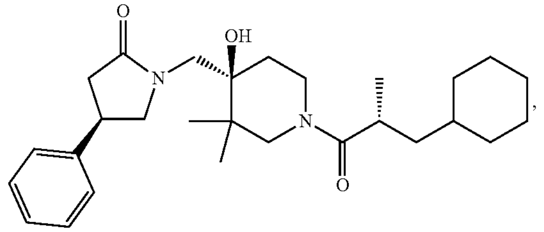
,

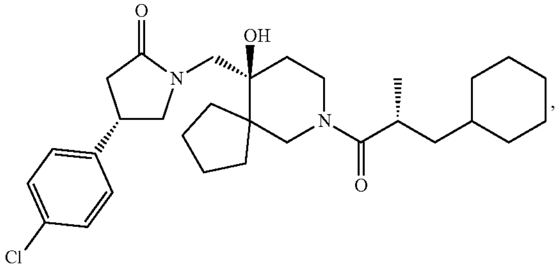
,

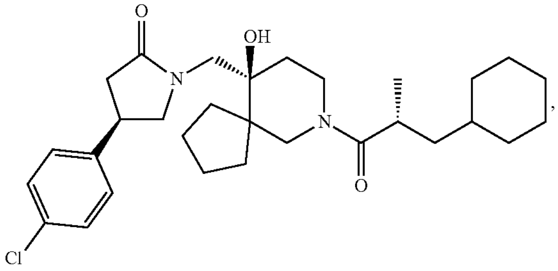
,

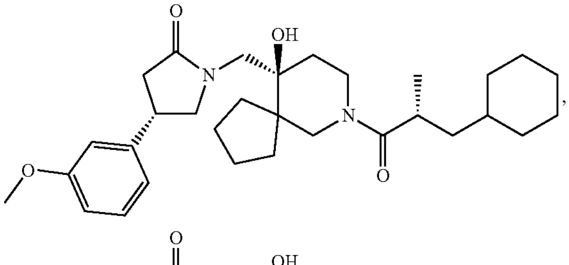
,

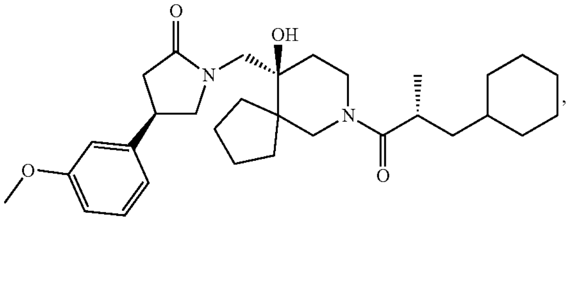
,

-continued

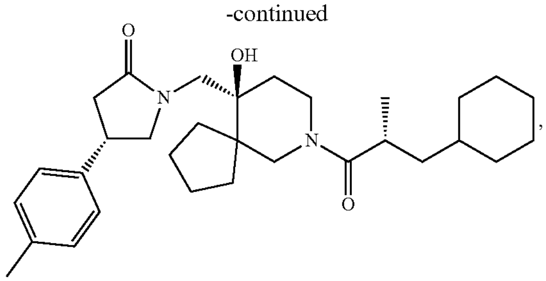
,

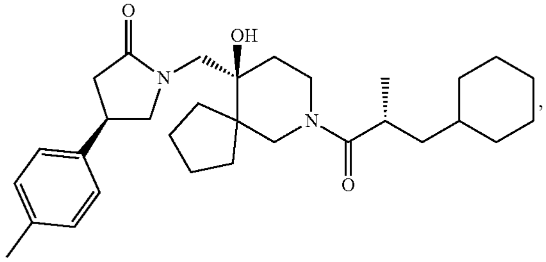
,

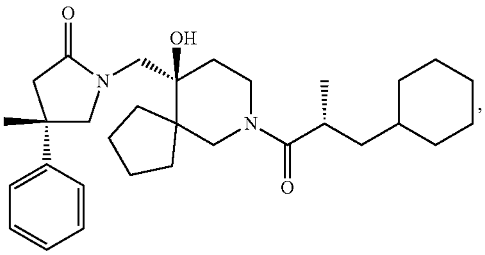
, and

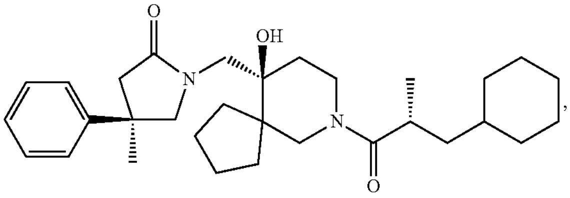
, and enantiomers, diastereomers, and pharmaceutically acceptable salts thereof.

In some embodiments, the disclosure relates to compounds of formula (I) or formula (IA) that are further defined by formula (IV):

(IV)

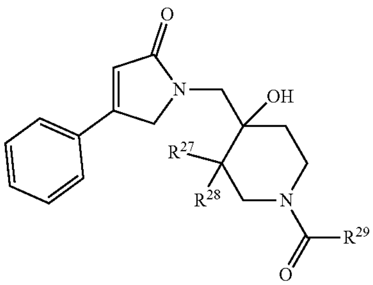

and pharmaceutically acceptable salts, hydrates, solvates, isomers, enantiomers, diastereomers, and tautomers thereof, wherein:

$R^{27}$ and $R^{28}$ are each a $C_{1-4}$ alkyl group, wherein $R^{27}$ and $R^{28}$ may be joined to one another to form a cycloalkyl that includes the carbon to which they are attached; and $R^{29}$ is an alkylcycloalkyl group substituted with one $C_{1-4}$ alkyl group.

In some embodiments, compounds of formula (IV) have the stereochemistry given by formula (IV-A):

(IV-A)

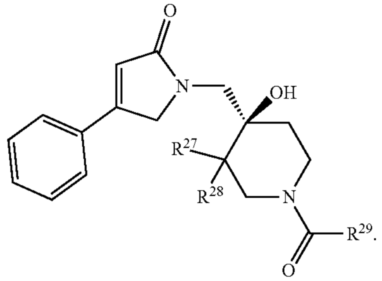

In some embodiments, $R^{27}$ and $R^{28}$ are each a $C_{1-4}$ alkyl group. In some embodiments, $R^{27}$ and $R^{28}$ are each independently methyl, ethyl, propyl, or butyl. In some embodiments, $R^{27}$ and $R^{28}$ are each independently ethyl, propyl, or butyl. In some embodiments, $R^{27}$ and $R^{28}$ are each independently methyl, propyl, or butyl. In some embodiments, $R^{27}$ and $R^{28}$ are each independently methyl, ethyl, or butyl. In some embodiments, $R^{27}$ and $R^{28}$ are each independently methyl, ethyl, or propyl. In some embodiments, the disclosure relates to compounds of formula (IV) wherein $R^{27}$ and $R^{28}$ are joined to one another to form a cyclopentyl that includes the carbon to which they are attached.

In some embodiments, the disclosure relates to compounds of formula (III) wherein $R^{29}$ is

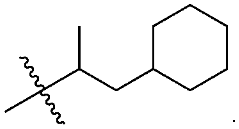

.

In some embodiments, the disclosure relates to compounds of formula (IV) wherein $R^{29}$ is

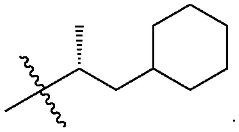 [SMILES: *[C@H](C)CC1CCCCC1]

.

In some embodiments, a compound of formula (IV) is:

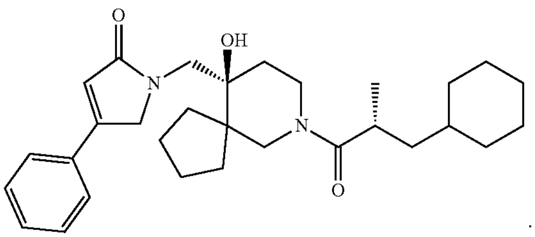 [SMILES: C[C@H](CC1CCCCC1)C(=O)N1CC[C@@](O)(CN2CC(c3ccccc3)=CC2=O)C2(CCCC2)C1]

.

In some embodiments, the disclosure relates to compounds of formula (I) or formula (IA) that are further defined by formula (V):

(V)

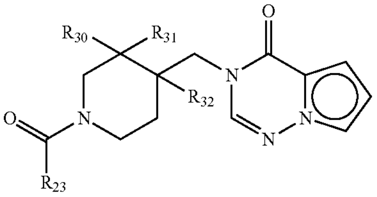

and pharmaceutically acceptable salts, hydrates, solvates, isomers, enantiomers, diastereomers, and tautomers thereof, wherein:

$R^{30}$ and $R^{31}$ are H or $C_{1-4}$ alkyl, wherein $R^{30}$ and $R^{31}$ may be joined to one another to form a cycloalkyl that includes the carbon to which they are attached;

$R^{32}$ is selected from: —OH, $C_{1-4}$ alkoxy, and halogen; and $R^{33}$ is an alkylcycloalkyl or alkylheteroaryl group substituted with one $C_{1-4}$ alkyl group.

In some embodiments, compounds of formula (V) have the stereochemistry of formula (V-A):

(V-A)

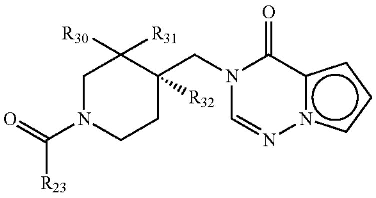

.

In some embodiments, compounds of formula (V) have the stereochemistry of formula (V-B):

(V-B)

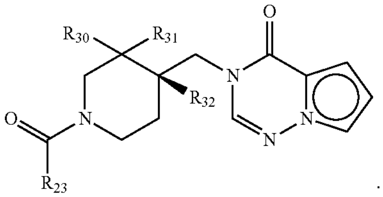

.

In some embodiments, $R^{30}$ and $R^{31}$ H or $C_{1-4}$ alkyl. In some embodiments, $R^{30}$ and $R^{31}$ are each a $C_{1-4}$ alkyl group. In some embodiments, $R^{30}$ and $R^{31}$ are each independently methyl, ethyl, propyl, or butyl. In some embodiments, $R^{30}$ and $R^{31}$ are each independently ethyl, propyl, or butyl. In some embodiments, $R^{30}$ and $R^{31}$ are each independently methyl, propyl, or butyl. In some embodiments, $R^{30}$ and $R^{31}$ are each independently methyl, ethyl, or butyl. In some embodiments, $R^{30}$ and $R^{31}$ are each independently methyl, ethyl, or propyl. In some embodiments, the disclosure relates to compounds of formula (V) wherein $R^{30}$ and $R^{31}$ are joined to one another to form a cyclopentyl that includes the carbon to which they are attached. In some embodiments, the disclosure relates to compounds of formula (V) wherein $R^{30}$ and $R^{31}$ are each H.

In some embodiments, $R^{32}$ is selected from: —OH, $C_{1-4}$ alkoxy, and halogen. In some embodiments, $R^{32}$ is selected from: —OH, methoxy, and F. In some embodiments, the disclosure relates to compounds of formula (V) wherein $R^{32}$ is methoxy or —F. In some embodiments $R^{32}$ is —OH or methoxy. In some embodiments, $R^{32}$ is —OH or F. In some embodiments, $R^{32}$ is —OH. In some embodiments, $R^{32}$ is methoxy. In some embodiments, $R^{32}$ is F.

In some embodiments, the disclosure relates to compounds of formula (III) wherein $R^{33}$ is

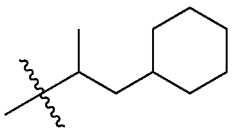
or
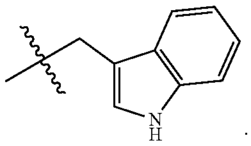 [SMILES: *Cc1c[nH]c2ccccc12]
.

In some embodiments, $R^{33}$ is

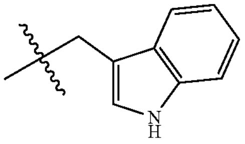
.

In some embodiments, $R^{33}$ is

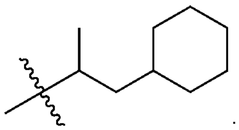 [SMILES: *C(C)CC1CCCCC1]
.

In some embodiments,

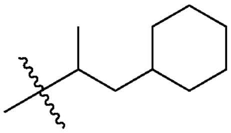 [SMILES: *C(C)CC1CCCCC1]

has the stereochemistry of

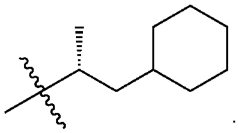 [SMILES: *[C@H](C)CC1CCCCC1]
.

In some embodiments, a compound of formula (V) is selected from the group consisting of:

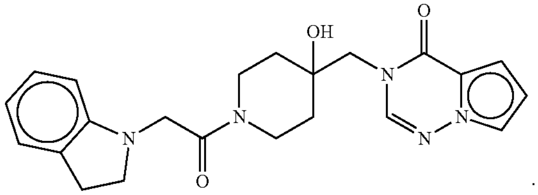
.

-continued

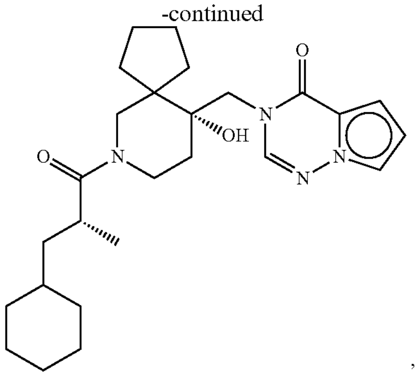
,

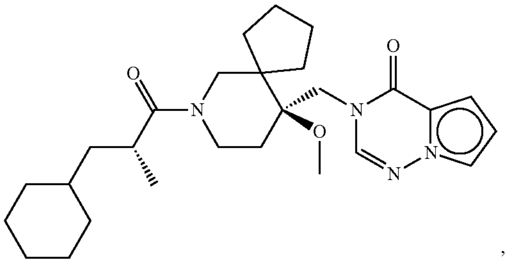
, and

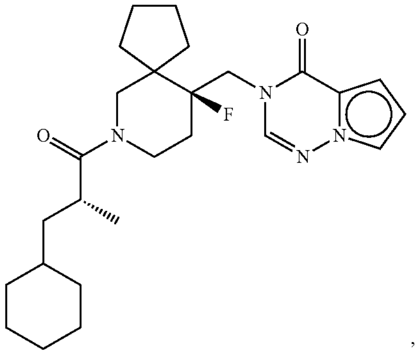
, and enantiomers, diastereomers, and pharmaceutically acceptable salts thereof.

In some embodiments, the disclosure relates to compounds of formula (I) or formula (IA) that are further defined by formula (VI):

(VI)

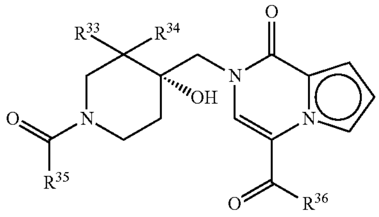

and pharmaceutically acceptable salts, hydrates, solvates, isomers, enantiomers, diastereomers, and tautomers thereof, wherein:

$R^{33}$ and $R^{34}$ are each a $C_{1-4}$ alkyl group, wherein $R^{33}$ and $R^{34}$ may be joined to one another to form a cycloalkyl that includes the carbon to which they are attached;

$R^{35}$ is an alkylcycloalkyl group substituted with one $C_{1-4}$ alkyl group;

$R^{36}$ is —$N(R^{37})_2$ or a 5 to 6-membered heterocycle containing two heteroatoms selected from N and O; and $R^{37}$ is a $C_{1-4}$ alkyl group.

In some embodiments, $R^{33}$ and $R^{34}$ are each independently H or $C_{1-4}$ alkyl. In some embodiments, $R^{33}$ and $R^{34}$ are each a $C_{1-4}$ alkyl group. In some embodiments, $R^{33}$ and $R^{34}$ are each independently methyl, ethyl, propyl, or butyl. In some embodiments, $R^{33}$ and $R^{34}$ are each independently ethyl, propyl, or butyl. In some embodiments, $R^{33}$ and $R^{34}$ are each independently methyl, propyl, or butyl. In some embodiments, $R^{33}$ and $R^{34}$ are each independently methyl, ethyl, or butyl. In some embodiments, $R^{33}$ and $R^{34}$ are each independently methyl, ethyl, or propyl. In some embodiments, the disclosure relates to compounds of formula (VI) wherein $R^{33}$ and $R^{34}$ are joined to one another to form a cyclopentyl that includes the carbon to which they are attached.

In some embodiments, the disclosure relates to compounds of formula (VI) wherein $R^{35}$ is

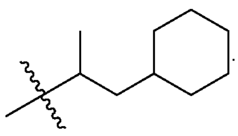 [SMILES: *C(C)CC1CCCCC1]

In some embodiments, the disclosure relates to compounds of formula (VI) wherein $R^{35}$ is

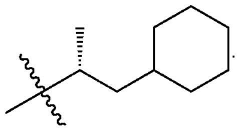 [SMILES: *[C@H](C)CC1CCCCC1]

In some embodiments, $R^{36}$ is —$N(R^{37})_2$ or a 5 to 6-membered heterocycle containing two heteroatoms selected from N and O. In some embodiments, $R^{36}$ is —$N(R^{37})_2$ or a 6-membered heterocycle containing two heteroatoms selected from N and O. In some embodiments, $R^{36}$ is —$N(R^{37})_2$. In some embodiments, $R^{36}$ is a 6-membered heterocycle containing two heteroatoms selected from N and O. In some embodiments, $R^{36}$ is —$N(R^{37})_2$ or morpholinyl. In some embodiments, the disclosure relates to compounds of formula (VI) wherein $R^{36}$ is morpholinyl.

In some embodiments, the disclosure relates to compounds of formula (VI) wherein $R^{37}$ is methyl.

In some embodiments, a compound of formula (VI) is selected from the group consisting of:

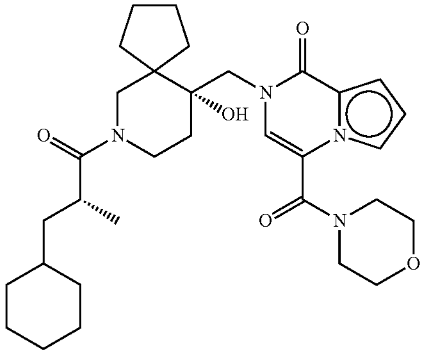

and

-continued

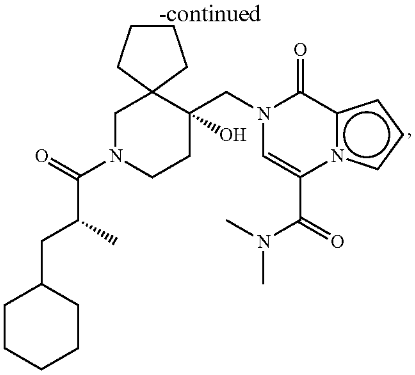

, and enantiomers, diastereomers, and pharmaceutically acceptable salts thereof.

Non-limiting, specific embodiments of the USP19 inhibitor compounds are shown in Table B below.

Methods of Preparing the Compounds of the Disclosure

The compounds of the present disclosure may be made by a variety of methods, including standard chemistry. Suitable synthetic routes are depicted in the examples given below.

The compounds of the present disclosure, i.e., compounds of formulas (I)-(VI) or a pharmaceutically acceptable salt thereof, may be prepared by methods known in the art of organic synthesis as set forth in part by the synthetic schemes depicted in the examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formulas (I)-(VI).

Those skilled in the art will recognize stereocenters exist in the compounds of Formula (I)-(VI). Accordingly, the present disclosure includes both possible stereoisomers (unless otherwise indicated and/or specified in the synthesis) and includes not only racemic compounds but the individual enantiomers and/or diastereomers as well. Unless otherwise indicated, when a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Compounds of Formulas (I)-(VI) may specifically be made by methods known in the art including those described below and including variations within the skill of the art. Some reagents and intermediates are known in the art. Other reagents and intermediates can be made by methods known in the art using readily available materials. The formula and variable designations used to describe the syntheses of the compounds are not to be confused with variables used in the claims or in the other sections of the specification. The follow methods are for illustrative purposes only and are not intended to limit the scope of the invention. The schemes encompass reasonable variations known in the art.

Isoindolinones of formula (II) can be prepared in a number of different ways. Scheme 1 illustrates the preparation of isoinodolinone-piperidinol analogs of formula (II-1). In this method, variously substituted isoindolinones (1) are treated with substituted tert-butyl 1-oxa-6-azaspiro[2.5]octane-6-carboxylates (2) (available in two routine steps from their corresponding ketones) in the presence of a base, such as cesium carbonate or N,N-diisopropylethyamine, in a high boiling, dipolar, aprotic solvent, such as dimethylformamide or N,N-dimethylacetamide, with external heating to afford the corresponding N-alkyl isoindolinones (3). The tert-butyloxycarbonyl group present on the N-alkyl isoindolinones (3) can be removed upon treatment with a strong acid, such as trifluoroacetic acid in dichloromethane or hydrochloric acid in dioxane, to provide the N—H piperidinols (4). Coupling of the N—H piperidinols 4 with variously substituted carboxylic acids (5) under standard conditions used for amide bond formation, such as HATU and diisopropylethylamine in N,N-dimethylformamide, can afford the compounds of formula (II-1). Diastereomers and/or enantiomers of the final products can be separated using high-pressure liquid chromatography and/or super critical fluid chromatography (SFC) methods that employ commercially available chiral stationary phases known in the art.

Isoindolinones of formula (II-2) can be readily prepared from compounds of formula (II-1) as illustrated in Scheme 2. Dehydration of the compounds of formula (II-1) using trimethylsilylchloride and triethylamine provides the mixture of tri-substituted alkenes (6). Reduction of the exocyclic olefin mixtures (6) using catalytic palladium on carbon under a hydrogen atmosphere affords the reduced products (7). The tert-butyloxycarbonyl group present on the N-alkyl isoindolinones (7) can be removed upon treatment with a strong acid, such as trifluoroacetic acid in dichloromethane or hydrochloric acid in dioxane, to provide the N—H piperidinols (8). Coupling of the N—H piperidinols (8) with variously substituted carboxylic acids (5) under standard conditions used for amide bond formation, such as HATU and diisopropylethylamine in N,N-dimethylformamide, can afford the compounds of formula (II-2). Diastereomers and/or enantiomers of the final products can be separated using high pressure liquid chromatography and/or super critical fluid chromatography (SFC) methods that employ commercially available chiral stationary phases known in the art.

Scheme 1

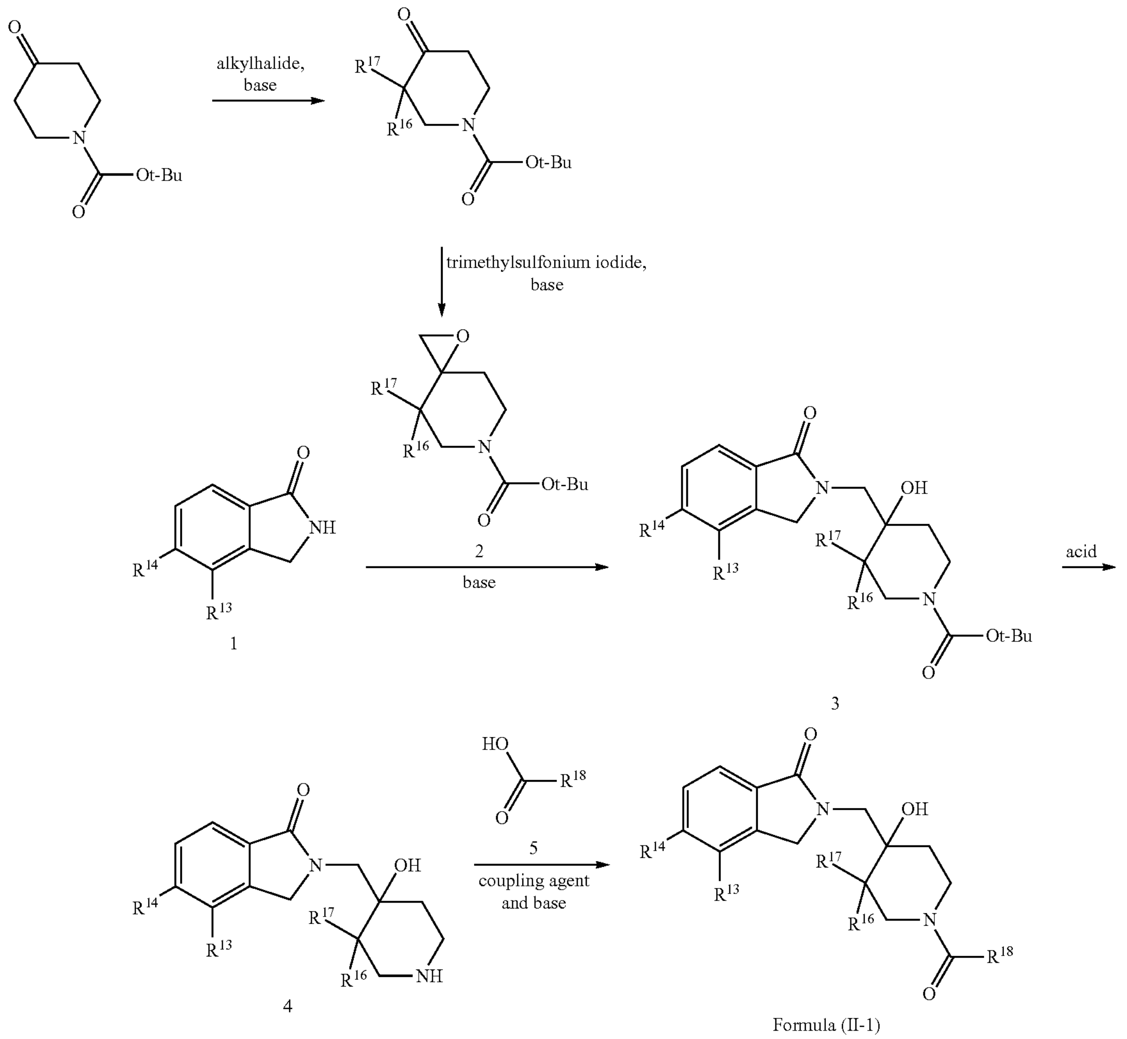

1

2

3

4

5

Formula (II-1)

Scheme 2

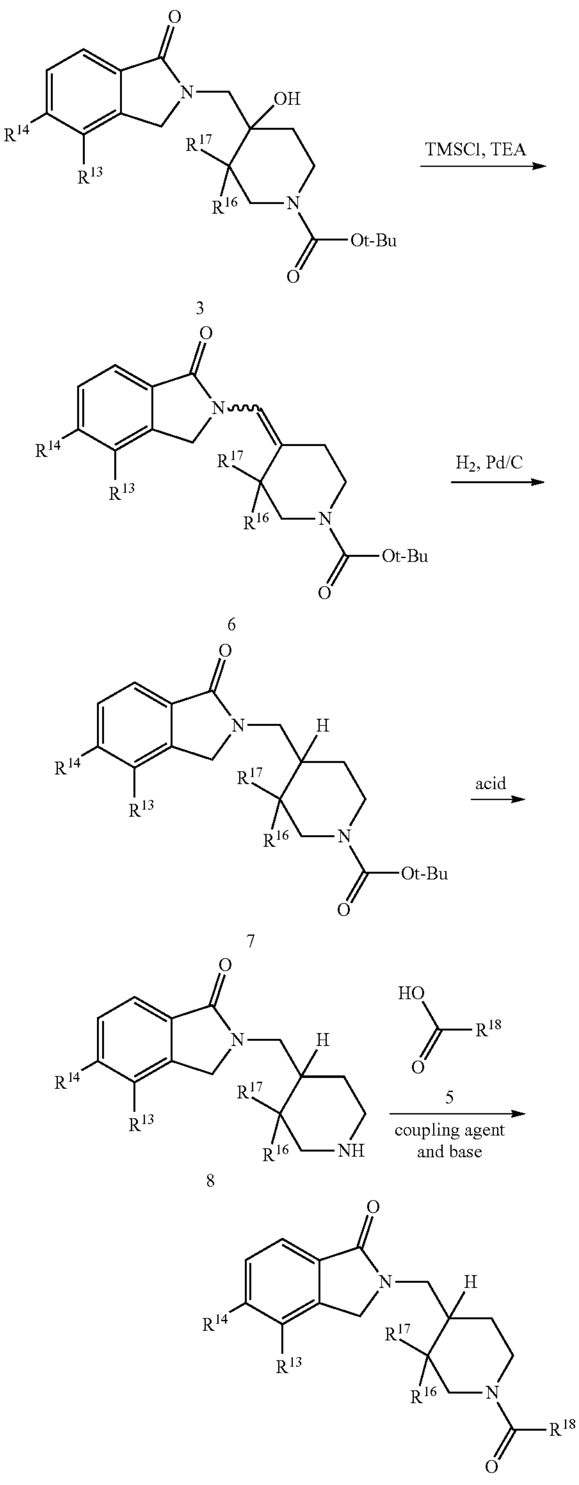

3

6

7

8

5

Formula (II-2)

Phenyl lactams of formula (III) can be prepared in a number of different ways. Scheme 3 illustrates one such method for preparing compounds of formula (III). In this method, variously substituted phenyl lactams (9) are treated with substituted tert-butyl 1-oxa-6-azaspiro[2.5]octane-6-carboxylates (2) in the presence of a base, such as cesium carbonate or N,N-diisopropylethyamine, in a high boiling, dipolar, aprotic solvent, such as dimethylformamide or N,N-dimethylacetamide, with external heating to afford the corresponding N-alkyl isoindolinones (10). The tert-butyloxycarbonyl group present on the N-alkyl isoindolinones (10) can be removed upon treatment with a strong acid, such as trifluoroacetic acid in dichloromethane or hydrochloric acid in dioxane, to provide the N—H piperidinols (11). Coupling of the N—H piperidinols (11) with variously substituted carboxylic acids (5) under standard conditions used for amide bond formation, such as HATU and diisopropylethylamine in N,N-dimethylformamide, can afford the compounds of formula (III). Diastereomers and/or enantiomers of the final products can be separated using high pressure liquid chromatography and/or super critical fluid chromatography (SFC) methods that employ commercially available chiral stationary phases known in the art. Compounds of formula (IV) and their individual diasteromers can be prepared from variously substituted 4-phenyl-1,5-dihydro-2H-pyrrol-2-ones in analogous fashion.

Scheme 3

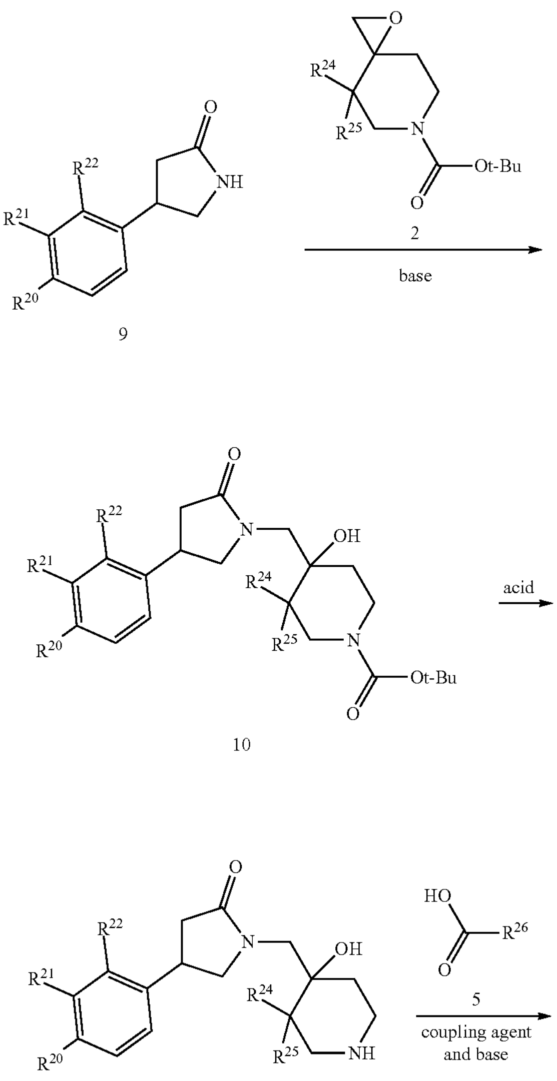

2

9

10

5

11

-continued

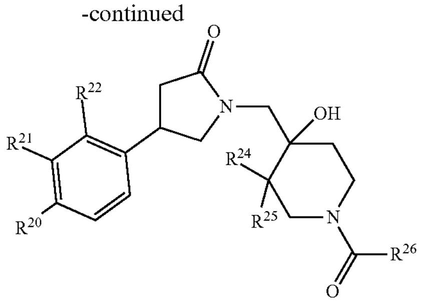

Formula III

Pharmaceutical Compositions of the Compounds of the Disclosure

The present disclosure also relates to pharmaceutical compositions that include a compound of any one of formulas (I)-(VI) for use in medicine. The pharmaceutical compositions of a compound of any one of formulas (I)-(VI) disclosed herein are useful for methods of modulating USP19. The pharmaceutical compositions of a compound of any one of formulas (I)-(VI) disclosed herein are also useful for methods of inhibiting USP19.

USP19 Inhibitor Compounds are useful in the development of pharmaceutical compositions suitable for the enhancement of muscle growth following injury or muscle wasting disease, protection from the deleterious consequences of obesity and diabetes, treatment of neurodegenerative diseases including Parkinson's disease or Alzheimer's disease, and the treatment of various cancers, including Ewing sarcoma.

The compounds of formulas (I)-(VI) may form acid addition salts, which may be pharmaceutically acceptable salts.

The disclosure also includes pharmaceutical compositions comprising one or more compounds as described herein, or a pharmaceutically acceptable salt thereof, and a pharmaceutically acceptable carrier. In some embodiments, pharmaceutical compositions reported herein can be provided in a unit dosage form (e.g., capsule, tablet or the like). In some embodiments, pharmaceutical compositions reported herein can be provided in an oral dosage form. In some embodiments, an oral dosage form of a compound of any one of formulas (I)-(VI) can be a capsule. In some embodiments, an oral dosage form of a compound of any one of formulas (I)-(VI) is a tablet. In some embodiments, an oral dosage form comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation.

Compositions in accordance with the present invention may be employed for administration in any appropriate manner, e.g., oral or buccal administration. When orally administered, the compound of formula I may be prepared as a mixture with excipients suitable for the manufacture of oral dosage forms such as tablets, in a solution or suspension, in hard or soft encapsulated form including gelatin encapsulated form, sachet, or lozenge. Suspensions for oral administration may be prepared according to any method known to those skilled in the art. For example, suspensions may be oily suspensions in which a compound of any one of formulas (I)-(VI) is suspended in a liquid suspension comprising, for example, vegetable oils such as olive oil, sesame oil, or coconut oil. The liquid suspension may also contain mineral oil.

Compositions may also be administered topically, e.g., for application to the skin, for example in the form of a cream, paste, lotion, gel, ointment, poultice, cataplasm, plaster, dermal patch or the like, or for ophthalmic application, for example in the form of an eye drop, -lotion or -gel formulation.

Compositions may also be administered parenterally, e.g., intravenous. Intravenous forms include, but are not limited to, bolus and drip injections. In some embodiments, the intravenous dosage forms are sterile or capable of being sterilized prior to administration to a subject since they typically bypass the subject's natural defenses against contaminants. Examples of intravenous dosage forms include, but are not limited to, Water for Injection USP; aqueous vehicles including, but not limited to, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol and polypropylene glycol; and non-aqueous vehicles including, but not limited to, corn oil, cottonseed oil, peanut oil, sesame oil, ethyl oleate, isopropyl myristate and benzyl benzoate.

Readily flowable forms, for example solutions, emulsions and suspensions, may also be employed e.g., for intralesional injection, or may be administered rectally, e.g., as an enema or suppository, or intranasal administration, e.g., as a nasal spray or aerosol. Macrocrystalline powders may be formulated for inhalation, e.g., delivery to the nose, sinus, throat or lungs. Transdermal compositions/devices and pessaries may also be employed for delivery of the compounds of the invention. The compositions may additionally contain agents that enhance the delivery of the compounds having any one of formulas (I)-(VI) (or other active agents), e.g., liposomes, polymers or co-polymers (e.g., branched chain polymers).

The pharmaceutical compositions of the present invention may further comprise one or more additives. Additives that are well known in the art include, e.g., detackifiers, anti-foaming agents, buffering agents, antioxidants (e.g., ascorbic acid, ascorbyl palmitate, sodium ascorbate, butylated hydroxyanisole (BHA), butylated hydroxytoluene (BHT), propyl gallate, malic acid, fumaric acid, potassium metabisulfite, sodium bisulfite, sodium metabisulfite, and tocopherols, e.g., α-tocopherol (vitamin E)), preservatives, chelating agents, viscomodulators, tonicifiers, flavorants, colorants, odorants, opacifiers, suspending agents, binders, fillers, plasticizers, lubricants, and mixtures thereof. The amounts of such additives can be readily determined by one skilled in the art, according to the particular properties desired, and can be formulated such that compounds having Formula I are stable, e.g., not reduced by antioxidant additives.

The additive may also comprise a thickening agent. Suitable thickening agents may be of those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkylcelluloses such as hydroxypropyl-methyl-celluloses; acylated celluloses, e.g., cellulose-acetates, cellulose-acetatephthallates, cellulose-acetatesuccinates and hydroxypropyl ethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products.

Such thickening agents as described above may be included, e.g., to provide a sustained release effect. However, where oral administration is intended, the use of thickening agents may not be required. Use of thickening agents is, on the other hand, indicated, e.g., where topical application is foreseen.

Pharmaceutical compositions of a compound of formula (I), as described herein, or a pharmaceutically acceptable salt, hydrate, solvate, isomer, enantiomer, diastereomer, or tautomer thereof, and one or more of a pharmaceutically acceptable carrier, adjuvant, or vehicle are disclosed.

In some embodiments, the pharmaceutical compositions include a compound of formula (I) and one or more of a pharmaceutically acceptable carrier, adjuvant, or vehicle. In some embodiments, the pharmaceutical compositions include a compound of formula (I) and one or more of a pharmaceutically acceptable carrier or vehicle. In some embodiments, the pharmaceutical compositions include a compound of formula (I) and one or more of a pharmaceutically acceptable carrier. In some embodiments, the pharmaceutical compositions include a compound of formula (I) and one or more of a pharmaceutically acceptable vehicle.

In some embodiments, the pharmaceutical compositions include a pharmaceutically acceptable salt of a compound of formula (I) and one or more of a pharmaceutically acceptable carrier, adjuvant, or vehicle. In some embodiments, the pharmaceutical compositions include a pharmaceutically acceptable salt of a compound of formula (I) and one or more of a pharmaceutically acceptable carrier or vehicle. In some embodiments, the pharmaceutical compositions include a pharmaceutically acceptable salt of a compound of formula (I) and one or more of a pharmaceutically acceptable carrier. In some embodiments, the pharmaceutical compositions include a pharmaceutically acceptable salt of a compound of formula (I) and one or more of a pharmaceutically acceptable vehicle.

In some embodiments, the pharmaceutical compositions include a compound of formula (I) that is further given by formula (IA), as described herein, or a pharmaceutically acceptable salt, hydrate, solvate, isomer, enantiomer, diastereomer, or tautomer thereof, and one or more of a pharmaceutically acceptable carrier, adjuvant, or vehicle.

In some embodiments, the pharmaceutical compositions include a compound of formula (IA) and one or more of a pharmaceutically acceptable carrier, adjuvant, or vehicle. In some embodiments, the pharmaceutical compositions include a compound of formula (IA) and one or more of a pharmaceutically acceptable carrier or vehicle. In some embodiments, the pharmaceutical compositions include a compound of formula (IA) and one or more of a pharmaceutically acceptable carrier. In some embodiments, the pharmaceutical compositions include a compound of formula (IA) and one or more of a pharmaceutically acceptable vehicle.

In some embodiments, the pharmaceutical compositions include a pharmaceutically acceptable salt of a compound of formula (IA) and one or more of a pharmaceutically acceptable carrier, adjuvant, or vehicle. In some embodiments, the pharmaceutical compositions include a pharmaceutically acceptable salt of a compound of formula (IA) and one or more of a pharmaceutically acceptable carrier or vehicle. In some embodiments, the pharmaceutical compositions include a pharmaceutically acceptable salt of a compound of formula (IA) and one or more of a pharmaceutically acceptable carrier. In some embodiments, the pharmaceutical compositions include a pharmaceutically acceptable salt of a compound of formula (IA) and one or more of a pharmaceutically acceptable vehicle.

In some embodiments, the pharmaceutical compositions include a compound of formula (I) or formula (IA) that is further given by formula (II), as described herein, or a pharmaceutically acceptable salt, hydrate, solvate, isomer, enantiomer, diastereomer, or tautomer thereof, and one or more of a pharmaceutically acceptable carrier, adjuvant, or vehicle.

In some embodiments, the pharmaceutical compositions include a compound of formula (II) and one or more of a pharmaceutically acceptable carrier, adjuvant, or vehicle. In some embodiments, the pharmaceutical compositions include a compound of formula (II) and one or more of a pharmaceutically acceptable carrier or vehicle. In some embodiments, the pharmaceutical compositions include a compound of formula (II) and one or more of a pharmaceutically acceptable carrier. In some embodiments, the pharmaceutical compositions include a compound of formula (II) and one or more of a pharmaceutically acceptable vehicle.

In some embodiments, the pharmaceutical compositions include a pharmaceutically acceptable salt of a compound of formula (II) and one or more of a pharmaceutically acceptable carrier, adjuvant, or vehicle. In some embodiments, the pharmaceutical compositions include a pharmaceutically acceptable salt of a compound of formula (II) and one or more of a pharmaceutically acceptable carrier or vehicle. In some embodiments, the pharmaceutical compositions include a pharmaceutically acceptable salt of a compound of formula (II) and one or more of a pharmaceutically acceptable carrier. In some embodiments, the pharmaceutical compositions include a pharmaceutically acceptable salt of a compound of formula (II) and one or more of a pharmaceutically acceptable vehicle.

Pharmaceutical compositions of a compound of formula (I) or formula (IA) that is further given by formula (III), as described herein, or a pharmaceutically acceptable salt, hydrate, solvate, isomer, enantiomer, diastereomer, or tautomer thereof, and one or more of a pharmaceutically acceptable carrier, adjuvant, or vehicle are disclosed.

In some embodiments, the pharmaceutical compositions include a compound of formula (III) and one or more of a pharmaceutically acceptable carrier, adjuvant, or vehicle. In some embodiments, the pharmaceutical compositions include a compound of formula (III) and one or more of a pharmaceutically acceptable carrier or vehicle. In some embodiments, the pharmaceutical compositions include a compound of formula (III) and one or more of a pharmaceutically acceptable carrier. In some embodiments, the pharmaceutical compositions include a compound of formula (III) and one or more of a pharmaceutically acceptable vehicle.

In some embodiments, the pharmaceutical compositions include a pharmaceutically acceptable salt of a compound of formula (III) and one or more of a pharmaceutically acceptable carrier, adjuvant, or vehicle. In some embodiments, the pharmaceutical compositions include a pharmaceutically acceptable salt of a compound of formula (III) and one or more of a pharmaceutically acceptable carrier or vehicle. In some embodiments, the pharmaceutical compositions include a pharmaceutically acceptable salt of a compound of formula (III) and one or more of a pharmaceutically acceptable carrier. In some embodiments, the pharmaceutical compositions include a pharmaceutically acceptable salt of a compound of formula (III) and one or more of a pharmaceutically acceptable vehicle.

Pharmaceutical compositions of a compound of formula (I) or formula (IA) that is further given by formula (IV), as described herein, or a pharmaceutically acceptable salt, hydrate, solvate, isomer, enantiomer, diastereomer, or tautomer thereof, and one or more of a pharmaceutically acceptable carrier, adjuvant, or vehicle are disclosed.

In some embodiments, the pharmaceutical compositions include a compound of formula (IV) and one or more of a pharmaceutically acceptable carrier, adjuvant, or vehicle. In some embodiments, the pharmaceutical compositions include a compound of formula (IV) and one or more of a pharmaceutically acceptable carrier or vehicle. In some embodiments, the pharmaceutical compositions include a compound of formula (IV) and one or more of a pharmaceutically acceptable carrier. In some embodiments, the pharmaceutical compositions include a compound of formula (IV) and one or more of a pharmaceutically acceptable vehicle.

In some embodiments, the pharmaceutical compositions include a pharmaceutically acceptable salt of a compound of formula (IV) and one or more of a pharmaceutically acceptable carrier, adjuvant, or vehicle. In some embodiments, the pharmaceutical compositions include a pharmaceutically acceptable salt of a compound of formula (IV) and one or more of a pharmaceutically acceptable carrier or vehicle. In some embodiments, the pharmaceutical compositions include a pharmaceutically acceptable salt of a compound of formula (IV) and one or more of a pharmaceutically acceptable carrier. In some embodiments, the pharmaceutical compositions include a pharmaceutically acceptable salt of a compound of formula (IV) and one or more of a pharmaceutically acceptable vehicle.

Pharmaceutical compositions of a compound of formula (I) or formula (IA) that is further given by formula (V), as described herein, or a pharmaceutically acceptable salt, hydrate, solvate, isomer, enantiomer, diastereomer, or tautomer thereof, and one or more of a pharmaceutically acceptable carrier, adjuvant, or vehicle are disclosed.

In some embodiments, the pharmaceutical compositions include a compound of formula (V) and one or more of a pharmaceutically acceptable carrier, adjuvant, or vehicle. In some embodiments, the pharmaceutical compositions include a compound of formula (V) and one or more of a pharmaceutically acceptable carrier or vehicle. In some embodiments, the pharmaceutical compositions include a compound of formula (V) and one or more of a pharmaceutically acceptable carrier. In some embodiments, the pharmaceutical compositions include a compound of formula (V) and one or more of a pharmaceutically acceptable vehicle.

In some embodiments, the pharmaceutical compositions include a pharmaceutically acceptable salt of a compound of formula (V) and one or more of a pharmaceutically acceptable carrier, adjuvant, or vehicle. In some embodiments, the pharmaceutical compositions include a pharmaceutically acceptable salt of a compound of formula (V) and one or more of a pharmaceutically acceptable carrier or vehicle. In some embodiments, the pharmaceutical compositions include a pharmaceutically acceptable salt of a compound of formula (V) and one or more of a pharmaceutically acceptable carrier. In some embodiments, the pharmaceutical compositions include a pharmaceutically acceptable salt of a compound of formula (V) and one or more of a pharmaceutically acceptable vehicle.

Pharmaceutical compositions of a compound of formula (I) or formula (IA) that is further given by formula (VI), as described herein, or a pharmaceutically acceptable salt, hydrate, solvate, isomer, enantiomer, diastereomer, or tautomer thereof, and one or more of a pharmaceutically acceptable carrier, adjuvant, or vehicle are disclosed.

In some embodiments, the pharmaceutical compositions include a compound of formula (VI) and one or more of a pharmaceutically acceptable carrier, adjuvant, or vehicle. In some embodiments, the pharmaceutical compositions include a compound of formula (VI) and one or more of a pharmaceutically acceptable carrier or vehicle. In some embodiments, the pharmaceutical compositions include a compound of formula (VI) and one or more of a pharmaceutically acceptable carrier. In some embodiments, the pharmaceutical compositions include a compound of formula (VI) and one or more of a pharmaceutically acceptable vehicle.

In some embodiments, the pharmaceutical compositions include a pharmaceutically acceptable salt of a compound of formula (VI) and one or more of a pharmaceutically acceptable carrier, adjuvant, or vehicle. In some embodiments, the pharmaceutical compositions include a pharmaceutically acceptable salt of a compound of formula (VI) and one or more of a pharmaceutically acceptable carrier or vehicle. In some embodiments, the pharmaceutical compositions include a pharmaceutically acceptable salt of a compound of formula (VI) and one or more of a pharmaceutically acceptable carrier. In some embodiments, the pharmaceutical compositions include a pharmaceutically acceptable salt of a compound of formula (VI) and one or more of a pharmaceutically acceptable vehicle.

Methods of Using the Compounds of the Disclosure

One aspect of the present disclosure relates to a compound of formulas (I)-(VI) for use in medicine. Another aspect of the present disclosure relates to a method of modulating USP19, comprising administering to a patient in need thereof a therapeutically effective amount of a compound of any one of formulas (I)-(VI). Another aspect of the present disclosure relates to a method of inhibiting one or more of USP19, comprising administering to a patient in need thereof a therapeutically effective amount of a compound of any one of formulas (I)-(VI). In another aspect, the present disclosure relates to a method of modulating or inhibiting USP19, comprising administering to a patient in need thereof a therapeutically effective amount of a pharmaceutical composition comprising a compound of any one of formulas (I)-(VI).

USP19 Inhibitor Compounds are useful for treating disease states that are responsive to the inhibition of USP19. For example, USP19 Inhibitor Compounds are useful for the enhancement of muscle growth following injury or muscle wasting disease, protection from the deleterious consequences of obesity and diabetes, treatment of neurodegenerative diseases including Parkinson's disease or Alzheimer's disease, and the treatment of various cancers, including Ewing sarcoma. USP19 Inhibitor Compounds are useful in the development of pharmaceutical compositions suitable for the enhancement of muscle growth following injury or muscle wasting disease, protection from the deleterious consequences of obesity and diabetes, treatment of neurodegenerative diseases including Parkinson's disease or Alzheimer's disease, and the treatment of various cancers, including Ewing sarcoma.

Although the dosage of a compound of any one of formulas (I)-(VI) will vary according to the activity and/or toxicity of the particular compound, the condition being treated, and the physical form of the pharmaceutical composition being employed for administration, it may be stated by way of guidance that a dosage selected in the range from 1 to 2000 mg/kg of body weight per day will often be suitable. Those of ordinary skill in the art are familiar with methods for determining the appropriate dosage.

A USP19 Inhibitor Compound of the present disclosure can be dosed at a therapeutically effective level.

Methods of modulating or inhibiting USP19 in a patient comprising administering to a patient in need thereof a therapeutically effective amount of a compound of formula (I), as described herein, or a pharmaceutically acceptable salt, hydrate, solvate, isomer, enantiomer, diastereomer, or tautomer thereof, are disclosed.

In some aspects, the method of inhibiting USP19 in a patient comprises administering to a patient in need thereof a therapeutically effective amount of a compound of formula (I).

In some aspects, the method of inhibiting USP19 in a patient comprises administering to a patient in need thereof a therapeutically effective amount of a pharmaceutically acceptable salt of a compound of formula (I).

In some aspects, the method of inhibiting USP19 in a patient comprises administering to a patient in need thereof a therapeutically effective amount of a pharmaceutical composition that includes a compound of formula (I), as described herein.

In some aspects, the method of inhibiting USP19 in a patient comprises administering to a patient in need thereof a therapeutically effective amount of a pharmaceutical composition that includes pharmaceutically acceptable salt of a compound of formula (I), as described herein.

In some aspects, methods of modulating or inhibiting USP19 in a patient comprise administering to a patient in need thereof a therapeutically effective amount of a compound of formula (I) that is further given by formula (IA), as described herein, or a pharmaceutically acceptable salt, hydrate, solvate, isomer, enantiomer, diastereomer, or tautomer thereof.

In some aspects, the method of inhibiting USP19 in a patient comprises administering to a patient in need thereof a therapeutically effective amount of a compound of formula (IA).

In some aspects, the method of inhibiting USP19 in a patient comprises administering to a patient in need thereof a therapeutically effective amount of a pharmaceutically acceptable salt of a compound of formula (IA).

In some aspects, the method of inhibiting USP19 in a patient comprises administering to a patient in need thereof a therapeutically effective amount of a pharmaceutical composition that includes a compound of formula (IA), as described herein.

In some aspects, the method of inhibiting USP19 in a patient comprises administering to a patient in need thereof a therapeutically effective amount of a pharmaceutical composition that includes pharmaceutically acceptable salt of a compound of formula (IA), as described herein.

In some aspects, methods of modulating or inhibiting USP19 in a patient comprise administering to a patient in need thereof a therapeutically effective amount of a compound of formula (I) or formula (IA) that is further given by formula (II), as described herein, or a pharmaceutically acceptable salt, hydrate, solvate, isomer, enantiomer, diastereomer, or tautomer thereof.

In some aspects, the method of inhibiting USP19 in a patient comprises administering to a patient in need thereof a therapeutically effective amount of a compound of formula (II).

In some aspects, the method of inhibiting USP19 in a patient comprises administering to a patient in need thereof a therapeutically effective amount of a pharmaceutically acceptable salt of a compound of formula (II).

In some aspects, the method of inhibiting USP19 in a patient comprises administering to a patient in need thereof a therapeutically effective amount of a pharmaceutical composition that includes a compound of formula (II), as described herein.

In some aspects, the method of inhibiting USP19 in a patient comprises administering to a patient in need thereof a therapeutically effective amount of a pharmaceutical composition that includes pharmaceutically acceptable salt of a compound of formula (II), as described herein.

In some aspects, methods of modulating or inhibiting USP19 in a patient comprise administering to a patient in need thereof a therapeutically effective amount of a compound of formula (I) or formula (IA) that is further given by formula (III), as described herein, or a pharmaceutically acceptable salt, hydrate, solvate, isomer, enantiomer, diastereomer, or tautomer thereof.

In some aspects, the method of inhibiting USP19 in a patient comprises administering to a patient in need thereof a therapeutically effective amount of a compound of formula (III).

In some aspects, the method of inhibiting USP19 in a patient comprises administering to a patient in need thereof a therapeutically effective amount of a pharmaceutically acceptable salt of a compound of formula (III).

In some aspects, the method of inhibiting USP19 in a patient comprises administering to a patient in need thereof a therapeutically effective amount of a pharmaceutical composition that includes a compound of formula (III), as described herein.

In some aspects, the method of inhibiting USP19 in a patient comprises administering to a patient in need thereof a therapeutically effective amount of a pharmaceutical composition that includes pharmaceutically acceptable salt of a compound of formula (III), as described herein.

In some aspects, methods of modulating or inhibiting USP19 in a patient comprise administering to a patient in need thereof a therapeutically effective amount of a compound of formula (I) or formula (IA) that is further given by formula (IV), as described herein, or a pharmaceutically acceptable salt, hydrate, solvate, isomer, enantiomer, diastereomer, or tautomer thereof.

In some aspects, the method of inhibiting USP19 in a patient comprises administering to a patient in need thereof a therapeutically effective amount of a compound of formula (IV).

In some aspects, the method of inhibiting USP19 in a patient comprises administering to a patient in need thereof a therapeutically effective amount of a pharmaceutically acceptable salt of a compound of formula (IV).

In some aspects, the method of inhibiting USP19 in a patient comprises administering to a patient in need thereof a therapeutically effective amount of a pharmaceutical composition that includes a compound of formula (IV), as described herein.

In some aspects, the method of inhibiting USP19 in a patient comprises administering to a patient in need thereof a therapeutically effective amount of a pharmaceutical composition that includes pharmaceutically acceptable salt of a compound of formula (IV), as described herein.

In some aspects, methods of modulating or inhibiting USP19 in a patient comprise administering to a patient in need thereof a therapeutically effective amount of a compound of formula (I) or formula (IA) that is further given by formula (V), as described herein, or a pharmaceutically acceptable salt, hydrate, solvate, isomer, enantiomer, diastereomer, or tautomer thereof.

In some aspects, the method of inhibiting USP19 in a patient comprises administering to a patient in need thereof a therapeutically effective amount of a compound of formula (V).

In some aspects, the method of inhibiting USP19 in a patient comprises administering to a patient in need thereof a therapeutically effective amount of a pharmaceutically acceptable salt of a compound of formula (V).

In some aspects, the method of inhibiting USP19 in a patient comprises administering to a patient in need thereof a therapeutically effective amount of a pharmaceutical composition that includes a compound of formula (V), as described herein.

In some aspects, the method of inhibiting USP19 in a patient comprises administering to a patient in need thereof a therapeutically effective amount of a pharmaceutical composition that includes pharmaceutically acceptable salt of a compound of formula (V), as described herein.

In some aspects, methods of modulating or inhibiting USP19 in a patient comprise administering to a patient in need thereof a therapeutically effective amount of a compound of formula (I) or formula (IA) that is further given by formula (VI), as described herein, or a pharmaceutically acceptable salt, hydrate, solvate, isomer, or tautomer thereof.

In some aspects, the method of inhibiting USP19 in a patient comprises administering to a patient in need thereof a therapeutically effective amount of a compound of formula (VI).

In some aspects, the method of inhibiting USP19 in a patient comprises administering to a patient in need thereof a therapeutically effective amount of a pharmaceutically acceptable salt of a compound of formula (VI).

In some aspects, the method of inhibiting USP19 in a patient comprises administering to a patient in need thereof a therapeutically effective amount of a pharmaceutical composition that includes a compound of formula (VI), as described herein.

In some aspects, the method of inhibiting USP19 in a patient comprises administering to a patient in need thereof a therapeutically effective amount of a pharmaceutical composition that includes pharmaceutically acceptable salt of a compound of formula (VI), as described herein.

EXAMPLES

Materials and Instrumentation

All solvents used were commercially available and were used without further purification. Reactions were typically run using anhydrous solvents under an inert atmosphere of nitrogen.

Proton NMR spectra was recorded using either a Bruker BBFO ASCEND™400 AVANCE III 400 MHz or Bruker BBFO ULTRASHIELD™300; The deuterated solvent contained typically 0.03% to 0.05% v/v tetramethylsilane, which was used as the reference signal (set at δ 0.00 for $^1$H).

LCMS analyses were performed on a SHIMADZU LCMS with ESI electrospray ionization (m/z 90-900), consisting of an SPD-M20A PDA (190-400 nm), Alltech 3300 ELSD, and LCMS 2020 MS detector. The column was used was a Shim-pack XR-ODS, 2.2 μm, 3.0×50 mm. The instrument using reverse-phase conditions (acetonitrile/water, containing 0.05% acetic acid).

The following abbreviations are used in the examples below and elsewhere herein:

| | |
|---|---|
| ACN | Acetonitrile |
| AcOH | Acetic acid |
| $Cs_2CO_3$ | Cesium carbonate |
| δ | chemical shift |
| DCM | Dichloromethane or methylene chloride |
| DCE | 1,2-Dichloroethane |
| DIEA | N,N-Diisopropylethylamine |
| DMA | N,N-Dimethylacetamide |
| DME | Dimethoxyethane |
| DMF | N,N-Dimethylformamide |
| DMP | Dess-Martin Periodinane |
| DMSO | Dimethylsulfoxide |
| EDCI | N-(3-Dimethylaminopropyl)-N'-ethylcarbodiimide hydrochloride |
| h | Hour |
| $^1$H NMR | proton nuclear magnetic resonance |
| HATU | 2-(3H-[1,2,3]Triazolo[4,5-b]pyridin-3-yl)-1,1,3,3-tetramethylisouronium hexafluorophosphate |
| HCl | Hydrochloric acid |
| HOBT | 1H-Benzo[d][1,2,3]triazol-1-ol hydrate |
| HPLC | high performance liquid chromatography |
| Hz | Hertz |
| IPA | Isopropyl alcohol |
| LAH | lithium aluminum hydride |
| LCMS | liquid chromatography/mass spectrometry |
| LiOH | Lithium hydroxide |
| m-CPBA | m-Chloroperoxybenzoic acid |
| MeOH | Methanol |
| min | Minutes |
| MS | mass spectrometry |
| MsCl | Mesyl chloride |
| MTBE | Methyl tert-butyl ether |
| NaOH | Sodium hydroxide |
| NaH | Sodium hydride |
| NMP | N-Methyl-2-pyrrolidone |
| Pd/C | Palladium on carbon |
| $Pd(dppf)Cl_2$ | [1,1'-Bis(diphenylphosphino)ferrocene]dichloropalladium(II) |
| rt | room temperature |
| $R_t$ | retention time |
| TBDMS-Cl | tert-butyl dimethylsilyl chloride |
| TEA | Triethylamine |
| TFA | Trifluoroacetic acid |
| THF | Tetrahydrofuran |

Example 1

Synthesis of (S)-1-(((S)-7-(R)-3-cyclohexyl-2-methylpropanoyl)-10-hydroxy-7-azaspiro[4.5]decan-10-yl)methyl)-4-phenylpyrrolidin-2-one (13) and (R)-1-(((S)-7-((R)-3-cyclohexyl-2-methylpropanoyl)-10-hydroxy-7-azaspiro[4.5]decan-10-yl)methyl)-4-phenylpyrrolidin-2-one (14)

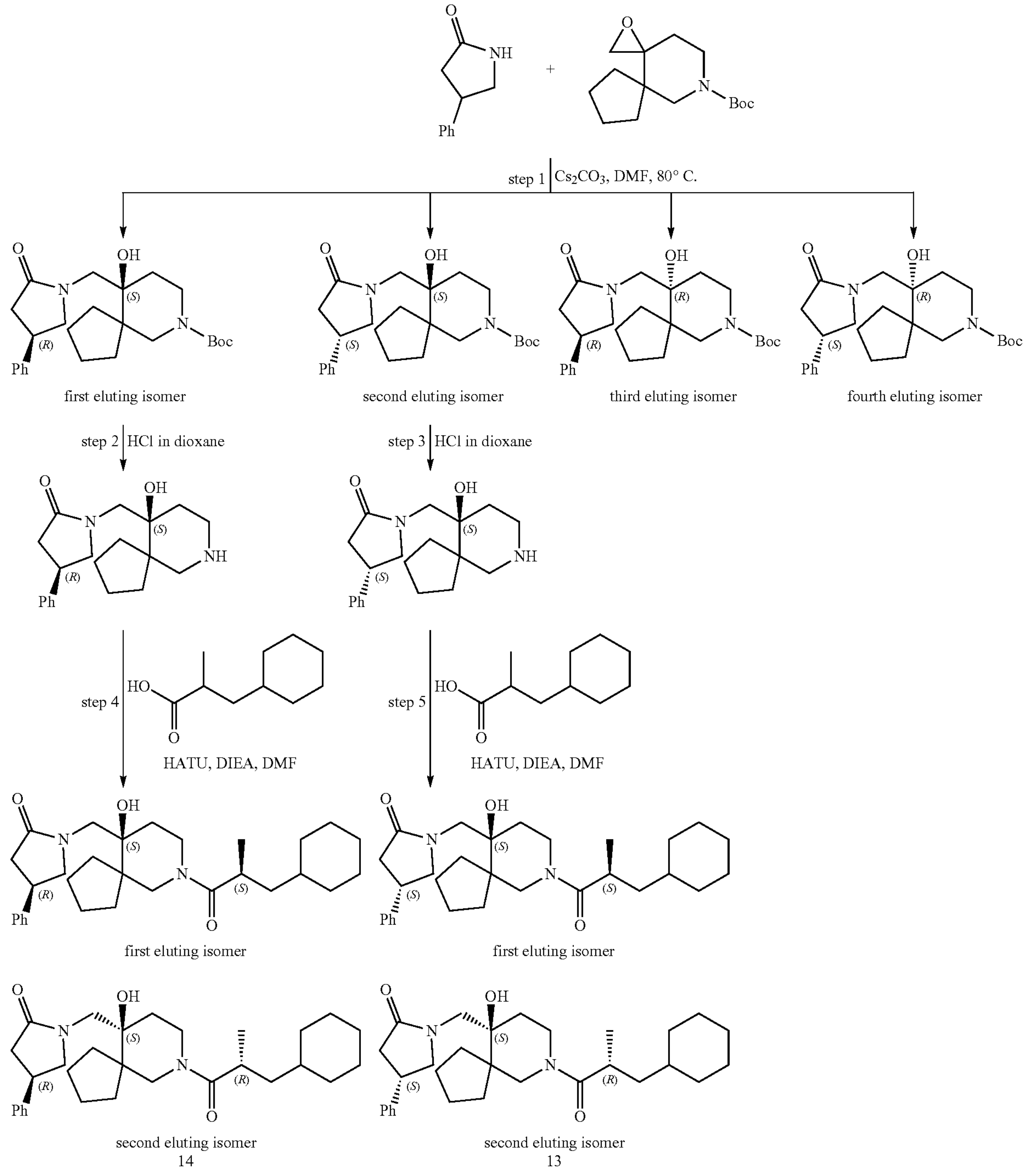

first eluting isomer
second eluting isomer
third eluting isomer
fourth eluting isomer
first eluting isomer
first eluting isomer
second eluting isomer
14
second eluting isomer
13

Step 1. tert-butyl (S)-10-hydroxy-10-(((R)-2-oxo-4-phenylpyrrolidin-1-yl)methyl)-7-azaspiro[4.5]decane-7-carboxylate (first eluting isomer) and tert-butyl (S)-10-hydroxy-10-(((S)-2-oxo-4-phenylpyrrolidin-1-yl)methyl)-7-azaspiro[4.5]decane-7-carboxylate (second eluting isomer).

To a stirred mixture of 4-phenylpyrrolidin-2-one (1.00 g, 6.20 mmol) and tert-butyl 1-oxa-10-azadispiro[2.0.4^[4].4^[3]]dodecane-10-carboxylate (3.32 g, 12.4 mmol) in DMF (30 mL) was added $Cs_2CO_3$ (4.04 g, 12.4 mmol). The resulting mixture was stirred for 16 hours at 85° C. under a nitrogen atmosphere. The mixture was cooled to room temperature, diluted with water (100 mL) and extracted with EtOAc (3×100 mL). The combined organic layers were washed with brine (3×100 mL), dried over anhydrous $Na_2SO_4$ and concentrated under reduced pressure.

The crude product was purified by reversed phase column chromatography (Column—$C_{18}$ silica gel, 120 g, 20-45 μm, 100 Å; mobile phase—water with 0.05% TFA and ACN (0% up to 60% in 40 minutes); Detector—UV 220 & 254 nm) to afford a mixture containing of all four diastereomers of tert-butyl 10-hydroxy-10-((2-oxo-4-phenylpyrrolidin-1-yl)methyl)-7-azaspiro[4.5]decane-7-carboxylate (500 mg, 17%) as an off-white solid. LCMS (ES, m/z): 429 $[M+H]^+$.

The diastereomeric mixture was separated by Chiral-Prep-HPLC with the following conditions: Column—CHIRALPAK IC, 2×25 cm, 5 μm; Mobile Phase A—Hexanes, Mobile Phase B—EtOH; Flow rate—20 mL/minute; Gradient—15% B to 15% B in 17 min; UV 220/254 nm; $R_t$1: 9.883 minutes; $R_t$2: 11.259 minutes; $R_t$3: 13.822 minutes; Injection Volume-1 ml; Number of Runs—10.

The collected fractions were concentrated to afford tert-butyl (S)-10-hydroxy-10-(((R)-2-oxo-4-phenylpyrrolidin-1-yl)methyl)-7-azaspiro[4.5]decane-7-carboxylate (first eluting isomer, 100 mg, off-white solid, chiral HPLC $R_t$=9.883 minutes, LCMS (ES, m/z): 429 $[M+H^+]$), tert-butyl (S)-10-hydroxy-10-(((S)-2-oxo-4-phenylpyrrolidin-1-yl)methyl)-7-azaspiro[4.5]decane-7-carboxylate (second eluting isomer, 100 mg, off-white solid, chiral HPLC $R_t$=11.259 minutes, LCMS (ES, m/z): 429 $[M+H^+]$) and a diastereomer mixture of tert-butyl 10-hydroxy-10-((2-oxo-4-phenylpyrrolidin-1-yl)methyl)-7-azaspiro[4.5]decane-7-carboxylate (third and fourth eluting isomers, 230 mg, chiral HPLC $R_t$=13.822 minutes).

Step 2. (R)-1-(((S)-10-hydroxy-7-azaspiro[4.5]decan-10-yl)methyl)-4-phenylpyrrolidin-2-one hydrochloride A solution of hydrochloric acid in 1,4-dioxane (3.00 mL, 4M) was added to tert-butyl (S)-10-hydroxy-10-(((R)-2-oxo-4-phenylpyrrolidin-1-yl)methyl)-7-azaspiro[4.5]decane-7-carboxylate (first eluting isomer, 100 mg, 0.23 mmol). The resulting mixture was stirred for 0.5 hours at 25° C. and concentrated under reduced pressure to afford (R)-1-(((S)-10-hydroxy-7-azaspiro[4.5]decan-10-yl)methyl)-4-phenylpyrrolidin-2-one, hydrochloride (85 mg, 100%) as a white solid. LCMS (ES, m/z): 329 $[M-HCl+H]^+$.

Step 3. (S)-1-(((S)-10-hydroxy-7-azaspiro[4.5]decan-10-yl)methyl)-4-phenylpyrrolidin-2-one hydrochloride A solution of hydrochloric acid in 1,4-dioxane (3.00 mL, 4M) was added to tert-butyl (S)-10-hydroxy-10-(((S)-2-oxo-4-phenylpyrrolidin-1-yl)methyl)-7-azaspiro[4.5]decane-7-carboxylate (second eluting isomer, 100 mg, 0.23 mmol). The resulting mixture was stirred for 0.5 hours at 25° C. and concentrated under reduced pressure to afford (S)-1-(((S)-10-hydroxy-7-azaspiro[4.5]decan-10-yl)methyl)-4-phenylpyrrolidin-2-one, hydrochloride (85 mg, 100%) as an off-white solid. LCMS (ES, m/z): 329 $[M-HCl+H]^+$.

Step 4. (R)-1-(((S)-7-((R)-3-cyclohexyl-2-methylpropanoyl)-10-hydroxy-7-azaspiro[4.5]decan-10-yl)methyl)-4-phenylpyrrolidin-2-one (second eluting isomer, 14)

To a stirred mixture of (R)-1-(((S)-10-hydroxy-7-azaspiro[4.5]decan-10-yl)methyl)-4-phenylpyrrolidin-2-one, hydrochloride (85 mg, 0.23 mmol) and racemic 3-cyclohexyl-2-methylpropanoic acid (46 mg, 0.27 mmol) in DMF (1.00 mL) was added HATU (208 mg, 0.54 mmol) and DIEA (226 μL, 1.37 mmol). The resulting mixture was stirred for 2 hours at 25° C.

The mixture was purified by reversed phase column chromatography (Column—$C_{18}$ silica gel, 40 g, 20-35 μm, 100 Å; mobile phase—water with 0.05% $NH_4CO_3$ and ACN (0% up to 60% ACN in 40 minutes); Detector—UV 220&254 nm) to afford (4R)-1-(((10S)-7-(3-cyclohexyl-2-methylpropanoyl)-10-hydroxy-7-azaspiro[4.5]decan-10-yl)methyl)-4-phenylpyrrolidin-2-one (100 mg).

The diastereomeric mixture was separated by Chiral-Prep-HPLC with the following conditions: Column—CHIRALPAK IF, 2×25 cm, 5 μm; Mobile Phase A—Hexanes (10 mM $NH_3$), Mobile Phase B—EtOH; Flow rate: 20 mL/min; Gradient—15% B to 15 B % in 16 min; UV 220/254 nm; $R_t$1: 11.247 minutes; $R_t$2: 13.452 minutes; Injection Volume—0.3 ml; Number Of Runs—7. The collected fractions were concentrated under reduced pressure and re-lyophilized to afford (R)-1-(((S)-7-((S)-3-cyclohexyl-2-methylpropanoyl)-10-hydroxy-7-azaspiro[4.5]decan-10-yl)methyl)-4-phenylpyrrolidin-2-one (first eluting isomer, 19 mg (14% yield), white solid, chiral HPLC $R_t$=11.247 minutes) and (R)-1-(((S)-7-((R)-3-cyclohexyl-2-methylpropanoyl)-10-hydroxy-7-azaspiro[4.5]decan-10-yl)methyl)-4-phenylpyrrolidin-2-one (14) (second eluting isomer, 21 mg (15% yield), white solid, chiral HPLC $R_t$=13.452 minutes).

Compound 14: $^1$H-NMR (DMSO-d6, 400 MHz) δ (ppm): 7.34-7.24 (m, 5H), 4.62-4.58 (m, 1H), 4.11-4.09 (m, 1H), 3.95-3.91 (m, 1H), 3.61-3.55 (m, 3H), 3.33-3.31 (m, 2H), 3.18-3.05 (m, 1H), 2.91-2.85 (m, 2H), 2.73-2.67 (m, 1H), 2.43-2.36 (m, 1H), 1.84-1.79 (m, 1H), 1.65-1.44 (m, 14H), 1.42-1.07 (m, 6H), 0.96-0.94 (m, 3H), 0.84-0.82 (m, 2H). LCMS (ES, m/z): 481 $[M+H]^+$.

Step 5. (S)-1-(((S)-7-((R)-3-cyclohexyl-2-methylpropanoyl)-10-hydroxy-7-azaspiro[4.5]decan-10-yl)methyl)-4-phenylpyrrolidin-2-one (second eluting isomer, 13)

To a stirred mixture of (S)-1-(((S)-10-hydroxy-7-azaspiro[4.5]decan-10-yl)methyl)-4-phenylpyrrolidin-2-one, hydrochloride (80 mg, 0.22 mmol, 1.00 equivalent) and racemic 3-cyclohexyl-2-methylpropanoic acid (41 mg, 0.24 mmol) in DMF (2.00 mL) was added HATU (185 mg, 0.48 mmol, 2.00 equivalents) and DIEA (200 μL, 1.21 mmol). The resulting mixture was stirred for 2 hours at 25° C.

The mixture was purified by reversed phase column chromatography (Column—$C_{18}$ silica gel, 40 g, 20-35 μm, 100 Å; mobile phase—water with 0.05% $NH_4CO_3$ and ACN (0% up to 60% ACN in 40 minutes); Detector—UV 220 & 254 nm) to afford (4S)-1-(((10S)-7-(3-cyclohexyl-2-methylpropanoyl)-10-hydroxy-7-azaspiro[4.5]decan-10-yl)methyl)-4-phenylpyrrolidin-2-one (100 mg).

The diastereomeric mixture was separated by Chiral-Prep-HPLC with the following conditions: Column—CHIRALPAK IF, 2×25 cm, 5 μm; Mobile Phase A—Hexanes (10 mM $NH_3$), Mobile Phase B—EtOH; Flow rate—20 mL/minute; Gradient—15% B to 15% B in 19 minutes; UV 220/254 nm; $R_t$1: 13.435 minutes; $R_t$2: 17.026 minutes; Injection Volume-0.4 mL; Number Of Runs—6. The collected fractions were concentrated under reduced pressure and re-lyophilized to afford (S)-1-(((S)-7-((R)-3-cyclohexyl-2-methylpropanoyl)-10-hydroxy-7-azaspiro[4.5]decan-10-yl)methyl)-4-phenylpyrrolidin-2-one (first eluting isomer, 21 mg (17% yield), white solid, chiral HPLC $R_t$=13.435 minutes) and (5)-1-(((S)-7-((R)-3-cyclohexyl-2-methylpropanoyl)-10-hydroxy-7-azaspiro[4.5]decan-10-yl)methyl)-4-phenylpyrrolidin-2-one (13) (second eluting isomer, 23 mg (19%, yield), white solid, chiral HPLC $R_t$=13.435 min).

Compound 13: $^1$H-NMR (DMSO-d6, 400 MHz) δ (ppm): 7.35-7.31 (m, 4H), 7.27-7.24 (m, 1H), 4.59-4.55 (m, 1H), 3.95-3.92 (m, 1H), 3.74-3.72 (m, 2H), 3.64-3.54 (m, 3H), 3.45-3.33 (m, 1H), 3.15-2.85 (m, 3H), 2.65-2.62 (m, 1H), 2.50-2.47 (m, 1H), 1.85-1.79 (m, 1H), 1.64-1.43 (m, 14H), 1.40-1.06 (m, 6H), 0.96-0.94 (m, 3H), 0.87-0.81 (m, 2H). LCMS (ES, m/z): 481 $[M+H]^+$.

Example 2
Synthesis of 2-((7-(3-Cyclohexyl-2-methylpropanoyl)-7-azaspiro[4.5]decan-10-yl)methyl)-N,N-dimethyl-1-oxoisoindoline-4-carboxamide (30)
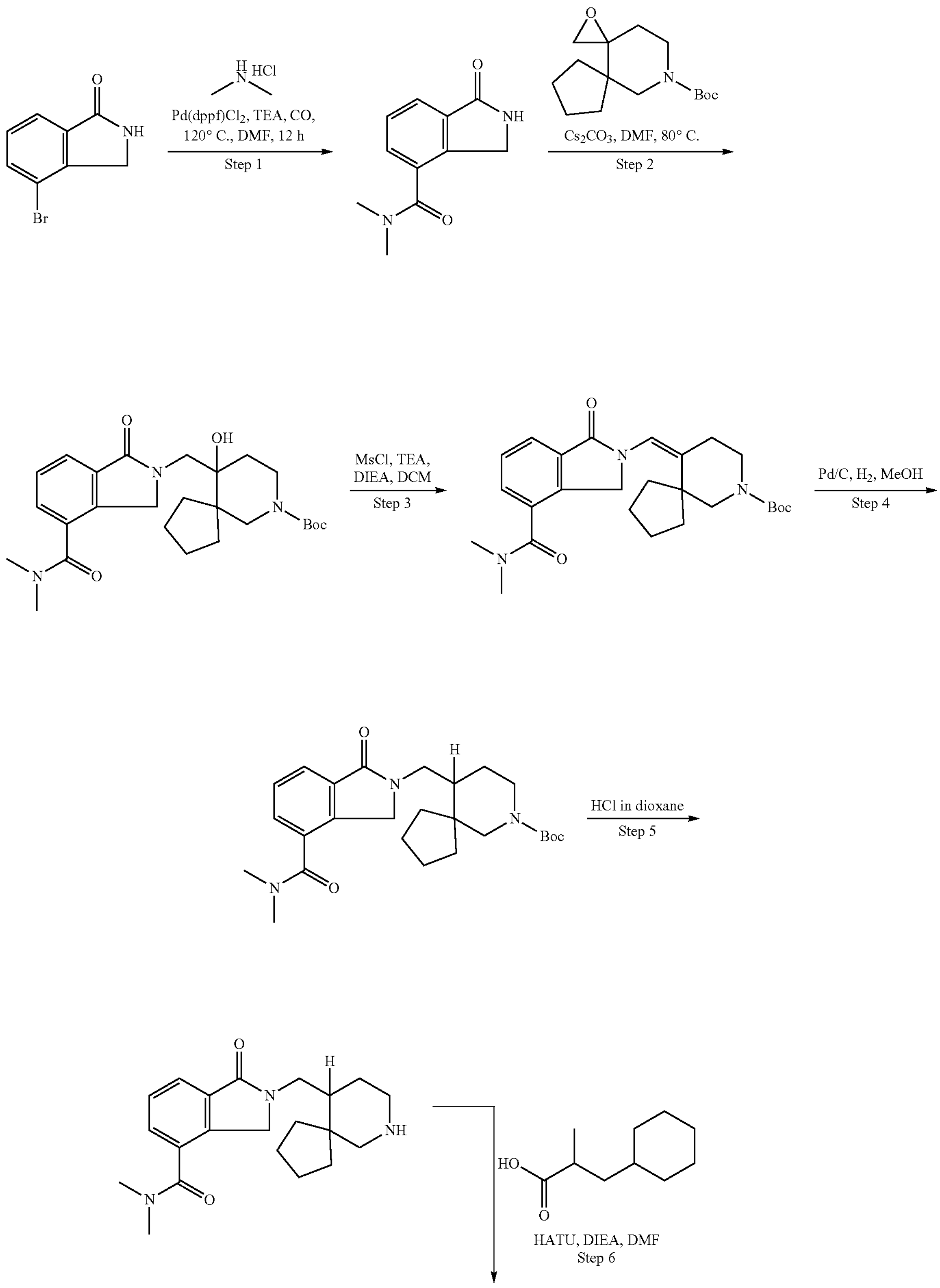

-continued

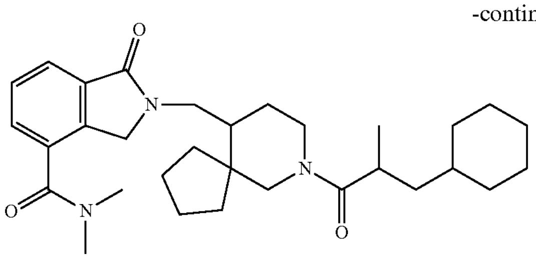

first eluting isomer

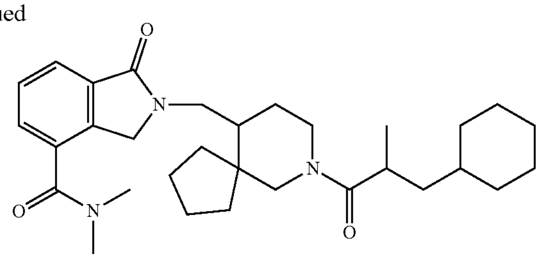

second eluting isomer

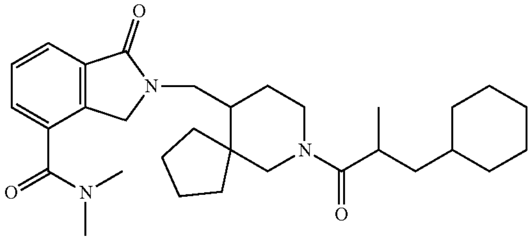

third eluting isomer

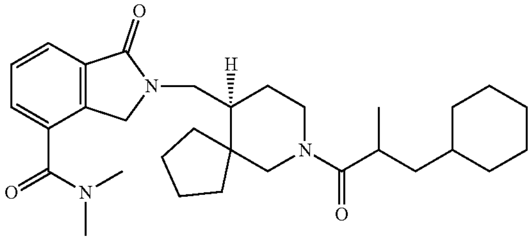

fourth eluting isomer

Step 1. N,N-dimethyl-1-oxo-2,3-dihydroisoindole-4-carboxamide

To a stirred mixture of 4-bromo-2,3-dihydroisoindol-1-one (10.0 g, 47.2 mmol) and dimethylamine (21.3 g, 471 mmol) in DMF (150 mL) was added $Et_3N$ (47.7 g, 471 mmol) and $Pd(dppf)Cl_2$ (6.90 g, 9.43 mmol). The resulting solution was stirred at 120° C. for 12 hours under a CO (g) (60 atm) atmosphere in a pressure tank. The mixture was cooled to room temperature and concentrated under reduced pressure.

The crude product was purified by reversed phase column chromatography (Column—$C_{18}$ silica gel, 330 g, 20-35 μm, 100 Å; mobile phase—water with 0.05% TFA and ACN (0% up to 60% in 40 minutes); Detector—UV 220 & 254 nm) to afford N,N-dimethyl-1-oxo-2,3-dihydroisoindole-4-carboxamide (3.00 g, 34%) as a yellow oil. LCMS (ES, m/z): 205 $[M+H]^+$.

Step 2. tert-butyl 10-[[4-(dimethylcarbamoyl)-1-oxo-3H-isoindol-2-yl]methyl]-10-hydroxy-7-azaspiro[4.5]decane-7-carboxylate To a stirred mixture of N,N-dimethyl-1-oxo-2,3-dihydroisoindole-4-carboxamide (500 mg, 2.44 mmol) and tert-butyl 1-oxa-10-azadispiro[2.0.4^[4].4^[3]]dodecane-10-carboxylate (982 mg, 3.67 mmol) in DMF (6.00 mL) was added $Cs_2CO_3$ (2.39 g, 7.34 mmol). The resulting mixture was stirred for 2 hours at 85° C. under a nitrogen atmosphere. The mixture was cooled to room temperature, diluted with water (50 mL) and extracted with DCM (3×50 mL). The combined organic layers were dried over anhydrous sodium sulfate and concentrated under reduced pressure.

The crude product was purified by reversed phase column chromatography (Column—$C_{18}$ silica gel, 40 g, 20-45 μm, 100 Å; mobile phase, water with 0.05% TFA and ACN (0% up to 60% in 40 minutes); Detector—UV 220 & 254 nm) to afford tert-butyl 10-[[4-(dimethylcarbamoyl)-1-oxo-3H-isoindol-2-yl]methyl]-10-hydroxy-7-azaspiro[4.5]decane-7-carboxylate (500 mg, 43%) as a yellow solid. LCMS (ES, m/z): 472 $[M+H]^+$.

Step 3. (10Z)-10-[[4-(dimethylcarbamoyl)-1-oxo-3H-isoindol-2-yl]methylidene]-7-azaspiro[4.5]decane-7-carboxylate To a stirred mixture of tert-butyl 10-[[4-(dimethylcarbamoyl)-1-oxo-3H-isoindol-2-yl]methyl]-10-hydroxy-7-azaspiro[4.5]decane-7-carboxylate (500 mg, 1.06 mmol) and MsCl (242 mg, 2.12 mmol) in DCM (25 mL) was added TEA (441 μL, 3.18 mmol) and DIEA (250 μL, 2.12 mmol) dropwise at 0° C. under nitrogen atmosphere. The resulting mixture was stirred for 12 hours at 25° C. The mixture was concentrated under vacuum.

The crude product was purified by reversed phase column chromatography (Column—$C_{18}$ silica gel, 40 g, 20-45 μm, 100 Å; mobile phase—water with 0.05% TFA and ACN (0% up to 60% ACN in 40 minutes); Detector—UV 220 & 254 nm) to afford tert-butyl (10Z)-10-[[4-(dimethylcarbamoyl)-1-oxo-3H-isoindol-2-yl]methylidene]-7-azaspiro[4.5]decane-7-carboxylate (140 mg, 28%) as a white solid. LCMS (ES, m/z): 454 $[M+H]^+$.

Step 4. tert-butyl 10-[[4-(dimethylcarbamoyl)-1-oxo-3H-isoindol-2-yl]methyl]-7-azaspiro[4.5]decane-7-carboxylate A mixture of tert-butyl (10Z)-10-[[4-(dimethylcarbamoyl)-1-oxo-3H-isoindol-2-yl]methylidene]-7-azaspiro[4.5]decane-7-carboxylate (130 mg, 0.28 mmol) and Pd/C (30 mg, 10%) in MeOH (5 mL) was stirred for 12 hours at 25° C. under a hydrogen atmosphere. The resulting mixture was filtered. The filtrate was concentrated under reduced pressure to afford tert-butyl 10-[[4-(dimethylcarbamoyl)-1-oxo-3H-isoindol-2-yl]methyl]-7-azaspiro[4.5]decane-7-carboxylate (100 mg, 73%) as a white solid. LCMS (ES, m/z): 456 $[M+H]^+$.

Step 5. 2-[7-azaspiro[4.5]decan-10-ylmethyl]-N,N-dimethyl-1-oxo-3H-isoindole-4-carboxamide A mixture of tert-butyl 10-[[4-(dimethylcarbamoyl)-1-oxo-3H-isoindol-2-yl]methyl]-7-azaspiro[4.5]decane-7-carboxylate (150 mg, 0.32 mmol) in HCl in 1,4-dioxane (3 mL, 4M) was stirred for 0.5 hours at 25° C. The mixture was concentrated under reduced pressure and the crude product was purified by reversed phase column chromatography (Column—$C_{18}$ silica gel, 40 g, 20-45 μm, 100 Å; mobile phase—water with 0.05% $NH_4HCO_3$ and ACN (0% up to 60% ACN in 40 minutes); Detector—UV 220 & 254 nm) to afford 2-[7-azaspiro[4.5]decan-10-ylmethyl]-N,N-dimethyl- 1-oxo-3H-isoindole-4-carboxamide (100 mg, 81%) as a white solid. LCMS (ES, m/z): 356 $[M+H]^+$.

Step 6. 2-((7-(3-Cyclohexyl-2-methylpropanoyl)-7-azaspiro[4.5]decan-10-yl)methyl)-N,N-dimethyl-1-oxoisoindoline-4-carboxamide (third eluting isomer, 30)

To a stirred mixture of 2-[7-azaspiro[4.5]decan-10-ylmethyl]-N,N-dimethyl-1-oxo-3H-isoindole-4-carboxamide (80 mg, 0.22 mmol) and 3-cyclohexyl-2-methylpropanoic acid (38 mg, 0.22 mmol) in DMF (2 mL) was added HATU (171 mg, 0.45 mmol) and DIEA (185 µL, 1.12 mmol). The resulting mixture was stirred for 1 hour at 25° C.

The mixture was purified by reversed phase column chromatography (Column—$C_{18}$ silica gel, 40 g, 20-45 µm, 100 Å; mobile phase—water with 0.05% $NH_4HCO_3$ and ACN (0% up to 60% ACN in 40 minutes); Detector—UV 220 & 254 nm) to afford racemic product (100 mg) as a yellow oil.

The racemate was separated by Chiral-Prep-HPLC with the following conditions: Column—Chiralpak IA, 2×25 cm, 5 µm; Mobile Phase A—MTBE (10 mM $NH_3$/MEOH), Mobile Phase B—EtOH; Flow rate—18 mL/minute; Gradient—40% B to 40% B in 30 minutes; UV—220/254 nm; $R_t$1: 12.922 minutes; $R_t$2: 15.888 minutes; $R_t$3: 24.417 minutes; Injection Volume—0.5 ml; Number Of Runs—12. The collected fraction was concentrated under reduced pressure and re-lyophilized to afford 2-((7-(3-cyclohexyl-2-methylpropanoyl)-7-azaspiro[4.5]decan-10-yl)methyl)-N,N-dimethyl-1-oxoisoindoline-4-carboxamide (first eluting isomer, 7 mg (6% yield), off-white solid, chiral HPLC $R_t$: 12.922 minutes), a diastereomeric mixture of 2-((7-(3-cyclohexyl-2-methylpropanoyl)-7-azaspiro[4.5]decan-10-yl)methyl)-N,N-dimethyl-1-oxoisoindoline-4-carboxamide (second and third eluting isomers, 30 mg, chiral HPLC $R_t$: 15.888 minutes), and 2-((7-(3-cyclohexyl-2-methylpropanoyl)-7-azaspiro[4.5]decan-10-yl)methyl)-N,N-dimethyl-1-oxoisoindoline-4-carboxamide (fourth eluting isomer, 6.7 mg (6% yield), off-white solid, chiral HPLC $R_t$: 24.417 minutes).

The diastereomeric mixture of the second and third eluting isomers was re-separated by Chiral-Prep-HPLC with the following conditions: Column—CHIRALPAK ID, 3×25 cm, 5 µm; Mobile Phase A—MTBE (10 mM $NH_3$/MEOH), Mobile Phase B—EtOH; Flow rate-30 mL/minute; Gradient—50% B to 50% B in 25 minutes; UV—254/220 nm; $R_t$1: 15.9 minutes; $R_t$2: 21.3 minutes; Injection Volume—3 ml; Number Of Runs—2. The collected fraction was concentrated under reduced pressure and re-lyophilized to afford 2-((7-(3-cyclohexyl-2-methylpropanoyl)-7-azaspiro[4.5]decan-10-yl)methyl)-N,N-dimethyl-1-oxoisoindoline-4-carboxamide (second eluting isomer, 9.2 mg (8% yield), off-white solid, chiral HPLC $R_t$: 15.9 minutes) and 2-((7-(3-cyclohexyl-2-methylpropanoyl)-7-azaspiro[4.5]decan-10-yl)methyl)-N,N-dimethyl-1-oxoisoindoline-4-carboxamide (30) (third eluting isomer, 10.8 mg (9% yield), off-white solid, chiral HPLC $R_t$: 21.3 minutes).

Compound 30: $^1$H-NMR (DMSO-d6, 400 MHz) δ (ppm): 7.73 (d, J=6.8 Hz, 1H), 7.59-7.53 (m, 2H), 4.53-4.41 (m, 2H), 4.10-3.75 (m, 2H), 3.70-3.50 (m, 1H), 3.38-3.34 (m, 1H), 3.21-3.11 (m, 1H), 3.02 (br s, 3H), 2.91-2.76 (m, 5H), 1.93-1.85 (m, 1H), 1.70-1.46 (m, 12H), 1.36-1.33 (m, 3H), 1.22-1.04 (m, 6H), 0.97-0.91 (m, 3H), 0.84-0.78 (m, 2H). LCMS (ES, m/z): 508 $[M+H]^+$.

Example 3

Synthesis of Compounds 1-12 and 15-29

Examples 1-12 and 15-29 were prepared from commercial materials in an analogous fashion to the heretofore described procedures used to prepare examples 13, 14, and 30. Absolute and relative stereochemistry was arbitrarily assigned in many instances and may actually differ from that which has been illustrated. Liquid chromatography mass spectrometry data, including retention time and a confirmatory mass ion, for all examples is provided in the following Table A.

Examples 31-36 are prepared from commercial materials in analogous fashion to the heretofore described procedures and examples.

Conditions for LC-MS analysis were as follows: HPLC—Waters Acquity Binary Solvent Manager; UV—Waters Acquity PDA; ELSD—Water Acquity ELSD; column—Waters Acquity UPLC CSH $C_{18}$, 1.7 µm, 2.1×50 mm; column temperature—35° C.; mobile phase A-95% water/5% acetonitrile with 0.1% formic acid; mobile phase B—95% acetonitrile/5% water with 0.085% formic acid; gradient—5-100% B over 2.0 minutes, hold 100% to 2.2 minutes; flow rate—0.6 mL/min; UV wavelength—220 nm; ionization—electrospray, positive and negative mode.

TABLE A

| Compound | Name | Exact Mass (calculated) | LC-MS: (ES, m/z) (observed) | LC-MS retention time (min) |
|---|---|---|---|---|
| 1 | 2-(((S)-7-((R)-3-cyclohexyl-2-methylpropanoyl)-10-hydroxy-7-azaspiro[4.5]decan-10-yl)methyl)isoindolin-1-one | 452.3 | 475.3 $(M + Na)^+$ | 1.87 |
| 2 | 2-(((S)-7-((R)-3-cyclohexyl-2-methylpropanoyl)-10-hydroxy-7-azaspiro[4.5]decan-10-yl)methyl)-N,N-dimethyl-1-oxoisoindoline-4-carboxamide | 523.3 | 546.4 $(M + Na)^+$ | 1.66 |
| 3 | 2-(((S)-7-((R)-3-cyclohexyl-2-methylpropanoyl)-10-hydroxy-7-azaspiro[4.5]decan-10-yl)methyl)-5-methylisoindolin-1-one | 466.3 | 489.4 $(M + Na)^+$ | 1.99 |
| 4 | 2-(((S)-7-((R)-3-cyclohexyl-2-methylpropanoyl)-10-hydroxy-7-azaspiro[4.5]decan-10-yl)methyl)-4-methylisoindolin-1-one | 466.3 | 489.4 $(M + Na)^+$ | 2.00 |
| 5 | 2-(((S)-7-((R)-3-cyclohexyl-2-methylpropanoyl)-10-hydroxy-7-azaspiro[4.5]decan-10-yl)methyl)-4-(oxazol-2-yl)isoindolin-1-one | 519.3 | 542.4 $(M + Na)^+$ | 1.96 |

TABLE A-continued

| Compound | Name | Exact Mass (calculated) | LC-MS: (ES, m/z) (observed) | LC-MS retention time (min) |
|---|---|---|---|---|
| 6 | 2-(((S)-7-((R)-3-cyclohexyl-2-methylpropanoyl)-10-hydroxy-7-azaspiro[4.5]decan-10-yl)methyl)-4-(thiazol-4-yl)isoindolin-1-one | 535.3 | 558.4 $(M + Na)^+$ | 2.01 |
| 7 | 2-(((S)-1-((R)-3-cyclohexyl-2-methylpropanoyl)-4-hydroxy-3,3-dimethylpiperidin-4-yl)methyl)-N,N-dimethyl-1-oxoisoindoline-4-carboxamide | 497.3 | 498.5 $(M + H)^+$ | 1.59 |
| 8 | 2-(((S)-7-((R)-3-cyclohexyl-2-methylpropanoyl)-10-hydroxy-7-azaspiro[4.5]decan-10-yl)methyl)-4-methoxyisoindolin-1-one | 482.3 | 505.4 $(M + Na)^+$ | 1.97 |
| 9 | 2-(((S)-7-((R)-3-cyclohexyl-2-methylpropanoyl)-10-hydroxy-7-azaspiro[4.5]decan-10-yl)methyl)-4-(1H-pyrazol-1-yl)isoindolin-1-one | 518.3 | 541.5 $(M + Na)^+$ | 2.00 |
| 10 | 2-(((S)-7-((R)-3-cyclohexyl-2-methylpropanoyl)-10-hydroxy-7-azaspiro[4.5]decan-10-yl)methyl)-N,N-dimethyl-1-oxoisoindoline-5-carboxamide | 523.3 | 524.5 $(M + H)^+$ | 1.68 |
| 11 | 4-chloro-2-(((S)-7-((R)-3-cyclohexyl-2-methylpropanoyl)-10-hydroxy-7-azaspiro[4.5]decan-10-yl)methyl)isoindolin-1-one | 486.3 | 509.3 $(M + Na)^+$ | 2.10 |
| 12 | (S)-247-(2-(1H-indol-3-yl)acetyl)-10-hydroxy-7-azaspiro[4.5]decan-10-yl)methyl)-N,N-dimethyl-1-oxoisoindoline-4-carboxamide | 528.3 | 529.8 $(M + Na)^+$ | 1.37 |
| 13 | (S)-1-(((S)-7-((R)-3-cyclohexyl-2-methylpropanoyl)-10-hydroxy-7-azaspiro[4.5]decan-10-yl)methyl)-4-phenylpyrrolidin-2-one | 480.3 | 503.4 $(M + Na)^+$ | 1.99 |
| 14 | (R)-1-(((S)-7-((R)-3-cyclohexyl-2-methylpropanoyl)-10-hydroxy-7-azaspiro[4.5]decan-10-yl)methyl)-4-phenylpyrrolidin-2-one | 480.3 | 503.4 $(M + Na)^+$ | 1.99 |
| 15 | (R)-1-(((S)-7-((R)-3-cyclohexyl-2-methylpropanoyl)-10-hydroxy-7-azaspiro[4.5]decan-10-yl)methyl)-4-phenylpyrrolidin-2-one | 494.4 | 517.5 $(M + Na)^+$ | 2.07 |
| 16 | (R)-1-(((S)-7-((R)-3-cyclohexyl-2-methylpropanoyl)-10-hydroxy-7-azaspiro[4.5]decan-10-yl)methyl)-4-(o-tolyl)pyrrolidin-2-one | 494.4 | 517.5 $(M + Na)^+$ | 2.07 |
| 17 | (S)-1-(((S)-1-((R)-3-cyclohexyl-2-methylpropanoyl)-4-hydroxy-3,3-dimethylpiperidin-4-yl)methyl)-4-phenylpyrrolidin-2-one | 454.3 | 477.4 $(M + Na)^+$ | 1.90 |
| 18 | (R)-1-(((S)-1-((R)-3-cyclohexyl-2-methylpropanoyl)-4-hydroxy-3,3-dimethylpiperidin-4-yl)methyl)-4-phenylpyrrolidin-2-one | 454.3 | 477.4 $(M + Na)^+$ | 1.90 |
| 19 | (S)-4-(4-chlorophenyl)-1-(((S)-7-((R)-3-cyclohexyl-2-methylpropanoyl)-10-hydroxy-7-azaspiro[4.5]decan-10-yl)methyl)pyrrolidin-2-one | 514.3 | 537.4 $(M + Na)^+$ | 2.12 |
| 20 | (R)-4-(4-chlorophenyl)-1-(((S)-7-((R)-3-cyclohexyl-2-methylpropanoyl)-10-hydroxy-7-azaspiro[4.5]decan-10-yl)methyl)pyrrolidin-2-one | 514.3 | 537.4 $(M + Na)^+$ | 2.13 |
| 21 | (S)-1-(((S)-7-((R)-3-cyclohexyl-2-methylpropanoyl)-10-hydroxy-7-azaspiro[4.5]decan-10-yl)methyl)-4-(3-methoxyphenyl)pyrrolidin-2-one | 510.3 | 533.5 $(M + Na)^+$ | 2.02 |
| 22 | (R)-1-(((S)-7-((R)-3-cyclohexyl-2-methylpropanoyl)-10-hydroxy-7-azaspiro[4.5]decan-10-yl)methyl)-4-(3-methoxyphenyl)pyrrolidin-2-one | 510.3 | 533.5 $(M + Na)^+$ | 2.03 |
| 23 | (S)-1-(((S)-7-((R)-3-cyclohexyl-2-methylpropanoyl)-10-hydroxy-7-azaspiro[4.5]decan-10-yl)methyl)-4-(p-tolyl)pyrrolidin-2-one | 494.4 | 517.8 $(M + Na)^+$ | 2.13 |

TABLE A-continued

| Compound | Name | Exact Mass (calculated) | LC-MS: (ES, m/z) (observed) | LC-MS retention time (min) |
|---|---|---|---|---|
| 24 | (R)-1-(((S)-7-((R)-3-cyclohexyl-2-methylpropanoyl)-10-hydroxy-7-azaspiro[4.5]decan-10-yl)methyl)-4-(p-tolyl)pyrrolidin-2-one | 494.4 | 517.8 $(M + Na)^+$ | 2.14 |
| 25 | (S)-1-(((S)-7-((R)-3-cyclohexyl-2-methylpropanoyl)-10-hydroxy-7-azaspiro[4.5]decan-10-yl)methyl)-4-methyl-4-phenylpyrrolidin-2-one | 494.4 | 517.8 $(M + Na)^+$ | 2.09 |
| 26 | (R)-1-(((S)-7-((R)-3-cyclohexyl-2-methylpropanoyl)-10-hydroxy-7-azaspiro[4.5]decan-10-yl)methyl)-4-methyl-4-phenylpyrrolidin-2-one | 494.4 | 517.8 $(M + Na)^+$ | 2.10 |
| 27 | 2-(((10S)-7-(3-cyclobutyl-2-methylpropanoyl)-10-hydroxy-7-azaspiro[4.5]decan-10-yl)methyl)-N,N-dimethyl-1-oxoisoindoline-4-carboxamide | 495.3 | 496.8 $(M + H)^+$ | 1.57 |
| 28 | 2-(((10S)-10-hydroxy-7-(2-methyl-3-phenylpropanoyl)-7-azaspiro[4.5]decan-10-yl)methyl)-N,N-dimethyl-1-oxoisoindoline-4-carboxamide | 517.3 | 518.8 $(M + H)^+$ | 1.51 |
| 29 | 1-(((S)-7-((R)-3-cyclohexyl-2-methylpropanoyl)-10-hydroxy-7-azaspiro[4.5]decan-10-yl)methyl)-4-phenyl-1,5-dihydro-2H-pyrrol-2-one | 478.32 | 501.4 $(M + Na)^+$ | 1.95 |
| 30 | 2-((7-(3-cyclohexyl-2-methylpropanoyl)-7-azaspiro[4.5]decan-10-yl)methyl)-N,N-dimethyl-1-oxoisoindoline-4-carboxamide | 507.3 | 530.5 $(M + Na)^+$ | 1.86 |

Example 4

USP19 Inhibition Biochemical Assay Protocol

USP19 enzymatic assays were performed in a final volume of 6 μL in buffer containing 20 mM Tris-HCl pH 8.0, (Corning 46-031-CM), and 1 mM GSH (Sigma, G4251), 0.03% BGG (Sigma, G7516), and 0.01% Triton X-100 (Sigma, 93443). Test compounds were serially diluted in DMSO (Sigma, G7516) to obtain 10-point, 3-fold series. Nanoliter quantities were pre-dispensed into 1536 assay plates (Corning, 9110BC) for the concentration response range, 26.6 μM to 1.35 nM. 3 μL of 2× enzyme was added to the assay plates, preincubated with compound for 30 minutes, and then 3 μL of 2× substrate was subsequently added to initiate the reaction (0.3 nM human USP19 (Boston Biochem, E-576) and 25 nM Ub-Rh110MP (UbiQ, UbiQ-126) final concentrations). Enzyme and substrate concentrations and incubation times were optimized for the maximal signal-to-background while maintaining linear initial velocity conditions at a fixed substrate concentration below $K_m$.

Fluorescence signal was measured on an EnVision Plate Reader (PerkinElmer) equipped with 485 nm excitation filter and 535 nm emission filters. Measurements were taken at 2.5 minute intervals for 10 minutes, curves were shown to progress linearly.

Rates were calculated by: rate=((final FLU−initial FLU)/600 seconds) where final FLU=fluorescence at time 10 minutes, initial FLU=fluorescence at time 0 minutes and 600=duration of reaction in seconds.

Data were reported as percent inhibition compared with control wells based on the following equation: % inh=100*((rate−AveLow)/(AveHigh−AveLow)) where rate=measured rate of fluorescence generated during assay, AveLow=average rate of no enzyme control (n=32), and AveHigh=average rate of DMSO control (n=32).

$IC_{50}$ values were determined by curve fitting of the standard 4 parameter logistic fitting algorithm included in the Activity Base software package (IDBS) using XE Designer equation Model 205. Data were fitted using the Levenburg Marquardt algorithm. 1050 values for specific embodied compounds are reported in Table B.

TABLE B

| Compound | Structure and Name | USP19 $IC_{50}$ (μM) |
|---|---|---|
| 1 | 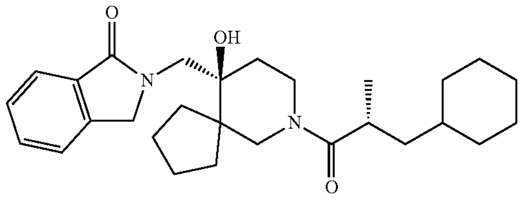 2-(((S)-7-((R)-3-cyclohexyl-2-methylpropanoyl)-10-hydroxy-7-azaspiro[4.5]decan-10-yl)methyl)isoindolin-1-one | 1.1 |

TABLE B-continued

| Compound | Structure and Name | USP19 $IC_{50}$ (μM) |
| --- | --- | --- |
| 2 | 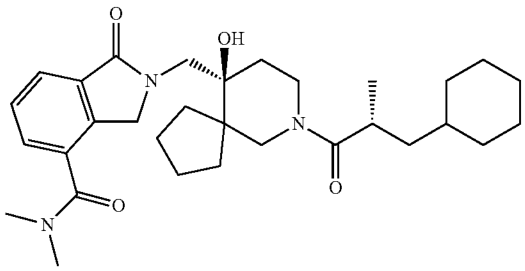 2-(((S)-7-((R)-3-cyclohexyl-2-methylpropanoyl)-10-hydroxy-7-azaspiro[4.5]decan-10-yl)methyl)-N-N-dimethyl-1-oxoisoindoline-4-carboxamide | 0.15 |
| 3 | 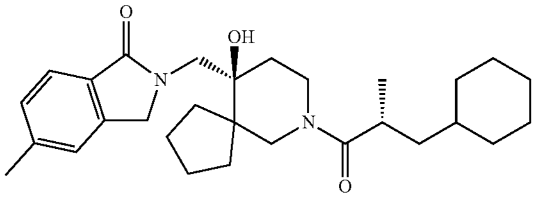 2-(((S)-7-((R)-3-cyclohexyl-2-methylpropanoyl)-10-hydroxy-7-azaspiro[4.5]decan-10-yl)methyl)-5-methylisoindolin-1-one | 0.074 |
| 4 | 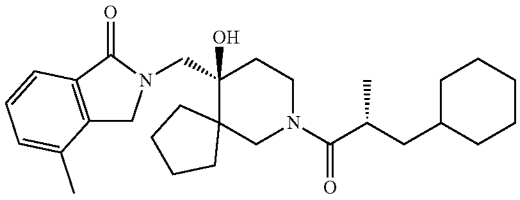 2-(((S)-7-((R)-3-cyclohexyl-2-methylpropanoyl)-10-hydroxy-7-azaspiro[4.5]decan-10-yl)methyl)-4-methylisoindolin-1-one | 0.53 |
| 5 | 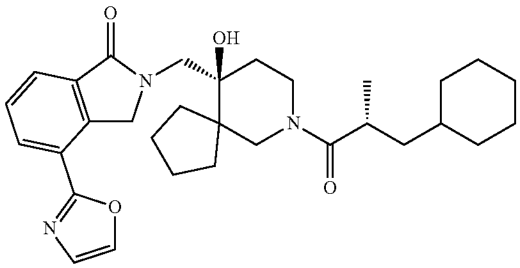 2-(((S)-7-((R)-3-cyclohexyl-2-methylpropanoyl)-10-hydroxy-7-azaspiro[4.5]decan-10-yl)methyl)-4-(oxazol-2-yl)isoindolin-1-one | 0.28 |

TABLE B-continued

| Compound | Structure and Name | USP19 $IC_{50}$ (μM) |
|---|---|---|
| 6 | 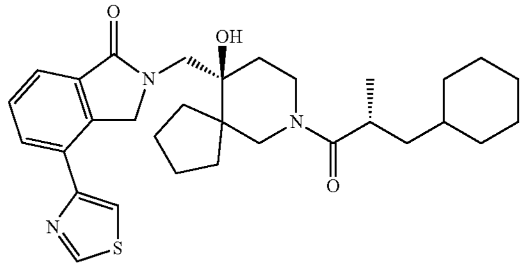 2-(((S)-7-((R)-3-cyclohexyl-2-methylpropanoyl)-10-hydroxy-7-azaspiro[4.5]decan-10-yl)methyl)-4-(thiazol-4-yl)isoindolin-1-one | 0.94 |
| 7 | 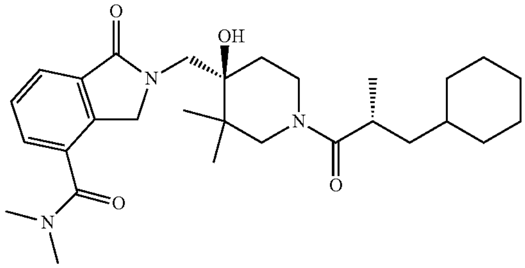 2-(((S)-1-((R)-3-cyclohexyl-2-methylpropanoyl)-4-hydroxy-3,3-dimethylpiperidin-4-yl)methyl-N,N-dimethyl-1-oxoisoindoline-4-carboxamide | 1.7 |
| 8 | 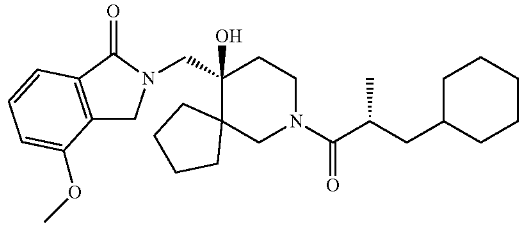 2-(((S)-7-((R)-3-cyclohexyl-2-methylpropanoyl)-10-hydroxy-7-azaspiro[4.5]decan-10-yl)methyl-4-methoxyisoindolin-1-one | 0.50 |
| 9 | 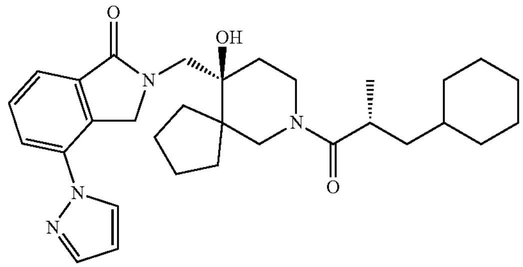 2-(((S)-7-((R)-3-cyclohexyl-2-methylpropanoyl)-10-hydroxy-7-azaspiro[4.5]decan-10-yl)methyl)-4-(1H-pyrazol-1-yl)isoindolin-1-one | 0.28 |

TABLE B-continued

| Compound | Structure and Name | USP19 $IC_{50}$ (μM) |
|---|---|---|
| 10 | 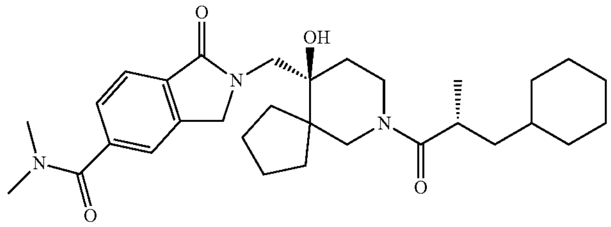 2-(((S)-7-((R)-3-cyclohexyl-2-methylpropanoyl)-10-hydroxy-7-azaspiro[4.5]decan-10-yl)methyl)-N,N-dimethyl-1-oxoisoindolin-5-carboxamide | 0.19 |
| 11 | 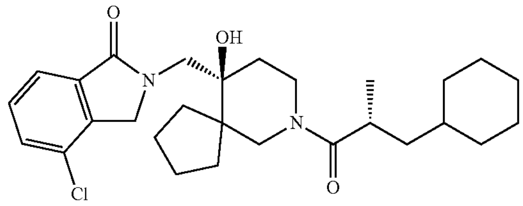 4-chloro-2-(((S)-7-((R)-3-cyclohexyl-2-methylpropanoyl)-10-hydroxy-7-azaspiro[4.5]decan-10-yl)methyl)isoindolin-1-one | 0.44 |
| 12 | 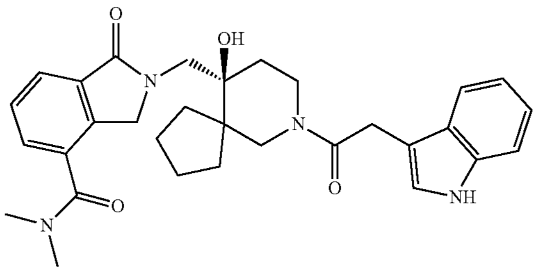 (S)-2-((7-(2-(1H-indol-3-yl)acetyl)-10-hydroxy-7-azaspiro[4.5]decan-10-yl)methyl)-N,N-dimethyl-1-oxoisoindoline-4-carboxamide | 14 |
| 13 | 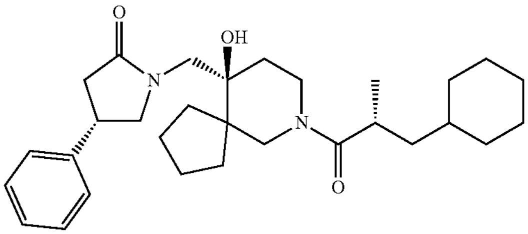 (S)-1-(((S)-7-((R)-3-cyclohexyl-2-methylpropanoyl)-10-hydroxy-7-azaspiro[4.5]decan-10-yl)methyl)-4-phenylpyrrolidin-2-one | 0.11 |

TABLE B-continued

| Compound | Structure and Name | USP19 $IC_{50}$ (μM) |
|---|---|---|
| 14 | 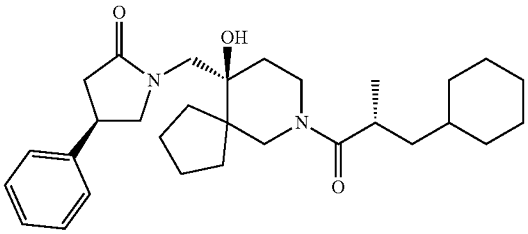 (R)-1-(((S)-7-((R)-3-cyclohexyl-2-methylpropanoyl)-10-hydroxy-7-azaspiro[4.5]decan-10-yl)methyl)-4-phenylpyrrolidin-2-one | 0.14 |
| 15 | 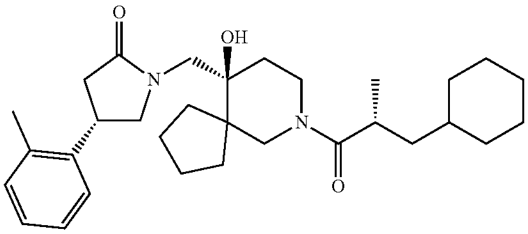 (S)-1-(((S)-7-((R)-3-cyclohexyl-2-methylpropanoyl)-10-hydroxy-7-azaspiro[4.5]decan-10-yl)methyl)-4-(o-tolyl)pyrrolidin-2-one | 0.15 |
| 16 | 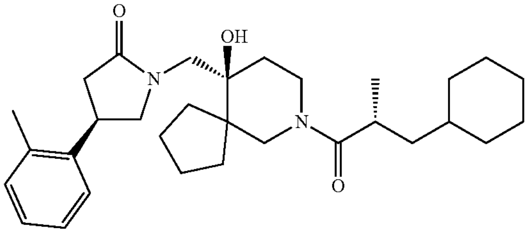 (R)-1-(((S)-7-((R)-3-cyclohexyl-2-methylpropanoyl)-10-hydroxy-7-azaspiro[4.5]decan-10-yl)methyl)-4-(o-tolyl)pyrrolidin-2-one | 0.80 |
| 17 | 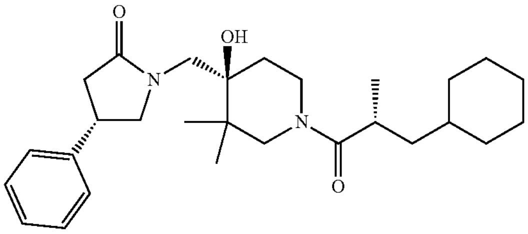 (S)-1-(((S)-1-((R)-3-cyclohexyl-2-methylpropanoyl)-4-hydroxy-3,3-dimethylpiperidin-4-yl)methyl)-4-phenylpyrrolidin-2-one | 1.6 |

TABLE B-continued

| Compound | Structure and Name | USP19 $IC_{50}$ (μM) |
|---|---|---|
| 18 | 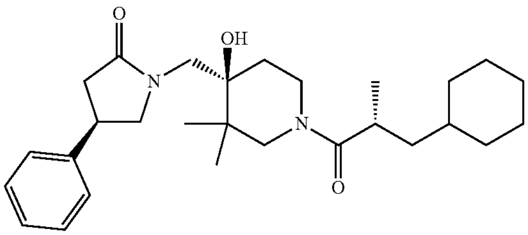 (R)-1-(((S)-1-((R)-3-cyclohexyl-2-methylpropanoyl)-4-hydroxy-3,3-dimethylpiperidin-4-yl)methyl)-4-phenylpyrrolidin-2-one | 0.74 |
| 19 | 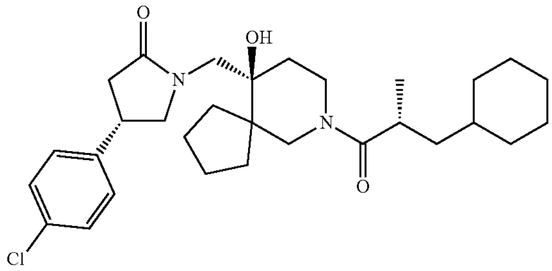 (S)-4-(4-chlorophenyl)-1-(((S)-7-((R)-3-cyclohexyl-2-methylpropanoyl)-10-hydroxy-7-azaspiro[4.5]decan-10-yl)methyl)pyrrolidin-2-one | 0.29 |
| 20 | 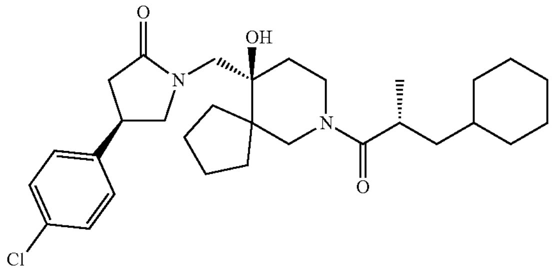 (R)-4-(4-chlorophenyl)-1-(((S)-7-((R)-3-cyclohexyl-2-methylpropanoyl)-10-hydroxy-7-azaspiro[4.5]decan-10-yl)methyl)pyrrolidin-2-one | 0.11 |
| 21 | 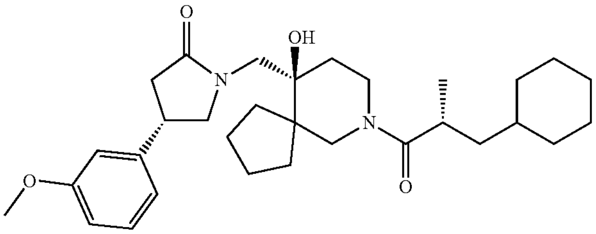 (S)-1-(((S)-7-((R)-3-cyclohexyl-2-methylpropanoyl)-10-hydroxy-7-azaspiro[4.5]decan-10-yl)methyl)-4-(3-methoxyphenyl)pyrrolidin-2-one | 0.21 |

TABLE B-continued

| Compound | Structure and Name | USP19 $IC_{50}$ (μM) |
| --- | --- | --- |
| 22 | 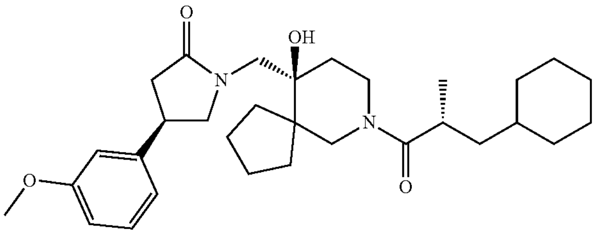 (R)-1-(((S)-7-((R)-3-cyclohexyl-2-methylpropanoyl)-10-hydroxy-7-azaspiro[4.5]decan-10-yl)methyl)-4-(3-methoxyphenyl)pyrrolidin-2-one | 0.12 |
| 23 | 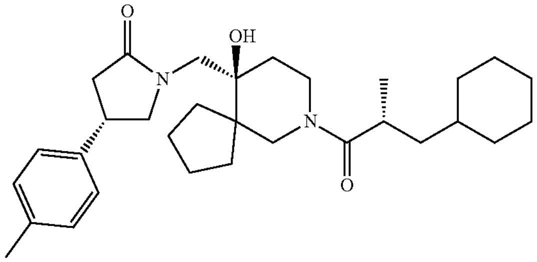 (S)-1-(((S)-7-((R)-3-cyclohexyl-2-methylpropanoyl)-10-hydroxy-7-azaspiro[4.5]decan-10-yl)methyl)-4-(p-tolyl)pyrrolidin-2-one | 0.45 |
| 24 | 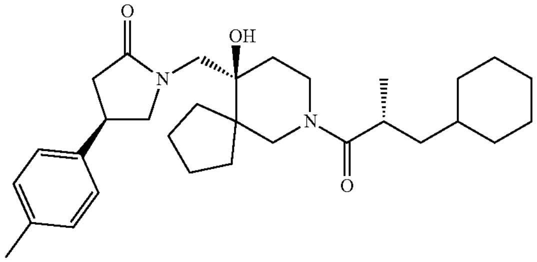 (R)-1-(((S)-7-((R)-3-cyclohexyl-2-methylpropanoyl)-10-hydroxy-7-azaspiro[4.5]decan-10-yl)methyl)-4-(p-tolyl)pyrrolidin-2-one | 0.22 |
| 25 | 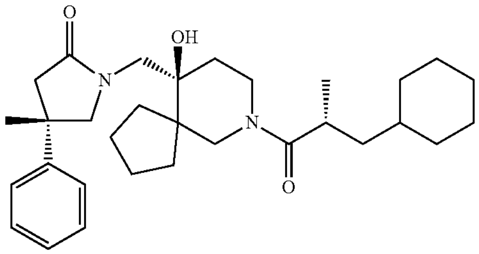 (S)-1-(((S)-7-((R)-3-cyclohexyl-2-methylpropanoyl)-10-hydroxy-7-azaspiro[4.5]decan-10-yl)methyl)-4-methyl-4-phenylpyrrolidin-2-one | 0.76 |

TABLE B-continued

| Compound | Structure and Name | USP19 $IC_{50}$ (μM) |
| --- | --- | --- |
| 26 | 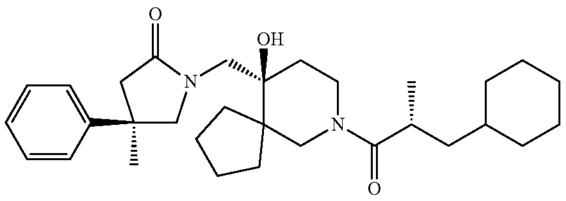 (R)-1-(((S)-7-((R)-3-cyclohexyl-2-methylpropanoyl)-10-hydroxy-7-azaspiro[4.5]decan-10-yl)methyl)-4-methyl-4-phenylpyrrolidin-2-one | 0.32 |
| 27 | 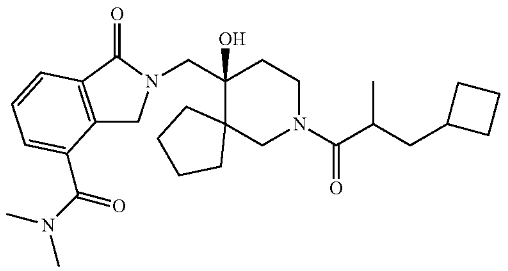 2-(((10S)-7-(3-cyclobutyl-2-methylpropanoyl)-10-hydroxy-7-azaspiro[4.5]decan-10-yl)methyl)-N,N-dimethyl-1-oxoisoindoline-4-carboxamide | 2.4 |
| 28 | 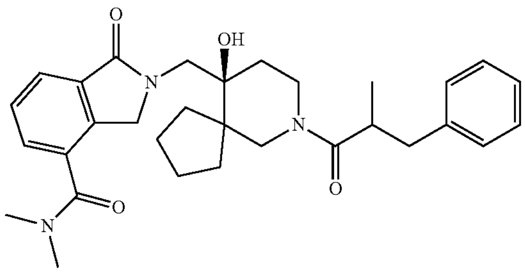 2-(((10S)-10-hydroxy-7-(2-methyl-3-phenylpropanoyl)-7-azaspiro[4.5]decan-10-yl)methyl)-N,N-dimethyl-1-oxoisoindoline-4-carboxamide | 3.1 |
| 29 | 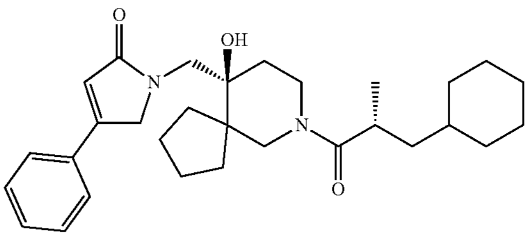 1-(((S)-7-((R)-3-cyclohexyl-2-methylpropanoyl)-10-hydroxy-7-azaspiro[4.5]decan-10-yl)methyl)-4-phenyl-1,5-dihydro-2H-pyrrol-2-one | 0.049 |

TABLE B-continued

| Compound | Structure and Name | USP19 $IC_{50}$ (μM) |
|---|---|---|
| 30 | 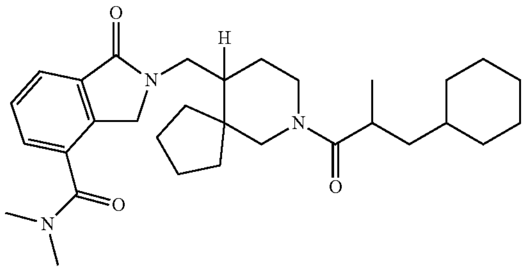 2-((7-(3-cyclohexyl-2-methylpropanoyl)-7-azaspiro[4.5]decan-10-yl)methyl)-N,N-dimethyl-1-oxoisoindoline-4-carboxamide | 0.058 |
| 31 | 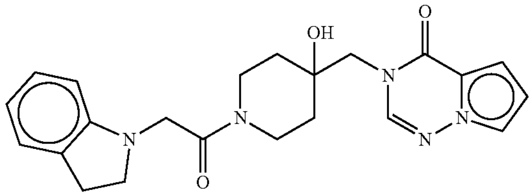 3-((4-hydroxy-1-(2-(indolin-1-yl)acetyl)piperidin-4-yl)methyl)pyrrolo[2,1-f][1,2,4]triazin-4(3H)-one | 3.1 |
| 32 | 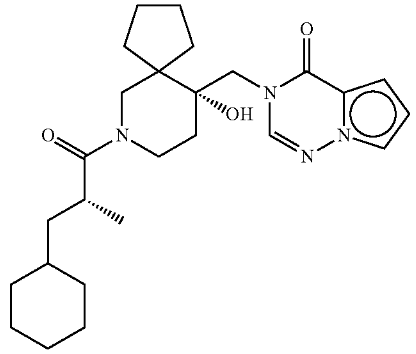 3-(((R)-7-((R)-3-cyclohexyl-2-methylpropanoyl)-10-hydroxy-7-azaspiro[4.5]decan-10-yl)methyl)pyrrolo[2,1-f][1,2,4]triazin-4(3H)-one | 1.207 |
| 33 | 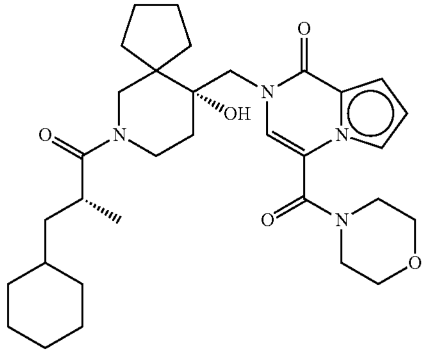 2-(((R)-7-((R)-3-cyclohexyl-2-methylpropanoyl)-10-hydroxy-7-azaspiro[4.5]decan-10-yl)methyl)-4-(morpholine-4-carbonyl)pyrrolo[1,2-a]pyrazin-1(2H)-one | 1.046 |

TABLE B-continued
| Compound | Structure and Name | USP19 $IC_{50}$ (μM) |
|---|---|---|
| 34 | 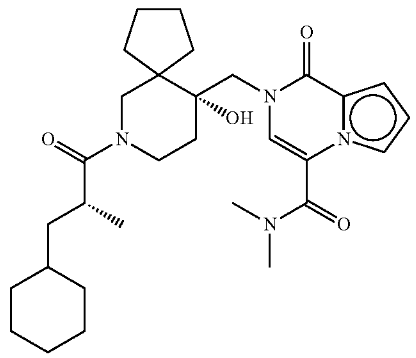 2-(((R)-7-((R)-3-cyclohexyl-2-methylpropanoyl)-10-hydroxy-7-azaspiro[4.5]decan-10-yl)methyl)-N,N-dimethyl-1-oxo-1,2-dihydropyrrolo[1,2-a]pyrazine-4-carboxamide | 1.434 |
| 35 | 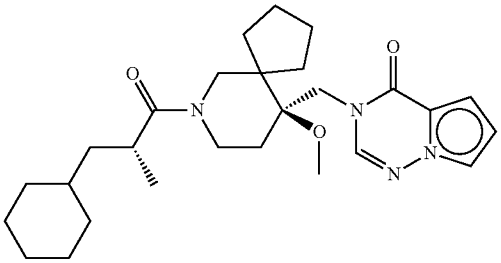 3-(((S)-7-((R)-3-cyclohexyl-2-methylpropanoyl)-10-methoxy-7-azaspiro[4.5]decan-10-yl)methyl)pyrrolo[2,1-f][1,2,4]triazin-4(3H)-one | 3.6 |
| 36 | 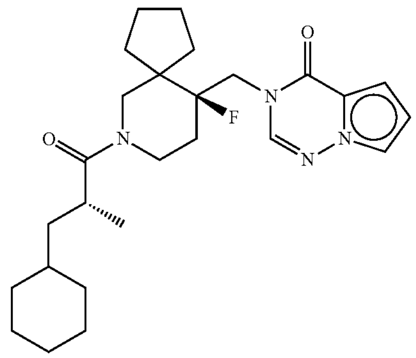 3-(((S)-7-((R)-3-cyclohexyl-2-methylpropanoyl)-10-fluoro-7-azaspiro[4.5]decan-10-yl)methyl)pyrrolo[2,1-f][1,2,4]triazin-4(3H)-one | 2.78 |

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description are by way of example to illustrate the discoveries provided herein. Furthermore, the foregoing Description and Examples are exemplary of the present invention and not limiting thereof. The scope of the invention is therefore set out in the appended claims.

We claim:

1. A compound of formula (I):

(I)

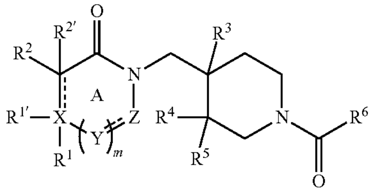

and enantiomers, diastereomers, and pharmaceutically acceptable salts thereof, wherein:

X is N or C;

wherein if X is N, one of $R^1$ and $R^{1'}$ is absent and one of $R^2$ and $R^{2'}$ is absent;

Y is N or $CR^7$;

Z is CH or $CH_2$;

$R^1$ and $R^{1'}$ are each independently selected from H, $C_{1-4}$ alkyl, and aryl optionally substituted with one $R^8$;

$R^2$ and $R^{2'}$ are each independently selected from H and $C_{1-4}$ alkyl;

wherein one of $R^1$ or $R^{1'}$ may be joined to one of $R^2$ or $R^{2'}$ to form an aryl or heteroaryl ring that includes the atoms to which they are attached and is substituted with one $R^9$;

one of $R^1$ or $R^{1'}$ and one of $R^2$ or $R^{2'}$ may be absent, such that ring A contains an unsaturated bond between X and the carbon to which $R^2$ and $R^{2'}$ are connected;

$R^3$ is selected from: H, —$OR^{10}$, and halogen;

$R^4$ is H or $C_{1-4}$ alkyl;

$R^5$ is H or $C_{1-4}$ alkyl;

wherein $R^4$ and $R^5$ may be joined to one another to form a cycloalkyl that includes the carbon to which they are attached;

$R^6$ is selected from: alkylcycloalkyl, alkylaryl, and alkylheteroaryl, each of which may optionally be substituted with one $C_{1-4}$ alkyl;

$R^7$ is —$C(O)R^{11}$;

$R^8$ is selected from: halogen, $C_{1-4}$ alkyl, and $C_{1-4}$ alkoxy;

$R^9$ is selected from: H, halogen, $C_{1-4}$ alkyl, $C_{1-4}$ alkoxy, —$C(O)N(R^{12})_2$, and heteroaryl;

$R^{10}$ is H or $C_{1-4}$ alkyl;

$R^{11}$ is —$N(R^{12})_2$ or a 5 to 6-membered heterocycle containing two heteroatoms selected from N and O;

$R^{12}$ is a $C_{1-4}$ alkyl group; and m is 0.

2. The compound of claim 1, wherein $R^6$ is selected from the group consisting of:

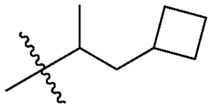
,
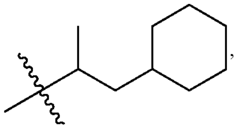
,
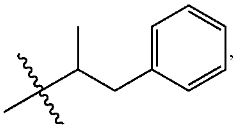
,
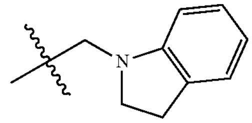
, and
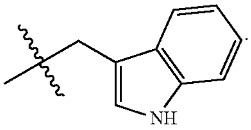
.

3. The compound of claim 1, wherein each $R^4$ and $R^5$ are independently selected from $C_{1-4}$ alkyl.

4. The compound of claim 1, further given by formula (II):

(II)

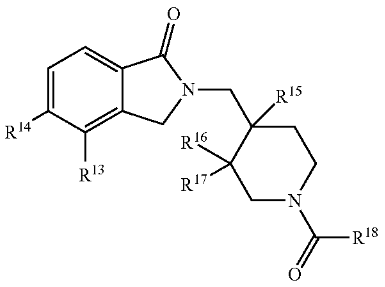

and enantiomers, diastereomers, and pharmaceutically acceptable salts thereof, wherein, $R^{13}$ is selected from: H, halogen, $C_{1-4}$ alkyl, $C_{1-4}$ alkoxy, —$C(O)N(R^{19})_2$, or a five-membered heteroaryl ring;

$R^{14}$ is selected from: H, $C_{1-4}$ alkyl, and —$C(O)N(R^{19})_2$; wherein one of $R^{13}$ and $R^{14}$ must be H;

$R^{15}$ is H or OH;

$R^{16}$ is a $C_{1-4}$ alkyl group;

$R^{17}$ is a $C_{1-4}$ alkyl group;

wherein $R^{16}$ and $R^{17}$ may be joined to one another to form a cycloalkyl that includes the carbon to which they are attached;

$R^{18}$ is selected from: alkylcycloalkyl, alkylphenyl, and alkylheteroaryl, each of which may optionally be substituted with one $C_{1-4}$ alkyl; and $R^{19}$ is a $C_{1-4}$ alkyl group.

5. The compound of claim 4, wherein $R^{13}$ is selected from the group consisting of: —Cl, methyl, methoxy, —$C(O)N(CH_3)_2$, thiazolyl, pyrazolyl, and oxazolyl.

6. The compound of claim 4, wherein $R^{14}$ is selected from the group consisting of: methyl and —$C(O)N(CH_3)_2$.

7. The compound of claim 4, wherein $R^{18}$ is selected from the group consisting of:

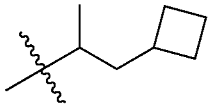
,
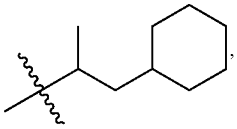
,

-continued

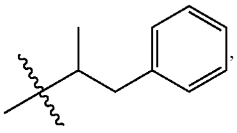, and 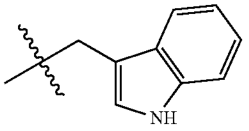.

8. The compound of claim 1, further given by formula (IV):

(IV)

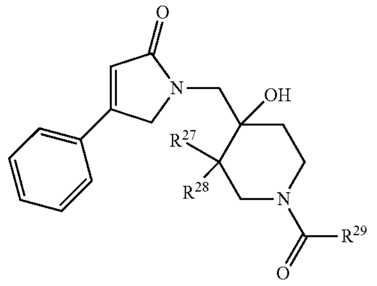

and enantiomers, diastereomers, and pharmaceutically acceptable salts thereof, wherein:

$R^{27}$ is a $C_{1-4}$ alkyl group;

$R^{28}$ is a $C_{1-4}$ alkyl group;

wherein $R^{27}$ and $R^{28}$ may be joined to one another to form a cycloalkyl that includes the carbon to which they are attached; and $R^{29}$ is an alkylcycloalkyl group substituted with one $C_{1-4}$ alkyl group.

9. A pharmaceutical composition comprising a compound of claim 1 and one or more of a pharmaceutically acceptable carrier, adjuvant, or vehicle.

10. A method of treating, preventing, inhibiting, or eliminating a disease or disorder associated with the activity of USP19 in a patient comprising: administering to the patient in need thereof a therapeutically effective amount of the compound of claim 1.

11. The method of claim 10, wherein the disorder is selected from the group consisting of Parkinson's disease, Ewing sarcoma, muscle wasting, and diabetes.

12. The compound of claim 4, selected from the group consisting of:

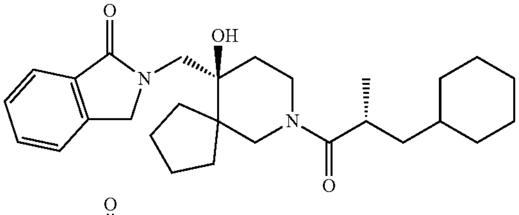,

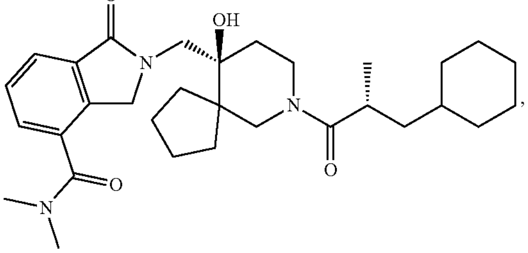,

-continued

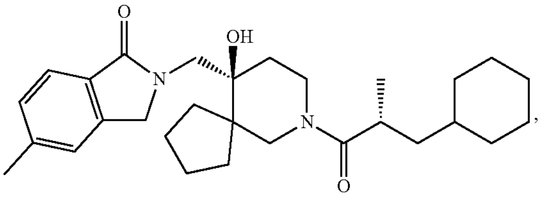,

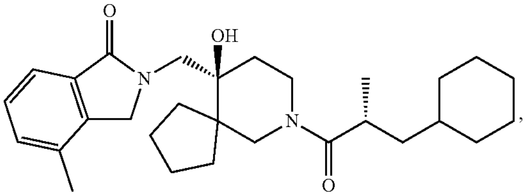,

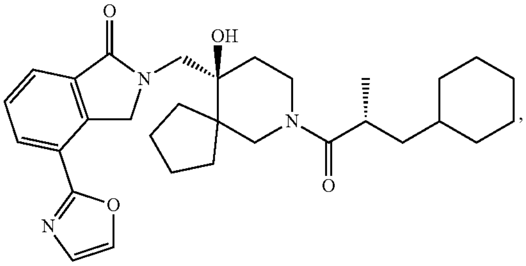,

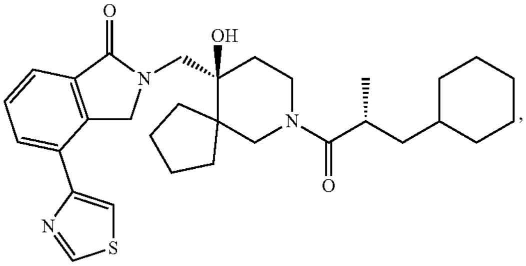,

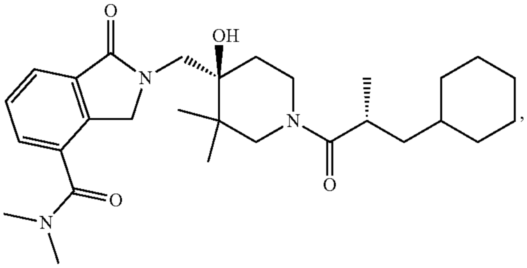,

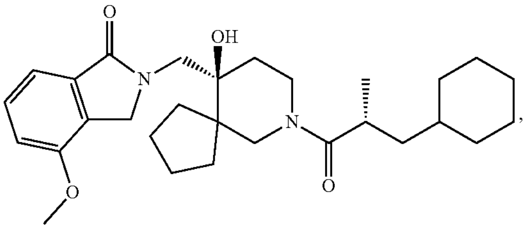,

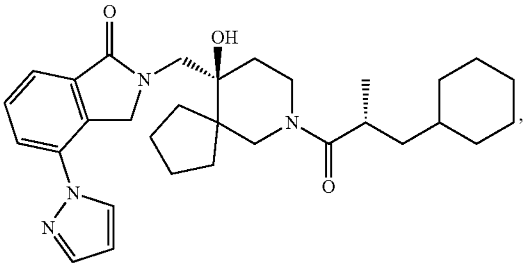,

-continued
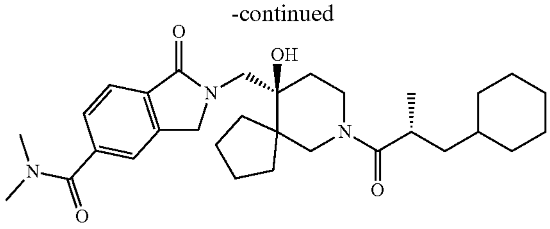
,
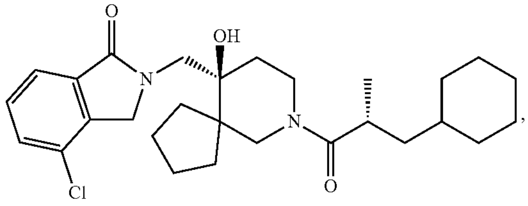
,
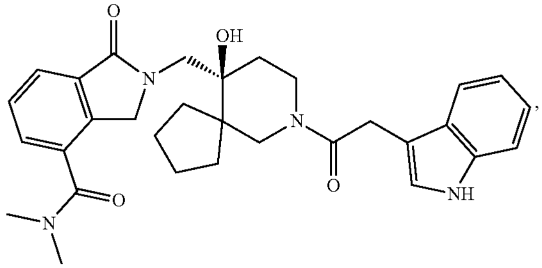
,
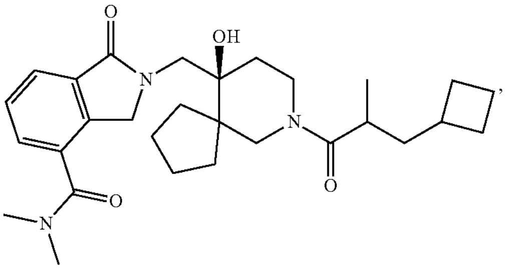
,
-continued
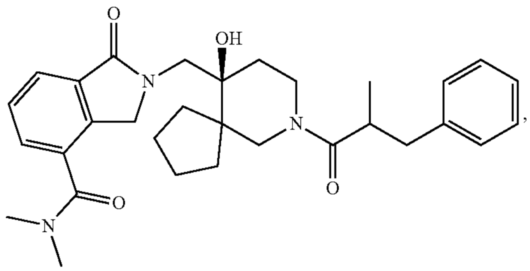
,
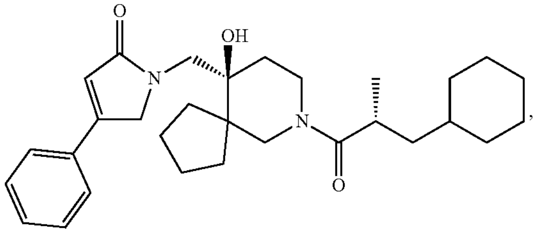
, or
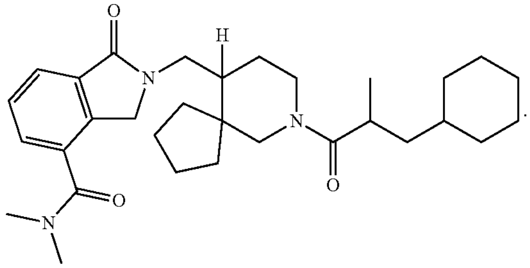
.
* * * * *